United States Patent
Schmidt et al.

(10) Patent No.: US 8,889,374 B2
(45) Date of Patent: Nov. 18, 2014

(54) RECOMBINANT CODON OPTIMISED FACTOR H

(75) Inventors: Christoph Schmidt, Edinburgh (GB); Paul N. Barlow, Edinburgh (GB); Anna Richards, Edinburgh (GB)

(73) Assignee: University Court of the University of Edinburgh, Edinburgh (GB)

( * ) Notice: Subject to any disclaimer, the term of this patent is extended or adjusted under 35 U.S.C. 154(b) by 0 days.

(21) Appl. No.: 13/518,614

(22) PCT Filed: Dec. 23, 2010

(86) PCT No.: PCT/GB2010/002334
§ 371 (c)(1), (2), (4) Date: Sep. 28, 2012

(87) PCT Pub. No.: WO2011/077102
PCT Pub. Date: Jun. 30, 2011

(65) Prior Publication Data
US 2013/0225795 A1    Aug. 29, 2013

(30) Foreign Application Priority Data
Dec. 24, 2009  (GB) .................................. 0922659.8

(51) Int. Cl.
| | |
|---|---|
| C12P 21/06 | (2006.01) |
| C07H 21/02 | (2006.01) |
| C07H 21/04 | (2006.01) |
| C12P 1/02 | (2006.01) |
| C12P 1/04 | (2006.01) |
| C12P 21/04 | (2006.01) |
| C12N 1/00 | (2006.01) |
| C12N 5/04 | (2006.01) |
| C12N 5/10 | (2006.01) |
| C12N 5/00 | (2006.01) |
| C12N 5/02 | (2006.01) |
| C12N 15/00 | (2006.01) |
| A61K 38/16 | (2006.01) |
| C07K 1/16 | (2006.01) |
| C07K 14/00 | (2006.01) |
| C07K 14/435 | (2006.01) |
| C07K 14/47 | (2006.01) |

(52) U.S. Cl.
CPC ........... C07K 14/4702 (2013.01); C07K 14/472 (2013.01)
USPC ......... 435/69.1; 435/69.6; 435/170; 435/171; 435/243; 435/320.1; 435/348; 435/410; 536/23.1; 536/23.5; 514/13.5; 514/21.2

(58) Field of Classification Search
None
See application file for complete search history.

(56) References Cited

U.S. PATENT DOCUMENTS

2007/0020647 A1    1/2007  Hageman et al.

2008/0221011 A1*   9/2008  Gilkeson et al. ................ 514/2

FOREIGN PATENT DOCUMENTS

| WO | WO2007/038995 | 4/2007 |
| WO | WO2008/135237 | 11/2008 |

OTHER PUBLICATIONS

Tedeschi-Blok et al., "Population-Based Study of Early Age-Related Macular Degeneration" 114(1) Ophthalmology 99-103 (2007).*
Kavenagh et al., "The decay accelerating factor mutation I197V found in hemolytic uraemic syndrome does not impair complement regulation" 44 Molecular Immunology 3162-3167 (2007).*
Lau et al., "Dense deposit disease and the factor H H402 allele" 12 Clinical and Experimental Nephrology 228-232 (2008).*
Herbert et al., "Structural and functional studies of C-terminal domains of complement factor H" 41 Molecular Immunology 243-244 (2004).*
Sharma et al., "Identification of three physically and functionally distinct binding sites for C3b in human complement factor H by deletion mutagenesis" 93 Proceedings of the National Academy of Sciences USA 10996-11001 (1996).*
Schmidt et al., "A New Map of Glycosaminoglycan and C3b Binding Sites on Factor H" 181 The Journal of Immunology 2610-2619 (2008).*
PCT International Search Report/Written Opinion prepared for PCT/GB2010/002334, mailed Jun. 6, 2011.
D'Anjou, Marc C., et al., "A Rational Approach to Improving Productivity in Recombinant *Pichia pastoris* Fermentation", 2001, Biotechnology and Bioengineering, vol. 72, No. 1, pp. 1-11.
Lorimer, Don, et al., "Gene Composer : Database Software for Protein Construct Design, Codon Engineering, and Gene Synthesis", 2009, BMC Biotechnology, vol. 9, No. 36, pp. 1-22.
Ormsby, R. J., et al., "Expresssion of Human Factor H in the Methyltrophic Yeast *Pichia pastoris*", 1988, Abstract, Molecular Immunology, vol. 35, No. 6-7, pp. 353.
Rabhi-Essafi, Imen, et al., "Codon Optimization to Improve the Production Yield of Recombinant Human Interferon α by *Pichia pastoris*", 2007, Abstract, Journal of Biotechnology, vol. 131, No. 2, pp. S7.
Schmidt, Christoph, et al., "Production of Biologically Active Complement Factor H in Therapeutically Useful Quantities", 2011, Protein Expression and Purification, No. 76, pp. 254-263.
Sinclair, Graham, et al., "Synonymous Codon Usage Bias and the Expression of Human Glucocerebrosidase in the Methylotrophic Yeast, *Pichia pastoris*", 2002, Protein Expression and Purfication, No. 26, pp. 96-105.
Tsai, Chiawei W., et al., "Overproduction of *Pichia pastoris* or *Plasmodium falciparum* Protein Disulfide Isomerase Affects Expression, Folding and O-Linked Glycosylation of a Malaria Vaccine Canidate Expressed in *P. pastoris*", 2006, Journal of Biotechnology, No. 121, pp. 458-470.

* cited by examiner

*Primary Examiner* — Anne Gussow
*Assistant Examiner* — Nancy J. Leith
(74) *Attorney, Agent, or Firm* — Barnes & Thornburg LLP

(57) ABSTRACT

The present invention relates to recombinant factor H and variants and conjugates thereof and methods of their production, as well as uses and methods of treatment involving the materials.

22 Claims, 16 Drawing Sheets

Figure 1

Figure 3:
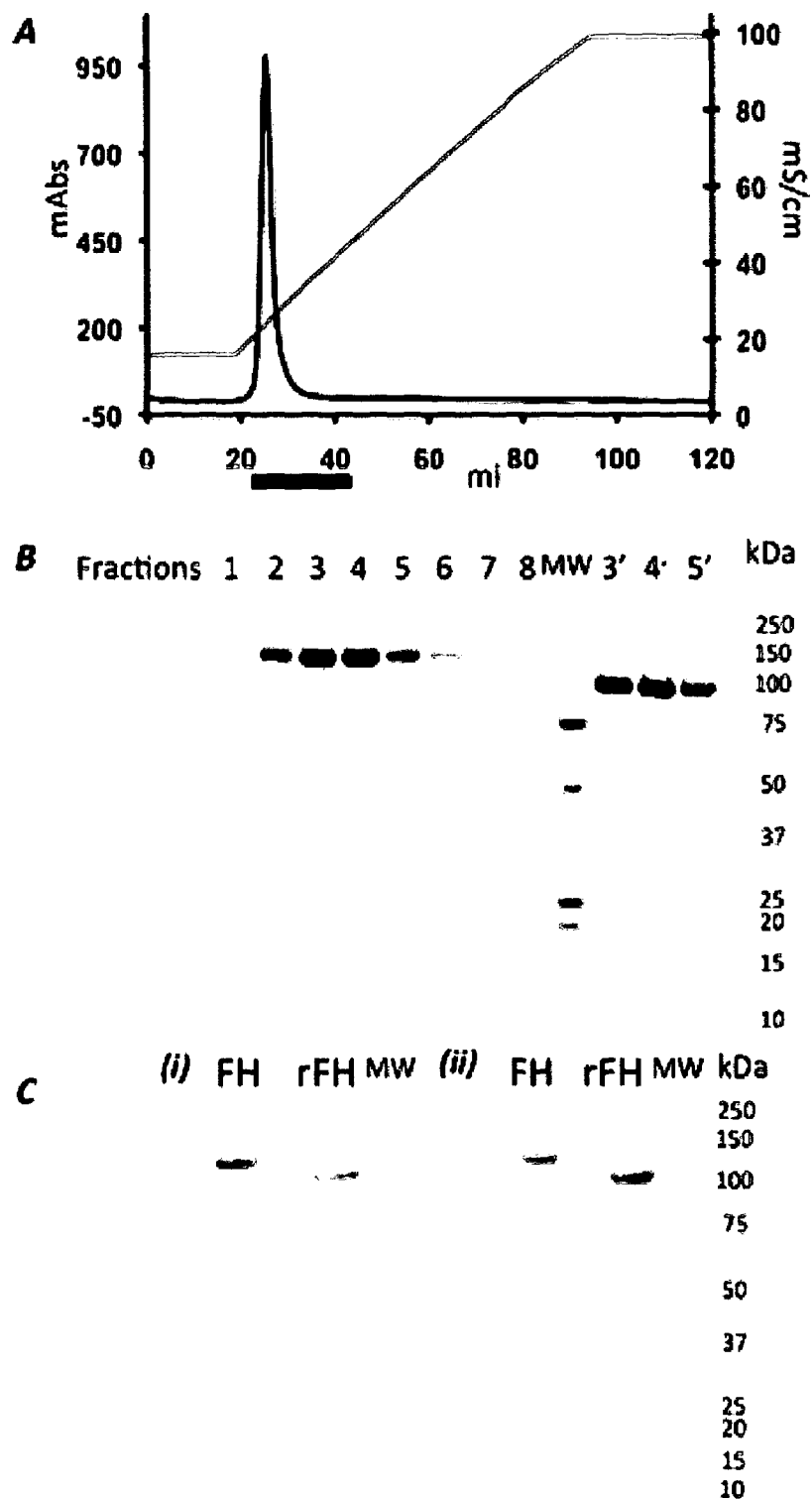
Figure 3:
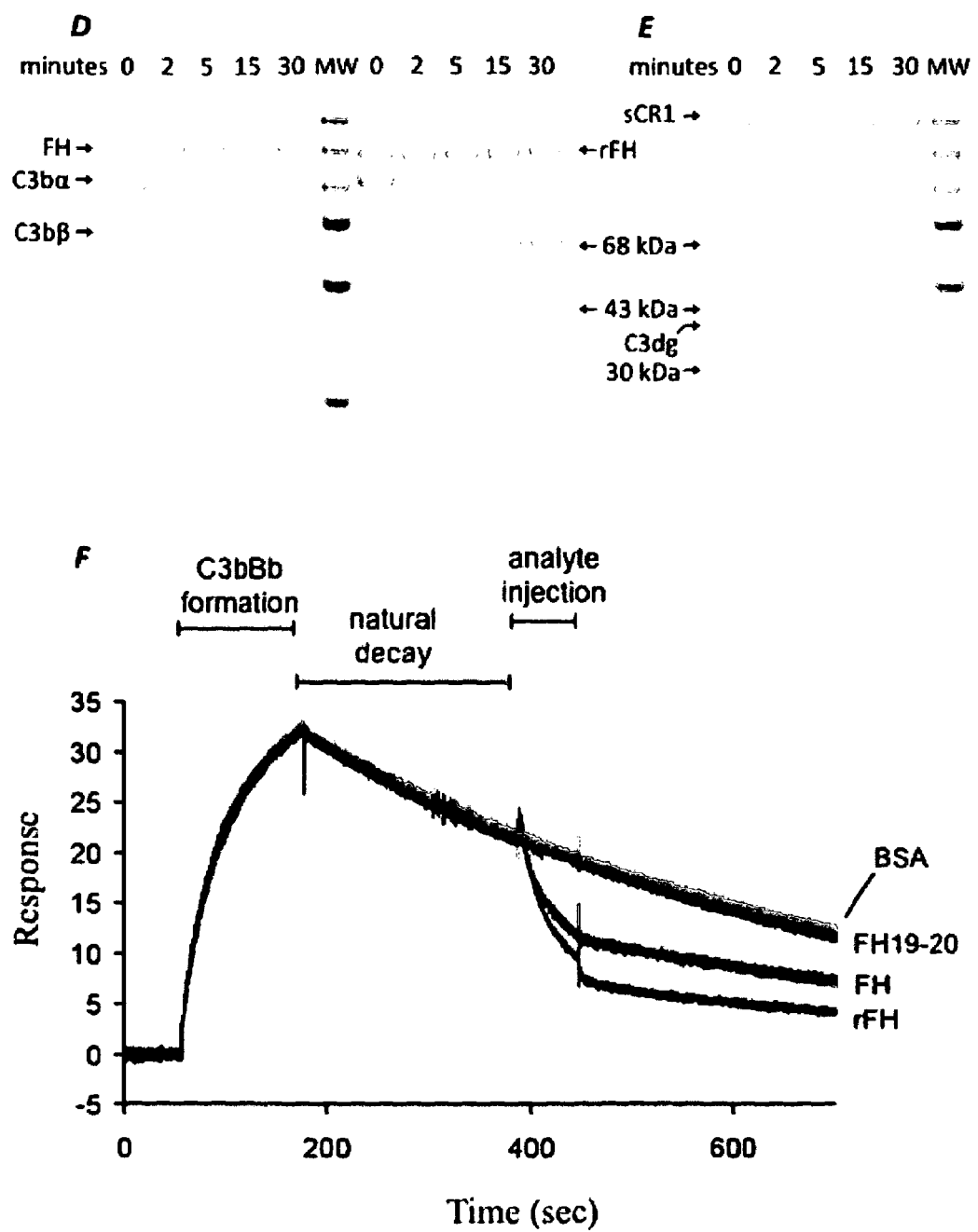
Figure 3:
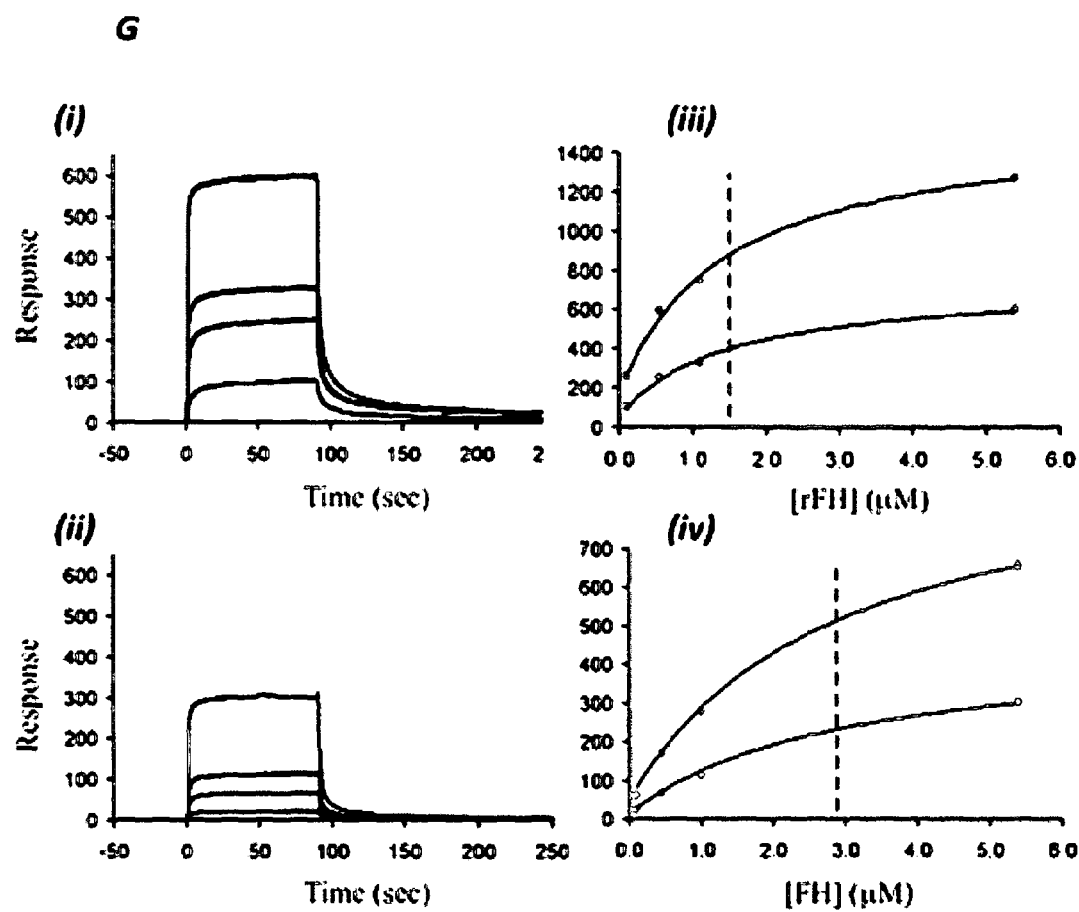
Figure 3:
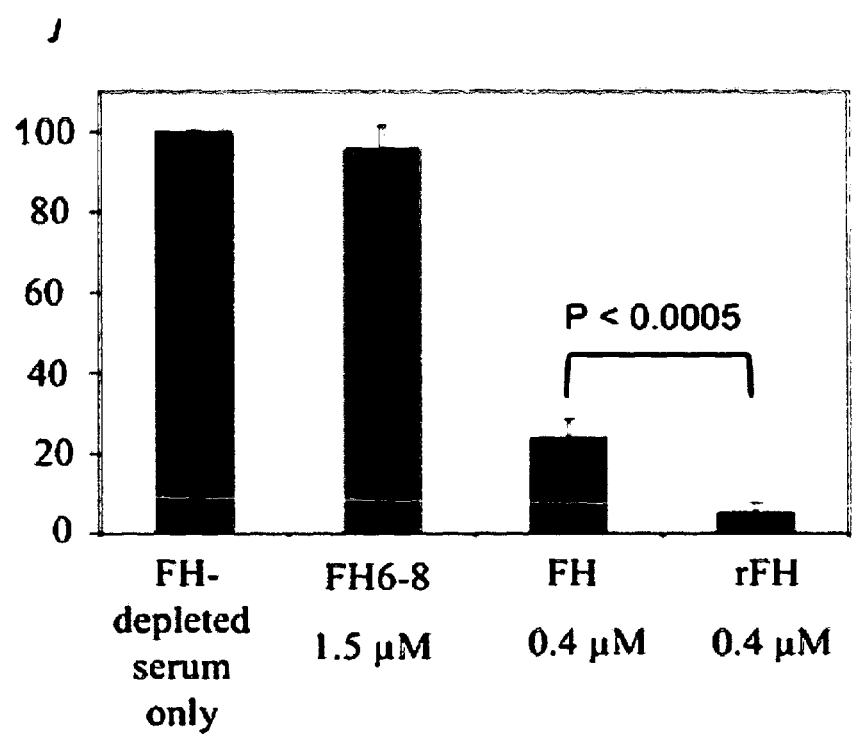

| | |
|---|---|
| Wild-type | GGAGATTGCAATGAACTTCCTCCAAGAAGAAATACAGAAATTCTGACAGGTTCCTGGTCT 60 |
| Codon-opt | GAGGATTGTAACGAGTTGCCACCAAGAAGAAACACTGAGATCTTGACTGGTTCTTGGAGT 60 |
| | *  ***** ** **  * ** *********** ** ** **  **** ***** ***  * |
| Wild-type | GACCAAACATATCCAGAAGGCACCCAGGCTATCTATAAATGCCGCCCTGGATATAGATCT 120 |
| Codon-opt | GATCAAACTTACCCAGAGGGTACTCAGGCTATCTACAAGTGTAGACCAGGTTACAGATCC 120 |
| | ** ***** ** ***** ** ** ********** ** **  * ** ** ** ***** |
| Wild-type | CTTGGAAATGTAATAATGGTATGCAGGAAGGGAGAATGGGTTGCTCTTAATCCATTAAGG 180 |
| Codon-opt | TTGGGTAACGTTATCATGGTTTGTAGAAAGGGTGAGTGGGTTGCATTGAACCCATTGAGA 180 |
| | * ** ** ** ** ***** ** ** ***** ** ********  * ** ***** ** |
| Wild-type | AAATGTCAGAAAAGGCCCTGTGGACATCCTGGAGATACTCCTTTTGGTACTTTTACCCTT 240 |
| Codon-opt | AAGTGTCAGAAAAGACCATGTGGTCACCCAGGTGATACTCCATTCGGTACTTTCACTTTG 240 |
| | ** *********** ** ***** ** ** ** ******** ** ******** **  * |
| Wild-type | ACAGGAGGAAATGTGTTTGAATATGGTGTAAAAGCTGTGTATACATGTAATGAGGGGTAT 300 |
| Codon-opt | ACTGGTGGTAACGTTTTCGAGTACGGTGTTAAGGCTGTTTACACTTGTAACGAGGGTTAC 300 |
| | ** ** ** ** ** ** ** ** ** ***** ** ***** ** ** ***** ***** ** |
| Wild-type | CAATTGCTAGGTGAGATTAATTACCGTGAATGTGACACAGATGGATGGACCAATGATATT 360 |
| Codon-opt | CAGTTGTTGGGAGAGATCAACTACAGAGAGTGTGATACTGACGGATGGACTAACGACATT 360 |
| | ** *** * ** ***** ** *** * ** ***** ** ** ******** ** ** *** |
| Wild-type | CCTATATGTGAAGTTGTGAAGTGTTTACCAGTGACAGCACCAGAGAATGGAAAAATTGTC 420 |
| Codon-opt | CCAATCTGTGAAGTTGTTAAGTGTTTGCCAGTTACTGCTCCAGAGAACGGAAAGATTGTT 420 |
| | ** ** *********** ******** ***** ** ** ******** ***** ***** |
| Wild-type | AGTAGTGCAATGGAACCAGATCGGGAATACCATTTTGGACAAGCAGTACGGTTTGTATGT 480 |
| Codon-opt | TCCTCCGCTATGGAACCAGATAGAGAGTACCACTTCGGACAGGCTGTTAGATTCGTTTGT 480 |
| | ** ************ * ** ***** ** ***** ** ** * ** ** ** *** |
| Wild-type | AACTCAGGCTACAAGATTGAAGGAGATGAAGAAATGCATTGTTCAGACGATGGTTTTTGG 540 |
| Codon-opt | AACTCCGGTTACAAGATTGAAGGTGACGAAGAGATGCACTGTTCTGATGACGGTTTCTGG 540 |
| | ***** ** ************** ** ***** ***** ***** ** ** ***** *** |
| Wild-type | AGTAAAGAGAAACCAAAGTGTGTGGAAATTTCATGCAAATCCCCAGATGTTATAAATGGA 600 |
| Codon-opt | TCCAAAGAAAAGCCAAAGTGTGTTGAGATCTCCTGTAAGTCCCCAGACGTTATTAACGGT 600 |
| | ***** ** *********** ** ** ** ** ******** ***** ** ** |
| Wild-type | TCTCCTATATCTCAGAAGATTATTTATAAGGAGAATGAACGATTTCAATATAAATGTAAC 660 |
| Codon-opt | TCCCCAATCTCCCAAAAGATCATCTACAAAGAGAACGAGAGATTCCAGTACAAGTGTAAC 660 |
| | ** ** ** ** ** ***** ** ** ** ***** **  **** ** ** ** ****** |
| Wild-type | ATGGGTTATGAATACAGTGAAAGAGGAGATGCTGTATGCACTGAATCTGGATGGCGTCCG 720 |
| Codon-opt | ATGGGTTACGAGTACTCTGAAAGAGGTGACGCTGTTTGTACTGAATCTGGATGGAGACCA 720 |
| | ******** ** ***  ********* ** ***** ** *************** *  ** |
| Wild-type | TTGCCTTCATGTGAAGAAAAATCATGTGATAATCCTTATATTCCAAATGGTGACTACTCA 780 |
| Codon-opt | TTGCCATCCTGTGAAGAGAAGTCCTGTGACAACCCATACATTCCAAACGGTGACTACTCC 780 |
| | ***** ** ******** ** ** ***** ** ** ** ********* ********** |

Figure 1 cont.

```
Wild-type    CCTTTAAGGATTAAACACAGAACTGGAGATGAAATCACGTACCAGTGTAGAAATGGTTTT   840
Codon-opt    CCATTGAGAATCAAGCACAGAACTGGTGACGAGATCACTTACCAGTGTAGAAATGGTTTC   840
             ** ** ** ** ** ********** ** ** ***** **********************

Wild-type    TATCCTGCAACCCGGGGAAATACAGCCAAATGCACAAGTACTGGCTGGATACCTGCTCCG   900
Codon-opt    TACCCAGCTACTAGAGGTAACACTGCTAAGTGTACTTCCACTGGATGGATTCCAGCTCCA   900
             ** ** ** **  * ** ** ** ** ** ** ** **     ***** ***** ** *****

Wild-type    AGATGTACCTTGAAACCTTGTGATTATCCAGACATTAAACATGGAGGTCTATATCATGAG   960
Codon-opt    AGATGTACTTTGAAGCCATGTGACTACCCAGATATCAAGCACGGTGGTTTGTACCACGAG   960
             ********  *****  ** ** ***** ** ***** ** ** *** * ** ** ***

Wild-type    AATATGCGTAGACCATACTTTCCAGTAGCTGTAGGAAAATATTACTCCTATTACTGTGAT   1020
Codon-opt    AACATGAGAAGGCCATACTTCCCAGTTGCTGTTGGAAAGTACTACTCCTACTACTGTGAC   1020
             ** *** * **  ******** ***** ***** ***** ** ********* ********

Wild-type    GAACACTTTGAGACTCCGTCAGGAAGTTACTGGGATCACATTCATTGCACACAAGATGGA   1080
Codon-opt    GAACACTTCGAAACTCCATCTGGTTCTTACTGGGACCACATCCACTGTACTCAAGATGGT   1080
             ******** ** ***** ** ** **  ******** ***** ** ** ** ********

Wild-type    TGGTCGCCAGCAGTACCATGCCTCAGAAAATGTTATTTTCCTTATTTGGAAAATGGATAT   1140
Codon-opt    TGGTCCCCAGCTGTTCCATGTTTGAGAAAATGTTACTTCCCATACTTGGAGAACGGTTAC   1140
             *****  *****  ** *****    * ***********  ** ** *****  ** ** **

Wild-type    AATCAAAATTATGGAAGAAAGTTTGTACAGGGTAAATCTATAGACGTTGCCTGCCATCCT   1200
Codon-opt    AACCAGAACTACGGTAGAAAGTTCGTTCAGGGAAAGTCCATTGACGTTGCTTGTCATCCA   1200
             ** ** ** ** ** ********* ** ***** ** ** ** ********** ** *****

Wild-type    GGCTACGCTCTTCCAAAAGCGCAGACCACAGTTACATGTATGGAGAATGGCTGGTCTCCT   1260
Codon-opt    GGTTACGCTTTGCCAAAGGCTCAGACTACTGTTACTTGTATGGAAAACGGTTGGTCCCCT   1260
             ** ****** * ***** ** ***** ** ***** ********  ** ** ***** ***

Wild-type    ACTCCCAGATGCATCCGTGTCAAAACATGTTCCAAATCAAGTATAGATATTGAGAATGGG   1320
Codon-opt    ACTCCTAGATGTATCAGAGTTAAGACTTGTTCCAAGTCCTCCATCGACATTGAGAACGGT   1320
             ***** ***** *** * ** ** ** ******** **    ** ** ******** **

Wild-type    TTTATTTCTGAATCTCAGTATACATATGCCTTAAAAGAAAAAGCGAAATATCAATGCAAA   1380
Codon-opt    TTCATTTCCGAGTCCCAGTACACTTACGCTTTGAAAGAGAAGGCTAAGTACCAGTGTAAA   1380
             ** ***** ** ** ***** ** ** ** ** ****** ** ** ** ** ********

Wild-type    CTAGGATATGTAACAGCAGATGGTGAAACATCAGGATCAATTACATGTGGGAAAGATGGA   1440
Codon-opt    TTGGGATACGTTACTGCTGACGGTGAAACTTCCGGATCAATACACATGTGGAAAAGACGGA   1440
             *  ***** ** ** ** ** ********  ** ******** ******** ** ***

Wild-type    TGGTCAGCTCAACCCACGTGCATTAAATCTTGTGATATCCCAGTATTTATGAATGCCAGA   1500
Codon-opt    TGGAGTGCTCAACCAACTTGTATCAAGTCTTGTGACATCCCAGTTTTCATGAACGCTAGA   1500
             ***   ******** ** ** ** ** ********* ******** ** ***** ** ***

Wild-type    ACTAAAAATGACTTCACATGGTTTAAGCTGAATGACACATTGGACTATGAATGCCATGAT   1560
Codon-opt    ACTAAGAACGACTTCACATGGTTCAAGTTGAACGACACTTTGGACTACGAATGTCACGAC   1560
             ***** ** ***************  *** **** ***** ********** ***** ** **
```

Figure 1 cont.

```
Wild-type    GGTTATGAAAGCAATACTGGAAGCACCACTGGTTCCATAGTGTGTGGTTACAATGGTTGG 1620
Codon-opt    GGTTACGAATCTAACACTGGTTCCACTACTGGTTCCATCGTTTGTGGTTACAATGGATGG 1620
             ***** ***   ** *****    *** ***********  ** **************** ***

Wild-type    TCTGATTTACCCATATGTTATGAAAGAGAATGCGAACTTCCTAAAATAGATGTACACTTA 1680
Codon-opt    AGTGACTTGCCAATCTGTTACGAGAGAGAGTGCGAGTTGCCAAAGATCGACGTTCATTTG 1680
             ***  ** ** ** ** ***** **  ***** *****   * **  ** **  ** **  ** **

Wild-type    GTTCCTGATCGCAAGAAAGACCAGTATAAAGTTGGAGAGGTGTTGAAATTCTCCTGCAAA 1740
Codon-opt    GTTCCAGACAGAAAGAAGGACCAGTACAAAGTTGGAGAGGTTTTGAAGTTCTCCTGTAAG 1740
             ***** **   *  *****  *********  *************** *****  ******** **

Wild-type    CCAGGATTTACAATAGTTGGACCTAATTCCGTTCAGTGCTACCACTTTGGATTGTCTCCT 1800
Codon-opt    CCAGGTTTCACTATCGTTGGTCCAAACTCCGTTCAGTGTTACCACTTCGGTTTGTCTCCA 1800
             ***** ** ** **  ***** **    ***********  *******  ** ********

Wild-type    GACCTCCCAATATGTAAAGAGCAAGTACAATCATGTGGTCCACCTCCTGAACTCCTCAAT 1860
Codon-opt    GACTTGCCTATCTGTAAAGAGCAGGTTCAATCCTGCGGACCACCACCAGAATTGTTGAAC 1860
             ***  * ** **  ************ ** ***** ** **  ***** ** ***  *  * **

Wild-type    GGGAATGTTAAGGAAAAAACGAAAGAAGAATATGGACACAGTGAAGTGGTGGAATATTAT 1920
Codon-opt    GGTAACGTTAAAGAAAAGACTAAAGAAGAGTACGGTCACTCCGAAGTTGTTGAGTACTAC 1920
             ** ** *****  ***** ** ********  **  ** ***       ***** ** ** ** **

Wild-type    TGCAATCCTGGATTTCTAATGAAGGGACCTAATAAAATTCAATGTGTTGATGGAGAGTGG 1980
Codon-opt    TGTAACCCAAGATTCTTGATGAAGGGTCCAAACAAGATCCAATGTGTTGACGGTGAGTGG 1980
             ** ** **   ****  * ********  ** **  ** ** ************  ** ******

Wild-type    ACAACTTTACCAGTGTGTATTGTGGAGGAGAGTACCTGTGGAGATATACCTGAACTTGAA 2040
Codon-opt    ACTACTTTGCCAGTTTGTATCGTTGAAGAGTCCACTTGTGGTGACATTCCAGAATTGGAA 2040
             ** *****  *****  ****  ** **  ***** **  **  **  **  ** ****  * ***

Wild-type    CATGGCTGGGCCCAGCTTTCTTCCCCTCCTTATTACTATGGAGATTCAGTGGAATTCAAT 2100
Codon-opt    CACGGATGGGCTCAATTGTCATCCCCACCATACTACTACGGTGACTCCGTTGAATTCAAC 2100
             ** ** *****  **   * ** *****  ** ** ***** ** ** ** ********

Wild-type    TGCTCAGAATCATTTACAATGATTGGACACAGATCAATTACGTGTATTCATGGAGTATGG 2160
Codon-opt    TGTTCCGAGTCCTTCACTATGATTGGTCACAGATCCATCACATGTATCCACGGTGTTTGG 2160
             ** ** ** ** ** ** ******** ********  ** ** ***** ** ** ** ***

Wild-type    ACCCAACTTCCCCAGTGTGTGGCAATAGATAAACTTAAGAAGTGCAAATCATCAAATTTA 2220
Codon-opt    ACTCAATTGCCACAGTGTGTTGCTATCGACAAGTTGAAGAAGTGTAAATCATCCAACCTT 2220
             ** ***  * ** ********  ** ** **  * ********  ******** **   *

Wild-type    ATTATACTTGAGGAACATTTAAAAAACAAGAAGGAATTCGATCATAATTCTAACATAAGG 2280
Codon-opt    ATCATCTTGGAGGAACACTTGAAGAACAAGAAAGAGTTCGACCACAACTCCAACATCAGA 2280
             ** **   * ******** ** ** ********  ** *****  ** ** ** ***** **

Wild-type    TACAGATGTAGAGGAAAAGAAGGATGGATACACACAGTCTGCATAAATGGAAGATGGGAT 2340
Codon-opt    TACAGATGTAGAGGTAAAGAGGGATGGATCCACACTGTTTGTATCAACGGTAGATGGGAC 2340
             ************** *****  *******  ***** ** ** **  ** ** ********
```

Figure 1 cont.

```
Wild-type    CCAGAAGTGAACTGCTCAATGGCACAAATACAATTATGCCCACCTCCACCTCAGATTCCC 2400
Codon-opt    CCTGAAGTTAACTGTTCCATGGCTCAGATTCAGTTGTGTCCACCACCACCACAAATTCCA 2400
             ** ***** ***** ** ***** ** ** ** ** ** ***** ***** ** *****

Wild-type    AATTCTCACAATATGACAACCACACTGAATTATCGGGATGGAGAAAAAGTATCTGTTCTT 2460
Codon-opt    AACTCCCACAACATGACTACTACTTTGAACTACAGAGATGGTGAAAAGGTTTCCGTTTTG 2460
             ** ** ***** ***** ** **  **** ** * ***** ***** ** ** *** *

Wild-type    TGCCAAGAAAATTATCTAATTCAGGAAGGAGAAGAAATTACATGCAAAGATGGAAGATGG 2520
Codon-opt    TGTCAAGAGAACTACTTGATCCAAGAGGGTGAAGAGATCACATGTAAGGACGGTAGATGG 2520
             ** ***** ** **  * ** ** ** ** ***** ** ***** ** ** ** ******

Wild-type    CAGTCAATACCACTCTGTGTTGAAAAAATTCCATGTTCACAACCACCTCAGATAGAACAC 2580
Codon-opt    CAGTCCATCCCTTTGTGTGTTGAGAAGATCCCATGTTCCCAACCACCTCAAATTGAGCAC 2580
             ***** ** **  * ******** ** ** ******** ************ ** ** ***

Wild-type    GGAACCATTAATTCATCCAGGTCTTCACAAGAAAGTTATGCACATGGGACTAAATTGAGT 2640
Codon-opt    GGTACTATCAACTCTTCCAGATCCTCTCAAGAGTCTTACGCTCACGGTACTAAGTTGTCC 2640
             ** ** ** ** ** ***** ** ** ***** *** ** ** ** ***** ***

Wild-type    TATACTTGTGAGGGTGGTTTCAGGATATCTGAAGAAAATGAAACAACATGCTACATGGGA 2700
Codon-opt    TACACTTGTGAGGGAGGTTTCAGAATCTCTGAGGAAAACGAGACTACTTGTTACATGGGA 2700
             ** *********** ******** ** ***** ***** ** ** ** ** *********

Wild-type    AAATGGAGTTCTCCACCTCAGTGTGAAGGCCTTCCTTGTAAATCTCCACCTGAGATTTCT 2760
Codon-opt    AAGTGGTCATCTCCACCACAATGTGAAGGATTGCCTTGTAAGTCTCCACCAGAGATTTCT 2760
             ** ***   ******** ** ******** * ******** ******** *********

Wild-type    CATGGTGTTGTAGCTCACATGTCAGACAGTTATCAGTATGGAGAAGAAGTTACGTACAAA 2820
Codon-opt    CACGGTGTTGTTGCTCACATGTCCGACTCTTACCAATACGGAGAAGAGGTTACCTACAAG 2820
             ** ******** *********** ** ** *** ** ** ******** ***** *****

Wild-type    TGTTTTGAAGGTTTTGGAATTGATGGGCCTGCAATTGCAAAATGCTTAGGAGAAAAATGG 2880
Codon-opt    TGTTTCGAGGGTTTCGGTATTGATGGTCCAGCTATCGCTAAGTGTTTGGGAGAAAAGTGG 2880
             ***** ** ***** ** ******** ** ** ** ** ** ** ** ********* ***

Wild-type    TCTCACCCTCCATCATGCATAAAAACAGATTGTCTCAGTTTACCTAGCTTTGAAAATGCC 2940
Codon-opt    TCCCATCCTCCATCCTGTATCAAGACTGATTGTTTGTCCTTGCCATCCTTCGAAAACGCT 2940
             ** ** ******** ** ** ** ** ****** *    ** **  *** ***** **

Wild-type    ATACCCATGGGAGAGAAGAAGGATGTGTATAAGGCGGGTGAGCAAGTGACTTACACTTGT 3000
Codon-opt    ATCCCAATGGGAGAAAAGAAGGACGTTTACAAGGCTGGTGAACAAGTTACTTATACTTGT 3000
             ** ** ******** ******** ** ** ***** ***** ***** ***** ******

Wild-type    GCAACATATTACAAAATGGATGGAGCCAGTAATGTAACATGCATTAATAGCAGATGGACA 3060
Codon-opt    GCTACTTACTACAAGATGGACGGTGCTTCCAACGTTACTTGTATCAACTCCAGATGGACT 3060
             ** ** ** ***** ***** ** **    ** ** ** ** ** **  *********

Wild-type    GGAAGGCCAACATGCAGAGACACCTCCTGTGTGAATCCGCCCACAGTACAAAATGCTTAT 3120
Codon-opt    GGTAGACCAACTTGTAGAGACACTTCCTGTGTTAACCCACCAACTGTTCAGAACGCTTAC 3120
             ** ** ***** ** ******** ******** ** ** ** ** ** ** ** *****
```

Figure 1 cont.

```
Wild-type   ATAGTGTCGAGACAGATGAGTAAATATCCATCTGGTGAGAGAGTACGTTATCAATGTAGG 3180
Codon-opt   ATCGTTTCCAGACAGATGTCTAAGTACCCATCCGGAGAACGTGTTAGATACCAATGTAGA 3180
            ** ** ** ********* *** ** ***** ** **  * **  * ** *******

Wild-type   AGCCCTTATGAAATGTTTGGGGATGAAGAAGTGATGTGTTTAAATGGAAACTGGACGGAA 3240
Codon-opt   TCCCCATACGAGATGTTCGGTGACGAAGAGGTTATGTGTTTGAACGGTAATTGGACTGAA 3240
             *** ** ** ***** ** ** ***** ** ******** ** ** ** ***** ***

Wild-type   CCACCTCAATGCAAAGATTCTACAGGAAAATGTGGGCCCCCTCCACCTATTGACAATGGG 3300
Codon-opt   CCACCACAGTGTAAGGACTCCACTGGTAAGTGTGGTCCACCTCCACCAATTGACAACGGT 3300
            ***** ** ** ** ** ** ** ** ** ***** ** ******** ******** **

Wild-type   GACATTACTTCATTCCCGTTGTCAGTATATGCTCCAGCTTCATCAGTTGAGTACCAATGC 3360
Codon-opt   GACATCACTTCTTTCCCTTTGTCCGTTTACGCTCCAGCTTCTTCCGTTGAGTACCAGTGT 3360
            ***** ***** ***** ** ** ** ** *********** ** *********** **

Wild-type   CAGAACTTGTATCAACTTGAGGGTAACAAGCGAATAACATGTAGAAATGGACAATGGTCA 3420
Codon-opt   CAGAACTTGTACCAGTTGGAGGGTAACAAGAGAATCACTTGTAGAAACGGACAATGGAGT 3420
            *********** **  * ************* **** ** ******** *********

Wild-type   GAACCACCAAAATGCTTACATCCGTGTGTAATATCCCGAGAAATTATGGAAAATTATAAC 3480
Codon-opt   GAGCCACCAAAGTGTTTGCACCCATGTGTTATCTCCAGAGAAATCATGGAAAACTACAAC 3480
            ** ******** ** ** ** ** ***** ** *** ******* ******** ** ***

Wild-type   ATAGCATTAAGGTGGACAGCCAAACAGAAGCTTTATTCGAGAACAGGTGAATCAGTTGAA 3540
Codon-opt   ATTGCTTTGAGATGGACTGCTAAACAGAAGTTGTACTCCAGAACTGGTGAATCCGTTGAG 3540
            ** ** ** ** ***** ** ********* * ** ** ***** ******** *****

Wild-type   TTTGTGTGTAAACGGGGATATCGTCTTTCATCACGTTCTCACACATTGCGAACAACATGT 3600
Codon-opt   TTCGTTTGTAAGAGAGGTTACAGATTGTCCTCCAGATCCCACACTTTGAGAACTACATGT 3600
            ** ** ***** * ** **  *  * ** **  * ** ***** *** **** ******

Wild-type   TGGGATGGGAAACTGGAGTATCCAACTTGTGCAAAAGATAG---  3642
Codon-opt   TGGGACGGAAAATTGGAGTACCCAACTTGTGCTAAGAGATAGTAG 3645
            ***** ** *** ******* *********** ** ******
```

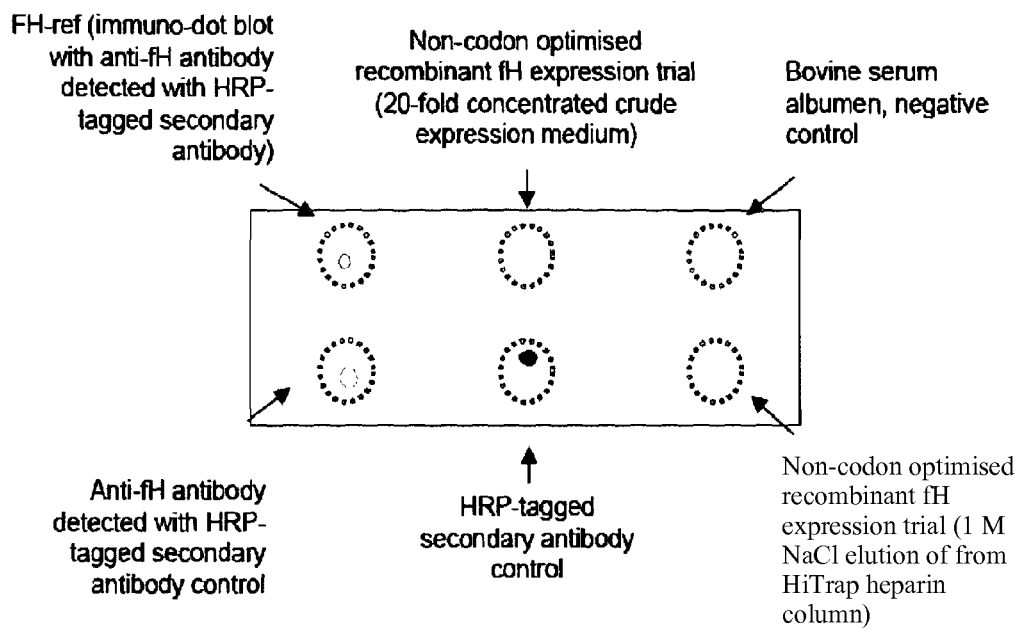

Figure 2: Trial for expression of recombinant human fH using DNA that was not optimised for codon usage

Legend to Figure 2: An attempted expression of recombinant fH in a three-litre fermentor trial was monitored using a standard immuno-blotting technique with a commercial polyclonal anti-fH antibody and secondary antibody coupled to horse radish peroxidase. A portion of the supernatant (after spinning out cells) was concentrated 20-fold while the remainder was diluted (to reduce salt concentration) and loaded onto a HiTrap (GE Healthcare) heparin column at 20 mM potassium phosphate, pH 6, and step eluted with 1 M NaCl in the same buffer. FH-ref is a reference sample of purchased from Comptech (Texas, USA).

Figure 3 cont.
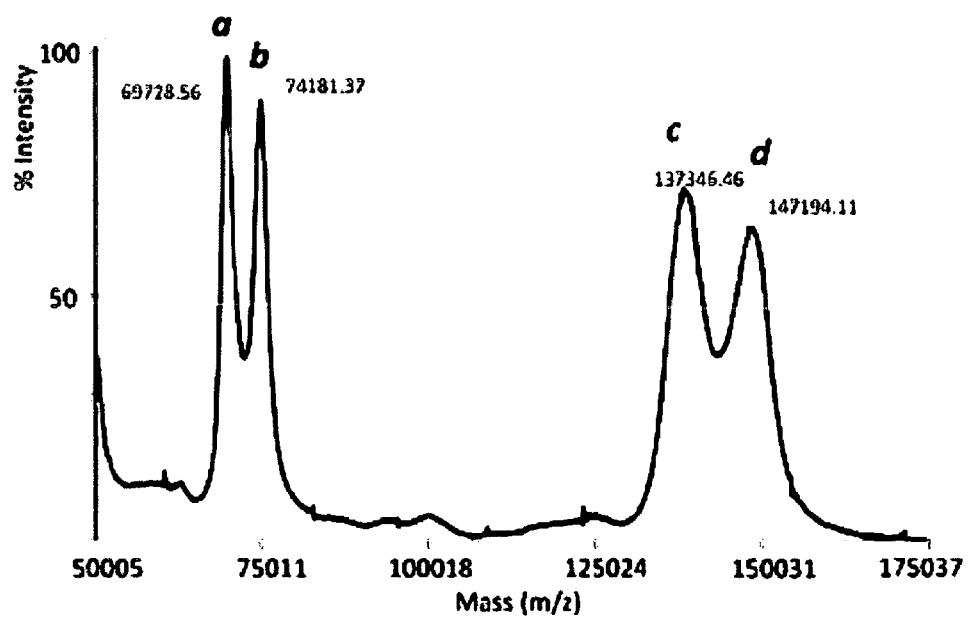
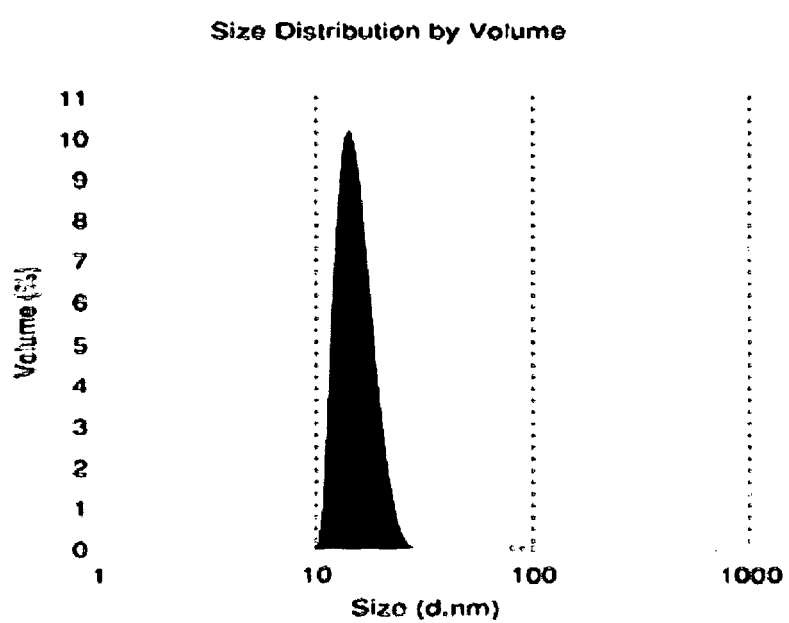

Figure 4
(A) Schematic of human factor H (fH) showing SNPs and N-glycans (🍡)
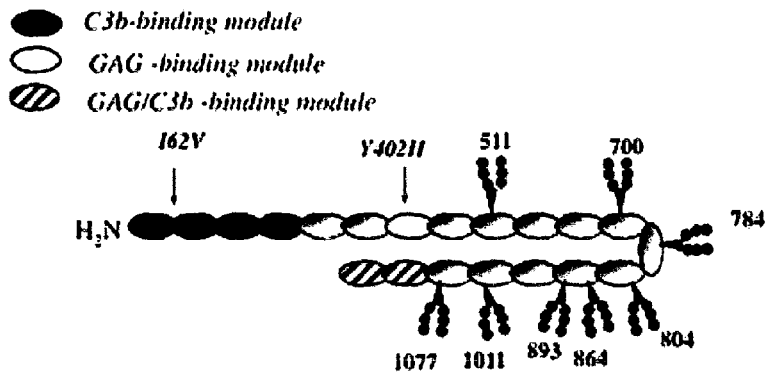
(B) Set of vectors designed for production of human and mouse fH variants
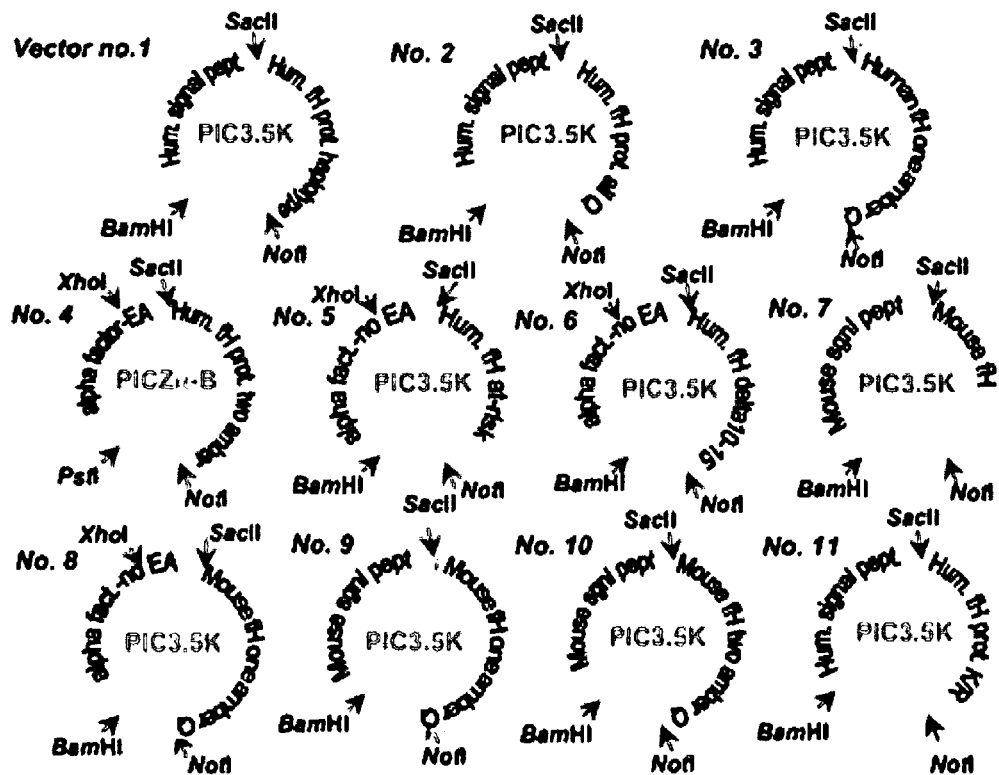

Figure 5A

| Human: construct no. 1 | 2 | 3 | 4 | 5 | 6 | 11 | * |
|---|---|---|---|---|---|---|---|
| GGCGCGCCGGATCCAAAAATGAGATTGTTGGCTAAGATCATCTGTTTGATGTTGTGGGCT | | | a | b | | | |
| ATCTGTGTTGCTGAGGACTGTAACGAATTGCCACCGCGGAGAAACACTGAGATTTTGACT | | | | | | | |
| GGTTCCTGGTCCGATCAAACTTACCCAGAGGGTACTCAGGCTATCTACAAGTGTAGACCA | | | | | | | |
| GGTTACAGATCCTTGGGTAACATCATCATGGTTTGTAGAAAGGGTGAGTGGGTTGCTTTG | | | | GTT | ATT | | I-V |
| AACCCATTGAGAAAGTGTCAGAAAAGACCATGTGGTCACCCAGGTGATACTCCATTCGGT | | | | | | | |
| ACTTTCACTTTGACTGGTGGTAACGTTTTCGAGTACGGTGTTAAGGCTGTTTACACTTGT | | | | | | | |
| AACGAGGGTTACCAGTTGTTGGGTGAGATCAACTACAGAGAGTGTGATACTGACGGTTGG | | | | | | | |
| ACTAACGACATTCCAATCTGTGAGGTTGTTAAGTGTTTGCCAGTTACTGCTCCAGAGAAC | | | | | | | |
| GGTAAGATTGTTTCCTCCGCTATGGAACCAGATAGAGAGTACCACTTCGGTCAGGCTGTT | | | | | | | |
| AGATTCGTTTGTAACTCCGGTTACAAGATTGAAGGTGACGAAGAGATGCACTGTTCTGAT | | | | | | | |
| GACGGTTTCTGGTCCAAAGAAAAGCCAAAGTGTGTTGAGATTTCCTGTAAGTCCCCAGAC | | | | | | | |
| GTTATTAACGGTTCCCCAATCTCCCAAAAGATCATCTACAAAGAGAACGAGAGATTCCAG | | | | | | | |
| TACAAGTGTAACATGGGTTACGAGTACTCTGAAAGAGGTGACGCTGTTTGTACTGAATCT | | | | | | | |
| GGTTGGAGACCATTGCCATCCTGTGAAGAGAAGTCCTGTGACAACCCATACATTCCAAAC | | | | | | | |
| GGTGACTACTCCCCATTGAGAATCAAGCACAGAACTGGTGCAGATCACTTACCAGTGT | | | | | | | |
| AGAAACGGTTTCTACCCAGCTACTAGAGGTAACACTGCTAAGTGTACTTCCACTGGTTGG | | | | | | | |
| ATTCCAGCTCCAAGATGTACTTTGAAGCCATGTGACTACCCAGATATCAAGCACGGTGGT | | | | | | | |
| TTGTACCACGAGAACATGAGAAGACCATACTTCCCAGTTGCTGTTGGAAAGTACTACTCC | | | | | | | |
| TACTACTGTGACGAACACTTCGAAACTCCATCTGGTTCTTACTGGGACCACATCCACTGT | | | | | | | |
| ACTCAAGATGGTTGGTCCCCAGCTGTTCCATGTTTGAGAAAATGTTACTTCCCATACTTG | | | | | | | |
| GAGAACGGTTACAACCAGAACTACGGTAGAAAGTTCGTTCAGGGAAAGTCCATTGACGTT | | | | CAT | | | Y-H |
| GCTTGTCATCCAGGTTACGCTTTGCCAAAGGCTCAGACTACTGTTACTTGTATGGAAAAC | | | | | | | |
| GGTTGGTCCCCTACTCCTAGATGTATCAGAGTTAAGACTTGTTCCAAGTCCTCCATCGAC | | | | | | | |
| ATTGAGAACGGTTTCATTTCCGAGTCCCAGTACACTTACGCTTTGAAAGAGAAGGCTAAG | | | | | | | |
| TACCAGTGTAAATTGGGATACGTTACTGCTGACGGTGAAACTTCCGGTTCCATCACTTGT | | | | | | | |
| GGTAAGGATGGTTGGTCTGCTCAACCAACTTGTATCAAGTCTTGTGACATCCCAGTTTTC | | | | | | | |
| ATGAACGCTAGAACTAAGAACGACTTCACATGGTTCAAGTTGAACGACACTTTGGACTAC | CAA | CAA | | | | | N-Q |
| GAATGTCACGACGGTTACGAATCTAACACTGGTTCCACTACTGGTTCCATCGTTTGTGGT | | | | | | | |
| TACAACGGTTGGTCTGACTTGCCAATCTGTTACGAGAGAGAGTGCGGTTGCCAAAGATC | | | | | c | | |
| GACGTTCATTTGGTTCCAGACAGAAAGAAGGACCAGTACAAGGTTGGTGAGGTTTTGAAG | | | | | | | |
| TTCTCCTGTAAGCCAGGGTTTCACTATCGTTGGTCCAAACTCCGTTCAGTGTTACCATTTC | | | | | | | |
| GGTTTGTCCCCAGACTTGCCTATTTGTAAAGAGCAGGTTCAGTCTTGCGGTCCACCACCA | | | | | | | |
| GAATTGTTGAACGGTAACGTTAAAGAAAAGACTAAAGAAGAGTACGGTCACTCTGACGTT | | | | | | | |
| GTTGAGTACTACTGTAACCCAAGATTCTTGATGAAGGGTCCAAACAAGATCCAATGTGTT | | | | | | | |
| GACGGTGAGTGGACTACTTTGCCAGTTTGTATCGTTGAAGAGTCCACTTGTGGTGACATT | | | | | | | |
| CCAGAATTGGAACACGGTTGGGCTCAATTGTCATCCCCACCATACTACGGTGACTC | | | | | | | |
| GTTGAGTTCAACTGTTCCGAGTCCTTCACTATGATTGGTCACAGATCCATCACATGTATC | CAA | CAA | TAG | | | | N-Q |
| CACGGTGTTTGGACTCAATTGCCACACAGTGTGTTGCTATCGACAAGTTGAAGAAGTGTAAA | | | | | | CAA | K-Q |
| TCCTCCAACTTGATCATCTTGGAGGAACACTTGAAGAACAAGAAAGAGTTCGACCACAAC | | | | | | CAA | K-Q |
| TCCAACATCAGATACAGATGTAGAGGTAAAGAGGGTTGGATTCACACTGTTTGTATCAAC | | | | | | CAA | X-Q |
| GGTAGATGGACCCTGAAGTTAACTGTTCCATGGCTCAGATTCAGTTGTGTCCACCACCT | CAA | CAA | | | | CAA | d |
| CCACAAATTCCAAACTCCCACAACATGACTACTACTTTGAACTACAGAGATGGTGAGAAG | CAA | CAA | | | | | N-Q |
| GTTTCCGTTTTGTGTCAAGAGAACTACTTGATCCAAGAGGGTGAGGAAATCACTTGTAAG | | | | | | | |
| GACGGTAGATGGCAATCCATCCCATTGTGTGTTGAGAAGATCCCATGTTCCCAACCACCA | | | | | | | |
| CAAATTGAGCACGGTACTATC**AAC*TCTTCC*AGATCCTCTCAAGAGTCTTACGCTCACGGT | CAA | CAA TCT AGT | | | | | e |
| ACTAAGTTGTCCTACACTTGTGAGGGTGGTTTCAGAATCTCTGAGGAAAACGAGACTACT | CAA | TAG | TAG | | | | N-Z |
| TGTTACATGGGAAAGTGGTCCTCTCCACCACAATGTGAAGGTTTGCCTTGTAAGTCTCCA | | | | | | | |
| CCAGAGATTTCTCACGGTGTTGTTGCTCACATGTCCGACTCTTACCAATACGGTGAAGAG | | | | | | | |
| GTTACTTACAAGTGTTTCGAGGGGTTTCGGTATTGATGGTCCAGCTATCGCTAAGTGTTTG | | | | | | | |
| GGTGAAAAGTGGTCCCATCCTCCATCCTGTATCAAGACTGACTGTTTGTCCTTGCCATCT | | | | | | | |
| TTCCGAGAACGCTATCCCAATGGGTGAAAAGAAGGACGTTTACAAGGCTGGTGAACAGGTT | | | | | | | |
| ACATACACTTGTGCTACTTACTACAAGATGGACGGTGCTTCCAACGTTACTTGTATCAAC | CAA | CAA | | | | | N-Z |
| TCCAGATGGACTGGTAGACCAACTTGTAGAGACACTTCCTGTGTTAACCCACCAACTGTT | | | | | | | |
| CAGAACGCTTACATCGTTTCCAGACAGATGTCTAAGTACCCATCCGGTGAGAGAGTTAGA | | | | | | | |
| TACCAATGTAGATCCCCATACGAGATGTTCGGTGACGAAGAGGTTATGTGTTTGAACGGT | | | | | | | |
| AATTGGACTGAACCACCACAGTGTAAGGACTCCACTGGTAAGTGTGGTCCACCTCCACCA | CAA | CAA | | | | | N-Z |
| ATTGACAACGGTGACATCACTTCTTTCCCATTGTCCGTTTACGCTCCAGCTTCTTCCGTT | | | | | | | |
| GAGTACCAGTGTCAGAACTTGTACCAGTTGGAAGGGTAACAAGAGAATCACTTGTAGAAAC | | | | | | | |
| GGACAATGGTCTGAGCCACCAAAGTGTTTGCACCCATGTGTTATCTCCAGAGAAATCATG | | | | | | | |
| GAAAACTACAACATTGCTTTGAGATGGACTGCTAAGCAGAAGTTGTACTCCAGAACAGGT | | | | | | | |
| GAGTCTGTTGAGTTTGTTTGTAAGAGAGGTTACAGATTGTCCTCCAGATCCCACACTTTG | | | | | | | |
| AGAACTACATGTTGGGACGGAAAGTTGGAGTACCCAACTTGTGCTAAGAGATAATGAGCG | | | | | | | |
| GCCGCTTAATTAA | | | | | | | |

\* Resultant changes in amino acid residue sequence; Z = Q or amber codon; X = Lys or Arg
ᵃ Entire sequence in bold on these two lines is replaced with the following sequence: CCTGCAGGT
ᵇ Entire underlined sequence replaced with the following sequence:
TTCCCATCCATCTTCACTGCTGTTTTGTTCGCTGCTTCTTCTGCTTTGGCTGCTCCAGTTAACACTACTACTGAGGACGAGACTGCTCAAATTCCAGCTGAGGCTG
TTATTGGTTACTCTGACTTGGAAGGTGATTTCGACGTTGCTGTTTTGCCATTCTCCAACTCCACTAACAACGGTTTGTTGTTCATCAACACTACTATCGCTTCCAT
TGCTGCTAAAGAAGAGGGAGTTTCCCTCGAGAAGAGA
ᶜ entire underlined sequence (corresponding to CCPs 10-15) deleted
ᵈ R-Q or N-Q/amber
ᵉ N-Q in construct 2, or N S S → Q S S in construct 3

Figure 5B

| Mouse: construct no. 7 | 8 | 9 | 10 | * |
|---|---|---|---|---|
| GGCGCGCCGGATCCAAAAATGAGATTGTCCGCTAGAATCATCTGGTTGATCTTGTGGACT | a | | | Alpha-factor, no EA |
| GTTTGTGCTGCTGAGGATTGTAAAGGTCCACCACCGCGGGAAAACTCCGAGATTTTGTCT | | | | |
| GGTTCTTGGTCCGAACAATTGTACCCAGAGGGTACTCAAGCTACTTACAAGTGTAGACCA | | | | |
| GGTTACAGAACTTTGGGTACTATCGTTAAGGTTTGTAAGAACGGAAAGTGGGTTGCTTCT | | | | |
| AACCCATCCAGAATCTGTAGAAAGAAACCATGTGGTCACCCAGGTGATACTCCATTCGGT | CAA | CAA | CAA | N - Q |
| TCCTTCAGATTGGCTGTTGGTTCCCAATTCGAGTTCGGTGCTAAGGTTGTTTACACTTGT | | | | |
| GACGACGGTTACCAATTGTTGGGTGAGATCGACTACAGAGAATGTGGTGCTGACGGTTGG | | | | |
| ATTAACGACATCCCATTGTGTGAGGTTGTTAAGTGTTTGCCAGTTACTGAGTTGGAGAAC | | | | |
| GGTAGAATTGTTTCTGGTGCTGCTGAAACTGACCAAGAGTACTTCGGACAGGTTGTT | | | | |
| AGATTCGAGTGTAACTCCGGTTTCAAGATCGAAGGTCACAAAGAGATTCACTGTTCCGAG | | | | |
| AACGGTTTGTGGTCTAACGAGAAGCCAAGATGTGTTGAGATTTTGTGTACTCCACCAAGA | | | | |
| GTTGAAAACGGTGACGGTATCAACGTTAAGCCAGTTTACAAAGAGAACGAGAGATACCAC | | | | |
| TACAAGTGTAAGCACGGTTACGTTCCAAAAGAAAGAGGTGACGCTGTTTGTACTGGTTCT | | | | |
| GGTTGGTCCTCTCAACCATTCTGTGAAGAGAAGAGATGTTCCCCACCATACATCTTGAAC | | | | |
| GGTATCTACACTCCACACAGAATCATTCACAGATCCGACGACGAGATTAGATACGAATGT | | | | |
| AACTACGGATTCTACCCAGTTACTGGTTCCACTGTTTCCAAGTGTACTCCAACTGGTTGG | | | | |
| ATTCCAGTTCCAAGATGTACTTTGAAGCCATGTGAGTTCCCACAATTCAAGTACGGTAGA | | | | |
| TTGTACTACGAAGAGTCCTTGAGACCAAACTTCCCAGTTTCCATCGGTAACAAGTACTCC | | | | |
| TACAAGTGTGACAACGGTTTCTCTCCACCATCTGGTTACTCTTGGGACTACTTGAGATGT | | | | |
| ACTGCTCAAGGTTGGGAACCAGAGGTTCCATGTGTTAGAAAGTGTGTTTTCCACTACGTT | | | | |
| GAGAACGGTGATTCTGCTTACTGGGAGAAGGTTTACGTTCAAGGTCAGTCCTTGAAGGTT | | | | |
| CAGTGTTACAACGGTTACTCCTTGCAAAACGGTCAGGACACTATGACTTGTACTGAGAAC | | | | |
| GGTTGGTCACCACCACCAAAGTGTATCAGAATCAAGACTTGTTCCGCTTCCGACATTCAC | | | | |
| ATCGACAACGGATTCTTGTCTGAGTCCTCCTCCATTTACGCTTTGAACAGAGAGACTTCC | | | | |
| TACAGATGTAAGCAGGGATACGTTACAAACACTGGTGAGATTTCCGGTTCCATCACTTGT | | | | |
| TTGCAGAATGGTTGGTCCCCACAGCCATCTTGTATTAAGTCCTGTGACATGCCAGTTTTC | | | | |
| GAGAACTCCATCACTAAGAACACTAGAACATGGTTCAAGTTGAACGACAAGTTGGACTAC | | | | |
| GAGTGTTTGGTTGGTTTCGAGAACGAGTACAAGCACACTAAGGGTTCCATCACATGTACT | | | | |
| TACTACGGTTGGTCTGACACTCCATCCTGTTACGAAAGAGAGTGTTCCGTTCCAACTTTG | | | | |
| GACAGAAAGTTGGTTGTTTCCCCAAGAAAAGAGAAGTACAGAGTTGGAGACTTGTTGGAG | | | | |
| TTCTCTTGTCACTCTGGTCATAGAGTTGGTCCAGACTCCGTTCAATGTTACCACTTTGGA | | | | |
| TGGTCCCCAGGTTTTCCAACTTGTAAGGGTCAGGTTGCTTCTTGTGCCTCCACCATTGGAG | | | | |
| ATTTTGAACGGTGAGATCAACGGTGCTAAGAAGGTTGAATACTCCCACGGTGAAGTTGTT | | | | |
| AAGTACGACTGTAAGCCAAGATTCTTGTTGAAGGGTCCAAACAAGATCCAATGTGTTGAC | | | | |
| GGTAACTGGACTACTTTGCCAGTTTGTATCGAGGAAGAAAGAACTTGCGGAGACATCCCA | CAA | CAA | CAA | N-Q |
| GAATTGGAACACGGTTCCGCTAAGTGTTCTGTTCCACCATACCACCATGGTGATTCCGTT | | | | |
| GAGTTCATCTGTGAG*GAAAA*CTTCACTATGATCGGTCACGGTTCCGTTTCTTGTATTTCC | CAA | GAGTAG | GAGTAG | EN-EQ or EAmb |
| GGTAAGTGGACTCAGTTGCCAAAGTGTGTTGCTACTGACCAGTTGGAGAAGTGTAGAGTT | | | | |
| TTGAAGTCCACTGGTATCGAGGCTATCAAGCCAAAGTTGACTGAGTTCACTCAACTCC | CAG | CAGTCT | CAG | NS-QS |
| ACTATGGACTACAAATGTAGAGACAAGCAAGAGTACGAGAGATCCATCTGTATCAACGGT | | | | |
| AAATGGGACCCAGAACCAAACTGTACTTCCAAGACTTCTTGTCCACCACCACCACAAATT | CAA | CAA | CAA | N-Q |
| CCAAACACTCAGGTTATCGAGACTACTGTTAAGTACTTGGACGGTGAGAAGTTGTCCGTT | | | | |
| TTGTGTCAGGACAACTACTTGACTCAAGACTCCGAAGAGATGGTTTGTAAGGACGGTAGA | | | | |
| TGGCAATCTTTGCCAAGATGTATCGAGAAGATCCCATGTTCTCAGCCACCAACTATTGAG | | | | |
| CACGGTTCCATTAACTTGCCAAGATCCTCCGAAGAAAGAAGAGACTCCATCGAATCCTCT | | | | |
| TCTCACGAACACGGTACTACTTTCTCTTACGTTTGTGATGACGGTTTCAGAATCCCAGAA | | | | |
| GAGAACAGAATCACTTGTTACATGGGAAAGTGGTCCACTCCACCTAGATGTGTTGGTTTG | | | | |
| CCATGTGGTCCACCACCTTCTATTCCATTGGGTACTGTTTCTTTGGAGTTGGAGTCCTAC | | | | |
| CAACACGGTGAAGAGGTTACTTACCACTGTTCCACTGGTTTCGGTATTGATGGTCCAGCT | | | | |
| TTCATTATCTGTGAGGGTGGTAAGTGGTCTGATCCACCTAAGTGTATTAAGACTGACTGT | | | | |
| GACGTTTTGCCAACTGTTAAGAACGCTATCATCAGAGGTAAGTCCAAGAAGTCCTACAGA | | | | |
| ACTGGAGAGCAGGTTACTTTCAGATGTCAGTCCCCATACCAAATGAACGGTTCCGACACT | CAA | CAA | TAG | N-Q or Amber |
| GTTACTTGTGTTAACTCCAGATGGATCGGTCAACCAGTTTGTAAGGATAACTCCTGTGTT | | | | |
| GATCCACCACATGTTCCAAACGCTACTATCGTTACTAGAACTAAGAACAAGTACTTGCAT | CAA | CAA | CAA | N-Q |
| GGTGACAGAGTTAGATATGAGTGTAACAAGCCATTGGAGTTGTTCGGTCAAGTTGAGGTT | | | | |
| ATGTGTGAGAACGGTATCTGGACTGAGAAGCCAAAGTTGTAGAGACTCCACTGGTAAGTGT | | | | |
| GGTCCTCCACCACCAATTGACAACGGTGACATCACTTCTTTGTCCTTGCCAGTTTACGAA | | | | |
| CCTTTGTCCTCCGTTGAGTACCAATGTCAGAAGTACTACTTGTTGAAAGGTAAGAAAACT | | | | |
| ATCACTTGTACTAATGGTAAATGGTCCGAGCCACCAACTTGTTTGCACGCTTGTGTTATC | | | | |
| CCAGAGAACATCATGGAATCCCACAACATCATCTTGAAGTGGAGACACACTGAGAAGATT | | | | |
| TACTCTCACTCCGGTGAGGACATTGAGTTCGGTTGTAAGTACGGTTACTACAAGGCTAGA | | | | |
| GACTCTCCACCATTCAGAACTAAGTGTATCAACGGAACTATCAACTACCCAACTTGTGTT | CAA | CAA | CAA | N-Q |
| TAATGAGCGGCCGCTTAATTAA | | | | |

Constructs 8, 9 and 10 are identical to 7 except where indicated by bold, *italic* or underline in which case the replacement codon is indicated by a footnote or by letters in matching format (bold or italics).
* Resultant changes in amino acid residue sequence
a Entire underlined sequence replaced with the following sequence:

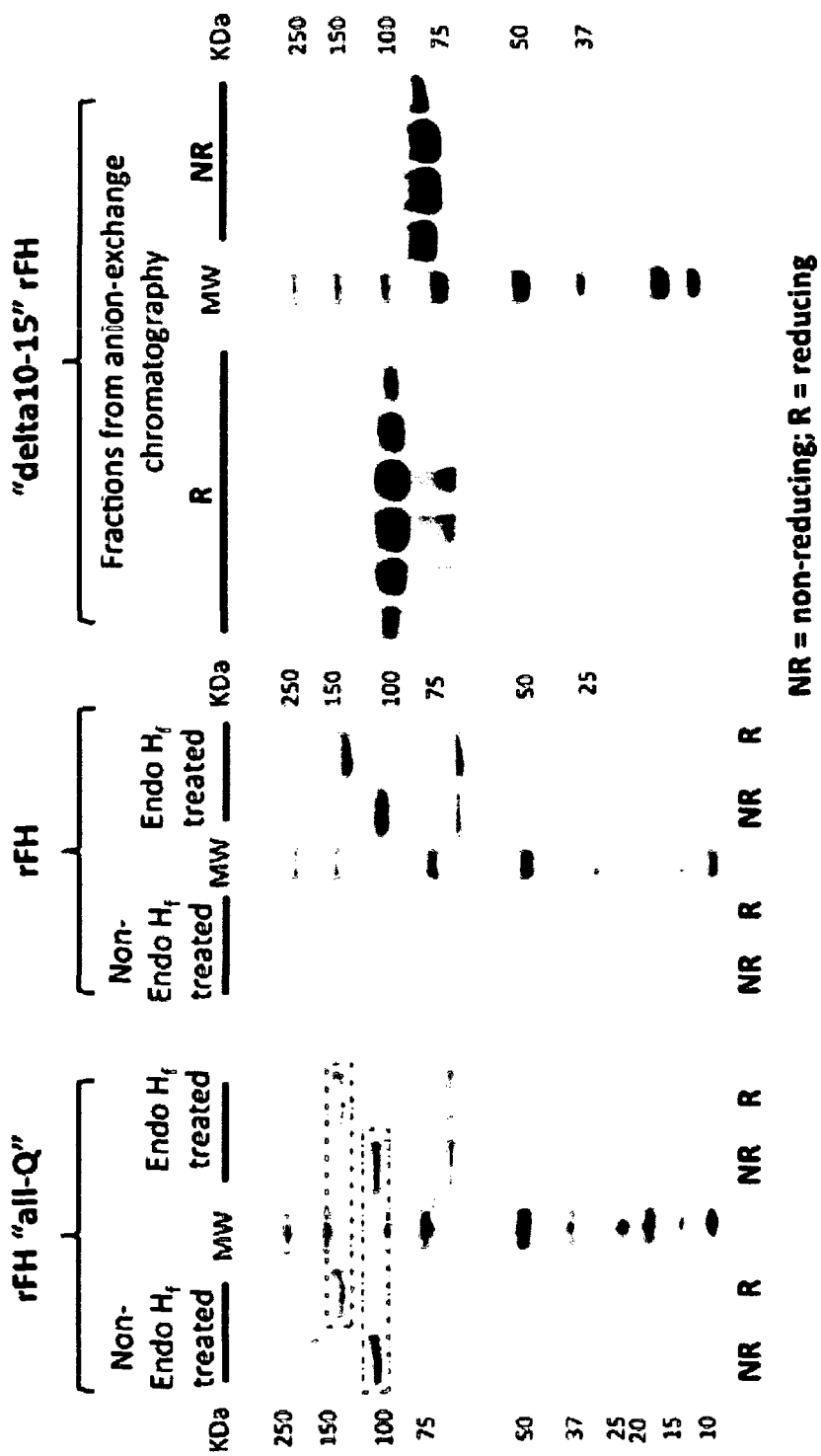
Figure 6: Polyacrylamide gel electrophoresis illustrating production of "all Q" and "delta10-15" mutants of rFH

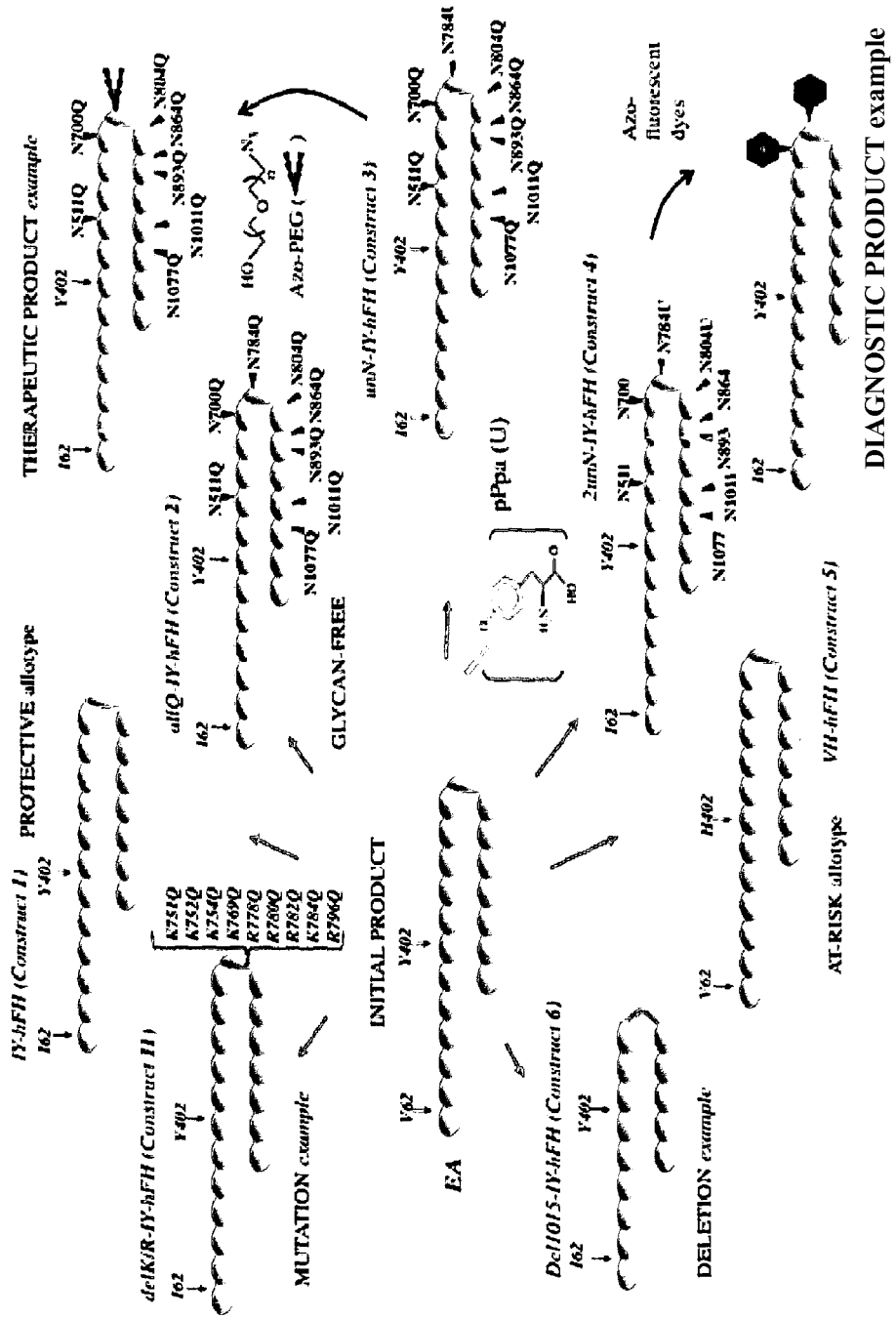
Figure 7: A schematic summary of a route to therapeutic versions of FH

RECOMBINANT CODON OPTIMISED FACTOR H

CROSS-REFERENCE TO RELATED APPLICATIONS

This application is a U.S. national counterpart application, filed under 35 U.S.C. §371, of International Application Serial No. PCT/GB2010/002334, filed Dec. 23, 2010, which claims priority to United Kingdom Patent Application Serial No. 0922659.8, filed Dec. 24, 2009, the disclosures of both of which applications are hereby incorporated herein by reference in their entirety.

FIELD OF THE INVENTION

The present invention relates to recombinant factor H and variants and conjugates thereof and methods of their production, as well as uses and methods of treatment involving said materials.

BACKGROUND OF THE INVENTION

An increasing body of evidence suggests that the complement system regulatory glycoprotein, factor H (FH), if produced in sufficient quantities and endowed with appropriate pharmacokinetic and pharmacodynamic properties, would serve as a new biotherapeutic agent. This agent could prevent development of age-related macular degeneration (AMD) in genetically susceptible individuals and facilitate treatment in those with AMD and two life-threatening kidney conditions known as atypical haemolytic uraemic syndrome (aHUS) and dense deposit disease (DDD). More speculatively, this agent could have beneficial effects in the treatment or prevention of numerous other diseases in which inadequate complement regulation contributes to aetiology or symptoms.

However current attempts to produce FH through overexpression of a gene in recombinant cells have failed to yield the quantities that would be required for therapy, while purification from human plasma of sufficient quantities of the appropriate variants of FH has logistical and technical difficulties and carries health risks. There are urgent unmet clinical and commercial needs for multiple-gram quantities of biotherapeutic-grade recombinant versions of FH with minimal immunogenicity, an extended half-life and maximal efficacy.

Links between polymorphisms in FH and susceptibility to disease have been well documented and are reviewed, for example in: Opportunities for new therapies based on the natural regulators of complement activation. Brook E, Herbert A P, Jenkins H T, Soares D C, Barlow P N. *Ann NY Acad Sci* 2005 1056:176-88; Complement factor H: using atomic resolution structure to illuminate disease mechanisms. Barlow P N, Hageman G S, Lea S M. *Adv Exp Med Biol.* 2008 632:117-42; Translational mini-review series on complement factor H: renal diseases associated with complement factor H: novel insights from humans and animals. Pickering M C, Cook H T. *Clin Exp Immunol* 2008 151:210-30; Translational mini-review series on complement factor H: genetics and disease associations of human complement factor H. de Córdoba S R, de Jorge E G. *Clin Exp Immunol.* 2008 151:1-13.

Since these reviews were published numerous further published findings have broadened the scope of potential targets for FH-based therapies. Two recent examples establish an association between the FH gene (CFH) polymorphism (Y402H) and susceptibility to cardiovascular disease (CVD). Koeijvoets et al. (Complement factor H Y402H decreases cardiovascular disease risk in patients with familial hypercholesterolaemia. Koeijvoets K C, Mooijaart S P, Dallinga-Thie G M, Defesche J C, Steyerberg E W, Westendorp R G, Kastelein J J, van Hagen P M, Sijbrands E J. *Eur Heart J.* 2009 30:618-23. showed that amongst patients with severely increased risk of early-onset CVD due to hypercholestrolaemia, the Y402 CFH variant was inversely associated with susceptibility to CVD suggesting that CFH modifies the risk of CVD. In a study by Buraczynska et al. (Complement factor H gene polymorphism and risk of cardiovascular disease in end-stage renal disease patients. Buraczynska M, Ksiazek P, Zukowski P, Benedyk-Lorens E, Orlowska-Kowalik G. *Clin Immunol.* 2009; 132:285-90) of end-stage renal failure in patients on dialysis, multivariate logistic regression analysis showed that the Y402H genotype is independently associated with cardiovascular co-morbidity; with homozygosity for the H402 allele being associated with an odds ratio of 7.28 (95% CI 5.32-9.95). In another recent development, Moreno-Navarrete et al. (Complement Factor H is expressed in adipose tissue in association with insulin resistance. Moreno-Navarrete J M, Martínez-Barricarte R, Catalán V, Sabater M, Gómez-Ambrosi J, Ortega F J, Ricart W, Blüher M, Frühbeck G, de Cordoba S R, Fernández-Real M J. *Diabetes* 2009: Epub Oct. 15) showed that FH is expressed in adipose tissue in association with insulin resistance, suggesting a link between the alternative pathway of the complement system, obesity and metabolic disorders.

Data for the likely efficacy of FH in treatment is already very strong, and has precipitated numerous disclosures, patent applications and company start-ups. US2007/0020647 discusses the expression of human CFH in a variety of eukaryotic and prokaryotic protein-overproduction vectors and in mammalian cell lines, but only explicitly exemplifies expression in the human lung carcinoma cell line A549. The quantities of recombinant protein obtained from this cell line are not disclosed, but based on precedent and in the absence of any evidence to the contrary the amounts are expected to be inadequate for therapeutic purposes. WO2007/038995 describes the use of human factor H to treat aHUS. The patent application mentions the use of recombinant FH without providing significant details about the methods of production of recombinant FH, but is focused on purification of FH from human plasma.

Thus although the above two documents disclose the idea of using recombinant FH therapeutically, neither document actually teaches the large-scale production of recombinant FH that is absolutely essential for its therapeutic application; as shown herein, this is not a straightforward task.

Successful manufacture of larger amounts (greater than 10 mg) of pure recombinant full-length FH with preserved functional activities has not previously been reported in the scientific or patent literature. Indeed, in the limited data supporting the patents discussed above, the authors demonstrated capability of producing only minute quantities (less than about 1 mg) of recombinant FH and did not provide evidence that they had purified or characterised this material. Furthermore, literature reports likewise allude to sub-milligram quantities of recombinant FH from insect and mammalian cells (e.g. Biologically active recombinant human complement factor H: synthesis and secretion by the baculovirus system. Sharma A K, Pangburn M K. *Gene* 1994 143:301-2; Structural and functional characterization of factor H mutations associated with atypical hemolytic uremic syndrome. Sánchez-Corral P, Pérez-Caballero D, Huarte O, Simckes A M, Goicoechea E, López-Trascasa M, de Córdoba S R. *Am J Hum Genet* 2002 71:1285-95.) or to expression of fragments, only, of the FH molecule (e.g. Structure of the N-terminal region of complement factor H and conformational implications of disease-linked sequence variations. Hocking H G, Herbert A P, Kavanagh D, Soares D C, Ferreira V P, Pangburn M K, Uhrin D, Barlow P N. *J Biol Chem* 2008 283:9475-87).

Ormsby, R. J. et al., Expression of human factor H in the methylotrophic yeast *Pichia Pastoris*. Molecular Immunology Vol 35, p. 353, 1998 Abstract 92. This paper uses a *Pichia pastoris* production system to express a FIVE (5) complement control protein (CCP) fragment of Factor H, not the full length TWENTY (20) CCP Factor H protein, which is the subject of present patent application.

Ripoche, J. et al., The complete amino acid sequence of human complement Factor H. Biochemical Journal, Vol 249: 593-602, 1988. This paper describes the full length human factor H nucleotide sequence (and hence the amino acid sequence) and was obtained by sequencing three overlapping cDNA clones spanning the Factor H gene. However, it does not describe how to clone the gene such that it is possible to express functional human Factor H protein.

EP1336618 describes using full length or fragments of porcine Factor H as a soluble complement regulator, for use as a therapeutic. It is suggested that porcine factor H could be purified from pig plasma or as exemplified in this patent, made recombinantly using Baculovirus. However, no quantification of the amount of full length porcine factor H from a standard fermentation nor any functional data for the full length protein (rather than only fragments) is shown. However, there is no disclosure or teaching of how to express functional human Factor H.

The use of porcine Factor H naturally carries the risk of infection with cross-species zoonotic infections. Moreover, there is not complete DNA sequence or amino acid homology between human factor H and porcine factor H (62% homology Hegasy G. A. et al., Pig complement regulator factor H: molecular cloning and functional characterization. Immunogenetics. 2003 October; 55(7):462-71). It is therefore very likely autoantibodies to porcine Factor H would be made, which would again limit therapeutic usage.

WO 2008/135237 describes use of a therapeutic which combines a short consensus repeat (SCR) of Factor H with a pathogen recognition binding molecule e.g. an antibody. It specifically mentions use of fragments/peptide chains of less than 100 amino acids (<2 SCRs). It does not suggest use of a full length Factor H molecule with a pathogen recognition binding molecule. Also, its focus is for the use of treating infections or for cancer, not renal or opthalmological diseases.

Currently, FH-replacement clinical therapy is achieved by means of infusing donated pooled plasma, of which FH is only one of many protein components. It is not possible clinically to routinely obtain plasma containing only the FH Y402 allotype (which is protective against AMD); when purified in bulk from pooled plasma, FH is heterogeneous in terms of both its heterotypic and glycoform variations and hence this material is ill-suited for therapy; antibody-affinity based purification methods generally yield only small amounts (a few mg at most) of material that can be enriched only for a single variant at a specific site of variation (e.g. for Y402) but will be heterogeneous with respect to other polymorphic sites (e.g. V62I). Any use of plasma-purified human proteins would in any case may carry unacceptable risks, of infection with both unknown viral and prion proteins, and of sensitisation to contaminating plasma components, when used on the repetitive basis proposed for AMD, aHUS and DDD therapies.

It is therefore amongst the objectives of the present invention to obviate and/or mitigate at least one of the aforementioned obstacles to therapeutic use of FH.

SUMMARY OF THE INVENTION

The invention is based on work carried out by the present inventors towards providing high-yield production of versions of FH tailored for animal and human trials and therapeutic applications, which is based on the use of codon-optimised chemically synthesised genes that are transfected into, for example and preferably, *Pichia pastoris* followed by expression in a fermentor and purification using a sequence of chromatographic procedures.

In a first aspect there is provided a process for making recombinant mammalian FH, said process comprising the steps of:

expressing in a chosen host organism a codon-optimised nucleic acid sequence which encodes said mammalian FH or variants thereof and which nucleic acid sequence has been codon optimised for expression in a chosen host organism and inserted into an appropriately designed vector; in order to obtain said mammalian FH or variants thereof.

Conveniently, the codon-optimised nucleic acid sequence can initially be chemically synthesised rather than cloned and mutagenised in order to generate the necessary codon optimisation. In accordance with the present invention it is possible to produce large quantities of recombinant mammalian FH and its variants hitherto not possible using the previously described techniques. Typically the methods of the present invention may produce protein yields of at least 0.5 mg of recombinant FH (or its variants) per liter of culture medium, such as at least 1 mg, 5 mg, 10 mg, 50 mg, 100 mg, 200 mg or 500 mg per liter of culture medium. It will therefore be appreciated that it is possible following the methods of the present invention, when using industrial-scale fermentors, to produce hundreds of milligrams or gramsoreven kilogram-quantities of recombinant FH and variants thereof, which was simply not possible using conventionally cloned recombinantly expressed FH.

The above process may further comprise purifying said proteins from the cell and/or culture medium in which the cell is grown. Purification may typically involve the use of chromatographic methodologies, such as fast-protein liquid chromatographic or high-performance (pressure) liquid chromatographic techniques known in the art. For example, the nucleic-acid sequence may be designed to encode a secretion-signal sequence of amino-acid residues fused to the N-terminus of FH so that FH is secreted into the media (whereupon said signal-sequence peptide is cleaved off) and thereby it is separated from intracellular *P. pastoris* proteins at the outset. In a subsequent purification step, crude material may, for example, be loaded onto an affinity chromatography column, such as a heparin-sepharose column equilibrated in phosphate-buffered saline (PBS), and eluted by application of a gradient, over multiple column volumes, to PBS substituted with high salt (e.g. 1 M NaCl); in a further step, FH-containing fractions from the previous step may be loaded onto, for example, an ion-exchange resin-containing column, such as a GE Healthcare-supplied MonoQ column that has been equilibrated in 20 mM glycine buffer (typically pH 9.5, 150 mM NaCl), and then eluted with a gradient, over many column volumes, with the equilibration buffer at the same pH but substituted with high salt (e.g. 1 M NaCl).

The preferred choice of host organism is *Pichia pastoris* on the grounds that no re-folding of the expressed protein is required, the protein may be secreted into the media and therefore easily accessible, and specific glycoconjugates or non-natural amino acid residues may be incorporated into the recombinant product; but other prokaryotic (e.g. *Escherichia coli*) and eukaryotic (e.g. *Sacchyromyces cerevisiae*) host organisms may also be envisaged.

The mammalian FH referred to may be human FH or FH from another primate or other mammalian FH, such as that from mouse, rat, hamster, rabbit, dog, horse, cow, pig, sheep, camel, cat, guinea pig, or the like.

The deoxyribonucleic nucleic acid (DNA) sequence may comprise unique restriction endonuclease sites at the 5' and 3' ends of the nucleic acid, to facilitate cloning into an appropriately restricted expression vector. Preferred restriction sites are PstI, BamHI, NotI and XbaI, although others may easily be envisaged by the skilled addressee.

The nucleic acid sequence encoding FH may relate to one of a number of wild-type sequences (known in the art as polymorphic variants) or may be a mutant sequence. The sequence may comprise one or more single-nucleotide polymorphisms known in the art. US 2007/0020647, for example, describes many polymorphisms that have hitherto been identified in the human CFH (the contents of which are hereby incorporated by way of reference) and more such polymorphic variants may be discovered in the future; one or more of these may readily be incorporated into the codon-optimised nucleic acid sequence. Preferred single-nucleotide polymorphisms that may be incorporated, individually or in combination, into the codon-optimised nucleic acid sequence could code for the following variations in the protein sequence: Ile62 (rather than Val), Tyr402 (rather than His), Glu936 (rather than Asp) and/or Arg1210 (rather than Cys) (all numbers refer to the sequence of the encoded protein prior to cleavage of the signal sequence (Swiss-Prot: P08603.4)). Such single-nucleotide polymorphisms and haplotypes have been reported to be associated with a lower-than-average risk of developing AMD (Hageman G S et al., A common haplotype in the complement regulatory gene factor H(HF1/CFH) predisposes individuals to age-related macular degeneration. *Proc Natl Aced Sci USA* 2005 102:7227-32; Klein R J et al. Complement factor H polymorphism in age-related macular degeneration. *Science.* 2005 308:385-9; Edwards A O et al. Complement factor H polymorphism and age-related macular degeneration. *Science* 2005 308:421-4; Haines J L et al. Complement factor H variant increases the risk of age-related macular degeneration. *Science* 2005 308:419-21; Hageman G S et al. Extended haplotypes in the complement factor H(CFH) and CFH-related (CFHR) family of genes protect against age-related macular degeneration: characterization, ethnic distribution and evolutionary implications. *Ann Med* 2006 38:592-604). Alternatively or additionally, mutant sequences may be designed to specifically alter the FH polypeptide sequence, for example to include one or more natural (encoded) or non-naturally encoded variant amino acids as described in more detail herein below.

The conjugate refers to a molecule that consists of a polypeptide corresponding to FH or a variant of FH to which is covalently attached, normally via one or more amino-acid residue side-chains, to a chemical moiety or moieties intended to improve the biotherapeutic properties of said molecule. The attached moieties could include: natural polymers such as glycosaminoglycans and their derivatives or polysialic acids, dextran (−1,6 polyglucose), dextran (−1,4 polyglucose), hyaluronic acid, and chitosans; unnatural polymers such as any of a large family of linear or branched polyethylene glycols, polyether polyols, N-(2-hydroxypropyl) methacrylamide copolymers, poly(vinylpyrrolidone), poly(ethyleneimine), or linear polyamidoamines; or pseudo-synthetic polymers, such as poly(L-lysine), poly(glutamic acid), poly(malic acid) and poly(aspartamides) (see for example The dawning era of polymer therapeutics. Duncan R. *Nature Reviews Drug Discovery* 2003 2:347-360).

Rather than conventional gene cloning and expression, the present invention is based on an initial chemical synthesis of the codon-optimised DNA molecules encoding said FH (and variants thereof), using gene design and synthesis techniques in the art (e.g. Gene composer: database software for protein construct design, codon engineering, and gene synthesis. Lorimer D, Raymond A, Walchli J, Mixon M, Barrow A, Wallace E, Grice R, Burgin A, Stewart L. *BMC Biotechnol.* 2009 9:36). In this manner, the codon-optimised nucleic acid is synthesised de novo prior to cloning into a suitable expression vector. Conventional site-directed mutagenesis techniques known in the art to carry out codon optimisation of the FH gene would be unfeasibly time-consuming, if not impossible due to the high risk of introducing additional mutational variations during the requisite repeated rounds of site-directed mutagenesis. However, site-directed mutagenesis may be used following cloning of the synthetic codon-optimised CFH, in order to accomplish one or a combination of site-specific mutations in the product Codon optimisation is carried out in order to enhance the expression levels of the mammalian FH and its variants in the desired host organism, such as *P. pastoris*. Said optimisation involves one or more of the following: adapting codon bias to match that of the chosen host organism; avoiding regions of high (>80%) or low (<30%) GC content; minimising any potential internal TATA boxes, chi-sites and ribosome-entry sites; minimising AT-rich or GC-rich stretches of sequence, avoiding repeat sequence and RNA secondary structures, minimising any (cryptic) splice-donor and/or splice-acceptor sites; and ensuring any desired restriction endonuclease sites are only found at the extreme 5' and 3' ends of the nucleic acid to facilitate cloning. Preferably all of the above considerations are taken into account when optimising the nucleic acid sequence. The skilled addressee is able to make such modifications to the original FH sequence based on prior knowledge in the art in relation to the codon bias of the chosen host and other teachings (e.g. Codon bias and heterologous protein expression. Gustafsson C, Govindarajan S, Minshull J. *Trends Biotechnol* 2004 22:346-53). Certain companies such as Geneart (Regensburg, Germany), GeneScript (Piscataway, N.J., USA) and DNA2.0 (Menlo Park, Calif., USA) provide a service for optimising and synthesising nucleic acid sequences that are tailored for expression in a specified host organism.

In a preferred embodiment, the DNA sequence encoding mammalian FH is a CFH sequence which has been optimised for expression in the host, *P. pastoris*. A *P. pastoris* codon-optimised human CFH sequence (encoding for Y at position 402, I at position 62 and E at position 936) is compared to the wild-type cDNA sequence in FIG. 1. It will be appreciated that this codon-optimised sequence may be varied in order to still further optimise the sequence for overproduction in *P. pastoris*. Moreover, the sequence may be easily varied in order to allow for expression of various allotypes. Moreover, certain nucleotide bases may be changed in order to specifically alter the amino-acid residue sequence of the FH protein. For instance, certain amino-acid residues may be replaced with, for example, alternative amino-acid residues that may be rare or non-naturally occurring amino-acid residues, so as to allow for the generation of recombinant FH proteins with one or even a combination of modifications leading to: altered glycosylation patterns; reduced immunogenicity; enhanced plasma half-life; and/or site-specific conjugation with moieties designed to improve pharmacokinetic and/or pharmacodynamic properties. It will be appreciated that all such modifications can be carried out whilst taking account of any codon optimisation considerations.

Thus, in a further aspect, the present invention provides a nucleic acid sequence capable of expressing a FH polypeptide or variant thereof, the nucleic acid sequence being codon optimised for expression in a host organism, such as *P. pastoris*. There is also provided a mammalian FH polypeptide or variant thereof, obtained from a nucleic acid sequence according to the present invention.

Preferably the sequence is codon optimised for expression by *P. pastoris*, in which case the nucleic acid sequence may be the codon-optimised human sequence shown in FIG. 1 or any of the sequences represented in FIG. 5, or be substantially similar to them. By substantially similar is understood that the sequence is greater than 70%, 75%, 80%, 85%, 90%, 95% or even 99% identical to the sequence shown in FIG. 1 or 5.

The present invention also relates to vectors which include a codon-optimised FH-encoding DNA sequence of the present invention, host cells which are genetically engineered with said recombinant vectors, and the production and purification of the encoded FH and FH-like polypeptides by recombinant techniques, and the conjugated products of said polypeptides.

Recombinant constructs may be introduced into host cells using well-known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides of interest may be contained within a vector containing a selectable marker for propagation in a host. Generally, a plasmid vector is introduced in the form of a precipitate, such as a calcium phosphate precipitate, or in a complex with a charged lipid. If the vector is a virus, it may be packaged in vitro using an appropriate packaging cell line and then transduced into host cells.

Preferred, are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression and may be inducible and/or cell type-specific. Suitable vectors include those inducible by environmental factors that are easy to manipulate, such as temperature and nutrient additives.

Expression vectors useful in the present invention include chromosomal-, episomal- and virus-derived vectors, for example vectors derived from bacterial plasmids, bacteriophages, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter. Known bacterial promoters suitable for use in the present invention include the *E. coli* lacI and lacZ promoters, the T3 and T7 promoters, the gpt promoter, the phage lambda $P_R$ and $P_L$ promoters and the tac and trp promoter. Suitable eukaryotic promoters include the cytomegalovirus immediate early promoter, the herpes simplex virus thymidine kinase promoter, the early and late SV40 promoters, the promoters of retroviral long terminal repeats (LTRs), such as those of the Rous sarcoma virus and metallothionein promoters, such as the mouse metallothionein-I promoter. Promoters specific to *P. pastoris* include alcohol oxidase 1 (AOX1), AOX2 (both methanol inducible), CUP1 (copper inducible), GAP (glycerol inducuble, constitutively active on various carbon sources), FLD1 (formaldehyde dehydrogenase gene) PEX8 (moderate promoter) YPT1 (moderate promoter, constitutively active on various carbon sources) DAS1 (dihydroxyacetone synthase) ADH1 (alcohol dehydrogenase) and PGK1 (3-phosphoglycerate kinase). Other suitable promoters will be known to the skilled artisan, see for example Cereghino and Cregg, 1999, Current Opinion in Biotechnology, 10, p 422-427.

The expression constructs will further contain sites for transcription initiation, termination and, in the transcribed region, a ribosome-binding site for translation. The coding portion of the mature transcripts expressed by the constructs will include a translation-initiating AUG at the beginning and a termination codon appropriately positioned at the end of the nucleic acid sequence to be translated. It is facile, using synthetic genes, to optimise all of these features of the insert to maximise gene-expression levels and recombinant-protein yields.

As indicated, the expression vectors will preferably include at least one selectable marker. Such markers include e.g. dihydrofolate reductase or neomycin or zeocin resistance for eukaryotic cell culture and e.g. tetracycline or ampicillin-resistance genes for culturing in *E. coli* and other bacteria.

Representative examples of appropriate hosts include bacterial cells, such as *E. coli, Streptomyces* and *Salmonella typhimurium* cells; fungal cells, such as yeast cells like *P. pastoris, Kluyveromyces lactis* and *Sacchyromyces cerevisiae*; insect cells such as *Drosophila melanogastor* S2 and *Spodoptera frugiperda* 9 cells; animal cells such as Chinese hamster ovary, COS and Bowes melanoma cells; and plant cells. Appropriate culture media and conditions for the above-described host cells are known in the art. Most preferably the host organism is the methylotropic yeast *P. pastoris*. Strains of *P. pastoris* that have been metabolically engineered so that they attach mammalian or human-like N-glycans may be preferred, see Wildt and Gerngross, 2005, Nature Reviews, 3, p 119-128, Li et al, 2006, Nature Biotechnology, 24, p 210-215, Cereghino, et al, 2002, Current Oinion in Biotechnology, 13, p 329-332.

Vectors preferred for use in bacteria include pA2, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Vectors preferred for use in *P. pastoris* include pPIC9K, pHIL-D2, pHIL-S1, pPIC3.5K, pGAPZ, pGAPZalpha, pPICZalpha-A, pPICZalpha-B, pPICZalpha-C, pPICZalpha-E, pPICZalpha-E/Uni, pPIC3.5, pPIC9, pPICZ-A, pPICZ-B, pPICZ-C, pPICZ-E from Invitrogen. Other suitable vectors will be readily apparent to the skilled artisan.

As indicated, introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis L G G et al., Basic Methods in Molecular Biology, ($2^{nd}$ Ed., McGraw-Hill, 1995).

As indicated, transcription of the DNA encoding the polypeptides of the present invention by higher eukaryotes may be increased by inserting an enhancer sequence into the vector. Enhancers are cis-acting elements of DNA, usually from about 10 to about 300 bp that act to increase transcriptional activity of a promoter in a given host cell-type. Examples of enhancers include the SV40 enhancer, which is located on the late side of the replication origin at by 100 to 270, the cytomegalovirus early-promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous. Examples of such sequences that may be used in *P. pastoris* include the native human or mouse (or other mammalian) FH-secretion signals and the yeast alpha-mating factor.

The polypeptide of interest may be expressed in a modified form, such as a fusion protein, and may include not only secretion signals, but also additional heterologous functional regions. Thus, for instance, a region of additional amino-acid residues, particularly charged amino-acid residues, may be added to the N terminus of the polypeptide to improve stability and persistence in the host cell, during purification, or during subsequent handling and storage. Also, peptide moieties may be fused to the polypeptide to facilitate purification. Such regions may be removed prior to final preparation of the polypeptide. Additions of peptide moieties to polypeptides in order to engender secretion or excretion, to improve stability and to facilitate purification, amongst others, are familiar and routine techniques in the art.

The FH protein can be recovered and purified from recombinant cell cultures by well-known methods including ammonium sulphate or ethanol precipitation, acid extraction, anion-exchange or cation-exchange chromatography, phosphocellulose chromatography, hydrophobic-interaction chromatography, affinity chromatography, hydroxylapatite chromatography, reverse-phase chromatography, size-exclusion chromatography and lectin chromatography. Most preferably, heparin-affinity is followed by ion-exchange chromatography.

It will be recognised in the art that the amino-acid residue sequence of aFH polypeptide may be selectively varied without having a significantly detrimental effect on the structural integrity or functional properties of the protein. If such differences in sequence are contemplated, it should be remembered that there are regions of the protein that are critical to its biological activity. There will also be residues that are critical to the folding of the protein or for stabilisation of its folded structure. Some residues serve as glycosylation sites, recognised by enzymes that covalently attach glycans to, for example, Asn side-chains. In general, it may be possible to safely replace residues that contribute directly or indirectly to structure or function by other residues that are chemically similar (this is known as a conservative substitution). In the cases of amino-acid residues that contribute neither to structural integrity nor to functional sites, it may be possible to safely replace such a residue with an amino-acid residue of a different chemical nature (a non-conservative replacement).

Thus, the invention further includes variations of the FH polypeptide which variants show substantially FH-like biological activity. Variants might include conservative substitutions (for example, substituting one hydrophilic residue for another, or one hydrophobic residue for another), but would be unlikely to include replacements of strongly hydrophilic residues for strongly hydrophobic ones (or vice versa). Variants might include conservative substitutions within N-glycosylation sites that result in loss of such sites. Variants may also include deletions of one or more of the 20 protein domains within the FH molecule. For example, deletion of one or a combination of domains [such as 2, 3, 4, 5, 6, 7, 8, 9, 10 or 11 domains] between and including domains 8 and 18 would be unlikely to have a detrimental effect on the functionally critical individual binding sites located in domains 1-4, 6-7 (or 6-8) and 19-20. Variants could also include deletions of one or a combination of domains from the region of FH between and including domains 5-18 since this would preserve C3b-binding sites (1-4, and 19-20) and one (in 19-20) of two cell surface-recognition sites within FH (see e.g. A new map of glycosaminoglycan and C3b-binding sites on factor H. Schmidt C Q, Herbert A P, Kavanagh D, Gandy C, Fenton C J, Blaum B S, Lyon M, Uhrin D, Barlow P N. *J Immunol*, 2008, 181:2610-9) and might enhance functional activity by optimising the spatial positioning, or flexibility of the connection, between these binding sites. Variants might also include hybrids, in which, for example one or more deleted domains from the domains 8-18, or 5-18, regions of FH are replaced with one or more similar domains derived from other proteins, for example from complement receptor type I or type II; alternatively they might be replaced by one or more dissimilar domains derived from a wide range of other proteins such as proteins of the extracellular matrix or the clotting or complement cascades.

Typically seen as conservative substitutions are the replacements, one for another, amongst the aliphatic amino-acids Ala, Val, Leu and Ile; interchange of the hydroxyl residues Ser and Thr; exchange of the acidic residues Asp and Glu; substitution between the amide residues Asn and Gln; exchange of the basic residues Lys and Arg; and replacements amongst the aromatic residues Phe and Tyr. Non-conservative substitutions could include substitutions with both naturally encoded amino-acid residues and a non-naturally encoded (unnatural) amino-acid residue. The unnatural amino-acid residue could be one that serves as a site-specific attachment sites for conjugation with chemical moieties (such as polyethylene glycols (PEGs) and other polymers), or with biochemical groups (such as glycans) that enhance the therapeutic efficacy of FH.

As indicated in detail above, further guidance concerning which amino acid changes are likely to be phenotypically silent (i.e. are not likely to have a significant deleterious effect on a function) can be found in Bowie, et al., "Deciphering the Message in Protein Sequences: Tolerance to Amino Acid Substitutions," *Science* 247:1306-1310 (1990).

Also of interest are substitutions that prevent aggregation or minimise proteolysis. Aggregation of proteins not only results in a loss of activity but can also be problematic when preparing pharmaceutical formulations, because aggregates can be immunogenic (see, e.g. Pinckard et al., *Clin Exp. Immunol*, 1967, 2:331-340; Robbins et al., *Diabetes*, 1987, 36:838-845; Cleland et al., *Crit. Rev. Therapeutic Drug Carrier Systems*, 1993, 10:307-377). Aggregation may be minimised by changing surface residues, for example removing hydrophobic patches (by substituting hydrophobic residues with polar ones) or by changing the electrostatics at the surface by charge-reversal (e.g. by substituting Asp for Arg or Glu for Lys) or deletion (e.g. substituting Ser for Asp). Proteolysis results in a loss of the target protein thus lowering yield and also makes purification more difficult. Proteolysis may be reduced by recognition of proteolytic sites via computational prediction or empirical means and conservative substitutions therein.

Possible modifications of particular relevance to mammalian FH include mutating one or more Asn residues to Gln residues in order to minimise glycosylation of the FH protein. Alternatively one or even two Asn residues of the FH protein may be replaced by any of a large number of unnatural amino-acid residues, such as p-(propargoxy)-phenylalamine (pPpa) residues (Expanding the genetic repertoire of the methylotrophic yeast *Pichia pastoris*. Young T S, Ahmad I, Brock A, Schultz P G. *Biochemistry* 2009 48:2643-53). Such an unnatural residue could be further modified by PEGylation or sialylation techniques known in the art.

Thus, in a further aspect, the present invention provides a recombinantly expressed variant of mammalian, especially human, FH obtained from a codon-optimised nucleic acid wherein the variation comprises one or more amino-acid residue substitutions designed to modulate one or more biological properties of said FH variant as compared to a native FH.

It will be understood that said amino acid substitution(s) do not relate to polymorphic changes to the FH protein, as known in the art. Said substitution(s) may result in modulation of, for example, immunogenicity and/or a physiological property of said FH variant as compared to a native FH. Exemplar modifications include substituting one or more Asn residues for another amino acid residue, such as Gln, or a non-naturally occurring amino acid residue, such as pPpa, in order to vary the glycosylation state of said FH variant and/or allow further modification of said FH variant using chemistry known in the art in order to allow the variant to be specifically modified at said substituted sites by a molecule such as PEG or polysialyl chains.

Thus, the target FH-like polypeptide may be: (i) one in which one or more of the amino acid residues are substituted with a conserved or non-conserved amino acid residue and such substituted amino acid residue may or may not be one encoded by the genetic code; or (ii) one in which one or more of the amino acid residues is conjugated with another molecule or includes a substituent group; or (iii) one in which the mature polypeptide may be covalently linked to another compound or compounds, such as a compound to increase the half-life of the polypeptide (for example, PEG or polysialic acid); or (iv) one in which additional amino acid residues are fused to the mature polypeptide, such as an IgG Fc fusion-region peptide or leader or secretion-signal sequence or a sequence which is employed for purification of the mature polypeptide or a pro-protein sequence; or (v) one with an altered (compared to the native glycoforms of FH) pattern of attached glycans due to substitutions within glycosylation sites or introduction of new glycosylation sites (or unnatural amino acids suitable for chemical conjugation with glycans) or employment of strains of *P. pastoris* with engineered glycosylation pathways; or (vi) domain-deletion or hybrid variants in which domains have been removed from the central portion of FH and may or may not have been substituted with homologous or other domains from other proteins. Such fragments, derivatives, conjugates and analogues are deemed to be within the scope of those skilled in the art from the teachings herein.

The recombinantly expressed mammalian FH polypeptides and variants of the present invention may find a variety of applications. For example the polypeptides/variants may be used therapeutically to treat or prevent age-related macular degeneration (AMD) or to prevent or slow the progression of this disease, in genetically susceptible individuals and facilitate treatment in those with AMD, as well as in the treatment/prevention of two life-threatening kidney conditions known as atypical haemolytic uraemic syndrome (aHUS) and dense deposit disease (DDD). The recombinantly expressed mammalian FH of the present invention could have beneficial effects in the treatment or prevention of numerous other diseases or pathologies in which inadequate complement regulation contributes to aetiology or symptoms, for example Alzheimer's disease, ischemia, pre-eclampsia, early pregnancy loss, sepsis, multiple sclerosis, system lupus erythematosus and transplant rejection. See for example, Ischaemia-Reperfusion Injury: (Shah K G et al, *J Surg Res.* 2010 163 1:110-117; Yang J et al, *Ann Surg.* 2009 249 2:310-317; Zhang F et al, *Regul Pept.* 2009 8 52(1-3):82-87, Organ Transplantation: Atkinson C, at al, *J Immunol.* 2010 185 11:7007-7013., Early Pregnancy Loss: Lynch A M, et al, *Obstet Gynecol.* 2011 117 1:75-83 and Pre-eclampsia Qing X et al, *Kidney Int.* 2010 Oct. 13. [Epub ahead of print].

The recombinant FH polypeptides and variants in accordance with the present invention may also find application in research and also in kits and the like.

Particularly preferred FH molecules and variants according to the present invention are described in detail below.

DETAILED DESCRIPTION

The present invention will now be further described by way of example and with reference to the figures which show:

FIG. 1 shows DNA sequence (Swiss-Prot: P08603.4) of native human FH; Sequence of *P. pastoris* codon-optimised human FH of the present invention; and an alignment of the wild-type (cDNA-derived) and codon-optimised FH gene sequences.

FIG. 2 shows western-dot-blot results from non-codon optimised FH gene expression.

FIG. 3 shows production and characterisation of recombinant complement factor H:

A—Elution from an anion-exchange column (MonoQ) ($A^{280}$ in milli-absorbance units on left-hand y-axis) with a salt gradient (20 mM glycine buffer, pH 9.5, 0.12-1 M NaCl; conductivity on right-hand y-axis).

B—Fractions eluted from the MonoQ column (see FIG. 3A) were subjected to SDS-PAGE and protein bands were visualised with Coomassie blue. Lanes 1-8 (reducing conditions—i.e. no disulfides present) correspond to elution volumes 23-30. No significant "clipping" of the polypeptide chain is evident. Lane 9 contains molecular weight markers (MW) as indicated on the right-hand side. Lanes 3',4' and 5' correspond to lanes 3, 4 and 5 but were run under non-reducing conditions; the faster migration of bands in lanes 3',4', and 5' (compared to lanes 3, 4 and 5) is typical for proteins that contain disulfide bonds.

C—Two antibodies that recognise epitopes within the C-terminal CCP modules (domains) of FH, were used in western blots. Plasma FH (left lane) andrecombinant rFH (middle lane) were detected with (i) MAb-SC47686_L20/3 or (ii) Mab-Abnova-0167. MW=molecular weight markers—see right-hand side of gel (ii).

D—The abilities of FH (lanes 1-5) and rFH (lanes 7-11) to act as cofactors for factor I-catalysed cleavage of C3b to iC3b were assessed by visualising the 43-kDa and 68-kDa proteolytic fragments of the α'-chain using SDS-PAGE followed by Coomassie blue staining. Incubation times were 0 to 30 minutes, as indicated. Both versions of FH have similar activities in this semi-quantitative assay such that the α'-chain of C3b is completely processed within five minutes. MW=molecular weight markers of (from top) 250, 150, 100, 75, 50, 37, 25 and 20 kDa.

E—For comparison with FIG. 3D, the cofactor activity of soluble complement receptor type 1 (sCR1), at the same concentration was followed over the same time intervals. Note that (in agreement with literature) sCR1, but (from FIG. 3D) neither rFH nor plasma-purified FH, promoted the further degradation of the α'-chain to C3dg and a 30-kDa fragment. MW, as in FIG. 3D.

F—Surface plasmon resonance was used to monitor formation of the C3bBb (convertase) complex as factor D and factor B were flowed together over C3b that was amine-coupled to a CM5 (Biacore) sensor chip. The subsequent decline in response reflects decay of the complex as Bb is released from the chip surface. The rate of decay is accelerated by initiating (in this case 210 s into the natural decay process) a flow of reference FH or rFH. At similar concentrations (0.5 μM), rFH is a more effective decay accelerator in this assay than plasma-purified FH. The control proteins, BSA and FH modules 19-20, have no effect on decay.

G—(i) and (ii)—Use of SPR to measure affinity of (i),FH and (ii) plasma-purified FH for C3b coupled to aCM5 sensor chip (Biacore). Duplicate sensorgrams are shown for a concentration series (5.4 μM, 1.0 μM, 0.5 μM, 0.1 μM) flowed over 1540 response units of immobilised C3b. (iii) and (iv)—Plots of response units versus (iii) rFH or (iv) plasma-purified FH concentrations for two different flow cells with either 1540 RUs (lower curve in each plot) or 3030 RUs (upper curve in each plot) of C3b. The dashed vertical line indicates the $K_D$ fitted in each case to both plots simultaneously, and yielding 1.4 μM for rFH and 2.9 μM for plasma-purified FH.

H—The candidate recombinant FH (peaks a and c correspond to double-charged and single-charged species, respectively) and an internal standard ($IgG_1$; peaks b and d correspond to double-charged and single-charged species, respectively) were analysed on a MALDI-ToF mass spectrometer.

I—Dynamic light scattering was performed on rFH in PBS at a concentration of 1 mg/ml.

J—Sheep erythrocytes were incubated in physiological buffer, with 1.5 μM FH modules 6-8 (negative control), 0.4 μM plasma-purified FH or 0.4 mM rFH prior to exposure (for 20 minutes at 37° C.) to human serum that had been depleted of FH. The reaction was quenched and $A_{412}$ was measured. The results shown were the average (plus or minus standard deviation) of four experiments.

FIG. 4(a) shows a schematic representation of human factor H (FH) showing certain SNP's and the eight N-linked glycans. 4(b) shows schematic representations of vector (plasmid) maps designed such that various FH molecules and variants can be prepared in accordance with the present invention. All except vector 4 (based on pPICZα-B) are based on pPIC3.5K. Vector numbers 1-3 and 11 incorporate DNA for the human secretion signal peptide (hum. signal pept.) while vector numbers 7, 9 and 10 incorporate the mouse equivalent. The other four vectors incorporate DNA for the yeast alpha-factor peptide with (vector number 4) or without (vectors 5, 6 and 8) EA dipeptides. The encoded variants of FH (sequences in FIG. 5) are indicated—the protective (prot.) and at-risk haplotypes are detailed in the text; "all-Q" and "one amber Q" or "two amber Q" refer to substitutions of Asn residues for Gln and one or two pPa residues (for example), respectively, as described in the text; "delta 10-15" indicates removal of FH domains 10-15 as described in the text; K/R indicates substitution of lysines and arginines with glutamines as described in the text.

FIG. 5 is a summary of DNA sequences encoding (a) human and (b) mouse FH variants that have been inserted into vector numbers 1-11.

FIG. 6 illustrates the expression of two recombinant variants of FH. The sample of "all-Q" mutant of rhFH (left-hand gel) migrates as a single band during SDS-PAGE under reducing (R) and non-reducing (NR) conditions (stained by Coomassie blue). Endo $H_f$ (77 kDa) treatment causes no change in migration rate. This is consistent with the "all-Q" mutant having no N-glycosylation sites and being glycan-free. For comparison (middle gel), rhFH (prior to purification) migrates as a fuzzy band until it is Endo $H_f$ treated (right-hand gel). The sample of "delta10-15" rFH was eluted from an anion-exchange column and six peak fractions collected and run on SDS-PAGE under reducing (R) or (for four fractions) non-reducing (NR) conditions (right-hand gel), then stained with Coomassie blue. MW=molecular weight markers as indicated to left and right of the gels.

FIG. 7 is a schematic summary of a route to therapeutic versions of FH.

Example 1

Attempted Expression of Non-Codon-Optimised DNA Encoding FH

Human FH-encoding DNA was amplified from cDNA, and inserted into the yeast expression vector pPICZalphaB, and KM71H *P. pastoris* cells were duly transformed. Cell colonies grew on high antibiotic-containing plates, consistent with the presence of multiple copies of the gene in the transformed cells. We failed, however, to detect (on SDS-PAGE, stained with Coomassie Blue) any evidence of FH expression in mini-scale cultures. Nor was any detectable recombinant FH produced in shaker-flask cultures. We next checked to see if protein expression by transformed cells could be detected under ideal expression conditions (as may be achieved in a one-liter fermentor in which oxygen and nutrient levels are maintained at near-optimal levels) and by using more sensitive detection methods (Western-dot-blot, see FIG. 2); notwithstanding these steps and even with the additional use of a larger-scale (three-liter) fermentation, no recombinant FH product could be detected.

In further attempts to find evidence for the expression of even small amounts of recombinant FH, a portion of the supernatant was concentrated (for Western-dot-blot) while the remainder was diluted (to reduce salt concentration) and loaded onto a HiTrap (GE Healthcare) heparin-affinity chromatography column at pH 6. A sample from a one-step elution (expected to wash all of the protein off in a small volume) with 1 M NaCl (in the equilibration buffer used for the HiTrap heparin column) was also assayed in a Western-dot-blot.

Detection was attempted using a standard Western-blotting technique with both a commercial polyclonal anti-FH antibody and secondary antibody coupled to horseradish peroxidase. With the exception of the positive controls (consisting of the primary anti-FH antibody, the secondary antibody, and human plasma-derived FH purchased from Complement Technology, Texas) no positive signal was detectable (see FIG. 2).

Thus, we demonstrated that provision of multiple-milligram, let alone multiple-gram, quantities of recombinant FH from wt FH-encoding DNA, despite the use of a heterologous expression system that is known to be particularly suitable for extracellular proteins containing disulfides and that has been used for expression of shorter segments of FH, is far from a straightforward matter.

Example 2

Development, Purification and Characterisation of Codon-Optimised Human Factor H Codon optimisation aimed at human FH expression in *P. pastoris* was carried out by consultation between the inventors and Geneart (Regensburg, Germany) using their proprietary techniques and GeneOptimizer® software.

The nucleic acid sequence of a codon-optimised form of human FH, for expression in *P. pastoris*, is significantly different (it has 76% sequence identity) to the native DNA sequence (see FIG. 1).

The codon-optimised DNA sequence was synthesised by Geneart and then cloned into an Invitrogen-purchased *P. pastoris*-based expression vector, pPICZ alpha B-vector, which had been restricted using appropriate restriction enzymes.

The vector was transformed into *E. coli* in order to amplify the DNA, yielding several 10 s of μg of plasmid DNA. This was purified, linearised (to enhance homologous recombination) and then transformed (using electroporation) into *P. pastoris* strain, KM71H. Selection of *P. pastoris* clones containing the expression plasmid was achieved by streaking transformed yeast onto rich-media plates containing a range of concentrations of an antibiotic marker. Colonies that grew on high antibiotic-containing plates were screened for protein expression.

After filtration to remove cells, the supernatant from the fermentor was diluted one-in-five with distilled water and applied to a self-poured XK-Heparin column (Heparin Fast-Flow resin—from GE Healthcare). Elution was accomplished with a linear gradient, over six column volumes, from 20 mM potassium phosphate buffer (pH 6.0) to the same buffer substituted with 1 M NaCl. Fractions containing protein were pooled and the glycans were removed by incubating the sample with Endoglycosidase H-mannose binding protein fusion protein (Endo $H_f$, New England Biolabs) at 37° C. Protein was then applied to a Concanavalin A (GE Healthcare) column and then to mannose-binding-resin (New England Biolabs) to remove *P. pastoris*-derived glycans and the Endo $H_f$. As an alternative to Endo $H_f$, an exoglycosydase may be utilised so as to retain more of the glycans on the recombinant product, which might enhance solubility.

The sample was further purified on a self-poured Poros-Heparin chromatography column and eluted, over 20 column volumes, with a linear gradient from PBS to PBS plus 1 M NaCl. The final purification step involved anion exchange on a MonoQ column. The protein was eluted by a gradient, over 20 column volumes, from 20 mM glycine buffer (pH 9.5) to the same buffer supplemented with 1 M NaCl.

Exemplary results of such a purification, followed by extensive biophysical and functional characterisation and validation, are shown in FIG. 3. The yield of protein from this procedure, that had not been optimised, was about 1.5-2.5 mg of protein from one liter.

Example 3

Further Development of Human and Mouse FH Variants Using Codon-Optimised DNA; Elaboration to Enhance Therapeutic Efficacy In a first step, a set of 11 plasmid vectors (vector numbers 1 through 11) was designed by the inventors (FIG. 4) in order to further exemplify the utility and versatility of expression of a synthetic codon-optimised gene in *P. pastoris*. This set of vectors was designed so as to allow "cutting and pasting" of DNA encoding FH between vectors so as to maximise the number of secretion pathways that could be easily explored for each of the targeted FH variants. The aim was to produce mouse FH in addition to human FH, since mouse FH is needed for trials in mice.

In a second step, the 11 DNA inserts (see FIG. 5 for sequence information) intended for codon optimisation were designed by the inventors based on (i) the desired amino acid residue sequences, (ii) the requirement for suitable endonuclease restriction sites, (iii) the incorporation of appropriate secretion signal sequences (peptides) at the N termini of the target proteins to promote secretion into the growth media, (iv) pursuit of the strategies summarised in FIG. 7 aimed at amassing the information required to optimise a biotherapeutic product derived from FH.

In a third step, codon optimisation and gene synthesis to create construct numbers 1 through 11 (summarised in FIG. 5) were carried out by Geneart (Regensburg, Germany) using their proprietary techniques and GeneOptimizer® software. Geneart were also contracted to incorporate the 11 constructs into inventor-supplied plasmids to generate vector numbers 1 through 11 (FIG. 4).

In the production of recombinant human (rhFH) described in Example 2 we employed a pre-pro leader (signal) sequence to direct secretion of rhFH, thereby facilitating purification. In that work, the pro-region was separated from the target sequence by an endopeptidase (kex2 protease)-cleavage site followed by two Glu-Ala dipeptides introduced to enhance cleavage-site accessibility. Native sequence generation relied upon kex2 protease to remove the pro-region, followed by dipeptidyl aminopeptidase action of the ste13-gene product to perform Glu-Ala removal. Incomplete cleavage by ste13 sometimes resulted in potentially immunogenic N-terminal Glu-Ala pairs. To eliminate this possibility, codons encoding one or both of said Glu-Ala dipeptides were avoided during creation of vector number 1 and additionally construct 1 was designed to exploit the native secretion signal sequence of hFH and processing by yeast secretion-pathway enzymes. Hence, using vector number 1 the N-terminal expression artefact ($NH_2$-Glu-Ala) that was included in our initial recombinant hFH is absent, and the presence of a previously present cloning artefact (Ala-Gly) is circumvented; in addition, using vector number 1, rhFH is in effect mutated to yield the protective haplotype (I62, Y402) (creating IY-hFH).

*Pichia pastoris* normally introduces high mannose-type N-glycans at Asn-Xaa-Thr/Ser sequons resulting in heterogenous, potentially immunogenic, products. These glycans lack terminal sialic acids and are probably susceptible to rapid clearance via hepatic asialoglycoprotein receptors. On the other hand, glycosylation may assist folding and stability of the recombinant protein and in the original study we removed *P. pastoris* N-glycans from rhFH enzymatically after expression and before purification or after the first purification step. Construct number 2 was designed so that Asn residues at N-glycosylation sites are replaced with Gln residues (FIG. 5) (to create allQ-IY-hFH). Thus vector number 2 allows assessment of the consequences of producing FH lacking eight normally occupied (out of nine potential) N-glycosylation sequons by mutating the relevant Asn residues to Gln residues. Thus using vector number 2 we produced, secreted (relying on the human-FH secretion signal sequence) and purified allQ-IY-hFH corresponding to the protective haplotype but with no N-glycosylation sites (see FIG. 6). We demonstrated that this material was glycan-free on the basis that no difference was observed in migration on SDS-PAGE before and after treatment with Endo $H_f$.

Construct 3 exploits the amber codon to allow replacement of a potentially N-glycosylated Asn residues in IY-hFH with an unnatural amino acid such as p-(propargoxy)phenylalanine (pPpa) (to create unN-IY-hFH) (see FIG. 5). Low long-term immunogenicity and enhanced half-life are essential properties in biotherapeutics suitable for supplementation of human FH function in patients. Attachment of poly(ethylene) glycols (PEGs) is a proven strategy in this respect (see e.g.

PEGylation, successful approach to drug delivery. Veronese F M, Pasut G. *Drug Discov Today.* 2005; 10:1451-8). Alternatives to PEGylation include conjugation with biodegradable polysialic acid chains that may have advantages over PEGs where high and repeated doses are involved (see e.g. Improving the therapeutic efficacy of peptides and proteins: a role for polysialic acids. Gregoriadis G, Jain S, Papaioannou I, Laing P. *Int J Pharm* 2005 300:125-30). It will be understood that numerous other polymers could be conjugated to hFH to improve its biotherapeutic potential. Randomly placed PEGylation or polysialylation for example, on primary amines is straightforward but frequently results in a heterogenous product and steric interference with binding regions on the protein. Far more desirable is site-specific modification. We are able to exploit this desirable option thanks to our use of *P. pastoris* as our preferred expression system. Indeed, a very significant advantage of *P. pastoris* over a non-yeast eukaryotic expression system is the possibility of easily replacing one or possibly two relevant Asn residues with non-naturally encoded amino acid residues (this is possible with other eukaryotic expression systems but is less straightforward and would not be expected to produce protein in the required yields).

Thus by transfecting *P. pastoris* with vector number 3, along with a plasmid carrying the requisite tRNAs and aminoacyl tRNA transferase, we introduce the option of site-specific covalent modification with a chemically synthesised polymer that should mask the altered residue and eliminate a glycosylation site while potentially enhancing other biotherapeutic properties of the protein. It should be noted that these residues are not directly involved in binding to other proteins since they are normally N-glycosylated and they lie within modules of FH that we have previously shown not to be involved in C3b or GAG-binding. The system for incorporation of an unnatural amino acid used is the one developed by Schultz (Expanding the genetic repertoire of the methylotrophic meast *Pichia pastoris*. Young T S, Ahmad I, Brock A, Schultz P G. *Biochemistry* 2009 48:2643-2653) for incorporation of pPpa that is suitable for side-chain modification using "click" chemistry. This utilises an orthogonal tRNA/tRNA and aminoacyl-tRNA synthetase pair developed in *E. coli* using directed evolution. This allows, in the first place, the biological and biophysical properties of unN-IY-hFH to be compared to those of IY-FH (after enzymatic deglycosylation) and allQ-IY-hFH. It will be understood that another unnatural amino acid could be incorporated instead of pPpa, which would provide alternative chemical routes to conjugation; for example, we could incorporate an unnatural amino acid with an azo-group or other reactive group. Many such possibilities are discussed in the above-cited paper by Young et al the contents of which are hereby incorporated in its entirety by reference. It will also be understood that other residues besides the Asn residues in N-glycosylation sites, for example the Ser or Thr residue that is found two residues after the Asn residue, could be replaced with unnatural amino acids.

Subsequently, click chemistry is utilised to PEGylate unN-IY-hFH creating our candidate therapeutic product, PEGylated-hFH (FIG. 7); for comparison, we non-specifically PEGylate Lys residues within allQ-IY-hFH (to create $PEG^x$-hFH). The creation of these proteins is as follows. Azo-derivitised PEGs are available commercially and these react with the propargyl group of pPpa in a Cu(I)-catalysed azide-alkyne cycloaddition to give a high yield of the 1,2,3-triazole. It will be understood that it is possible to incorporate azo-amino acid residues instead of pPpa and then to use propargyl-PEG as a conjugate. It will also be understood that conjugations with other polymers would be equally feasible. In this way we create site-specifically PEGylated versions of FH. It is possible to explore different chain lengths, and the use of branched chains. For comparison with the products of site-specific conjugation, we use well-established protocols that randomly conjugate succinamide-ester activated PEGs to primary amines of the recombinant protein (see Peptide and protein PEGylation: a review of problems and solutions. Veronese F M. *Biomaterials.* 2001, 22:405-17 and references therein). Using homogenous preparations of activated PEGs at appropriate stoichiometric ratios and by fractionating and characterising the products, one obtains well-defined positional isomers of mono/di-PEGylated protein. These operations are performed on IY-hFH creating $PEG^x$-IY-hFH. Thus it is possible to compare the relative merits of site-specific and random PEGylation. It will be understood that a similar approach may readily be extended to polysialylation instead of PEGylation.

With regard to comparisons of the various products—e.g. hFH, IY-hFH, allQ-IY-hFH, unN-IY-hFH, PEG-hFH and $PEG^x$-hFH—we explore their C3b- and GAG-binding properties and their bioactivities. Thus, pure and authenticated samples are tested for the following: (i) Ability to act as a cofactor for factor I-catalysed cleavage of C3b (see FIG. 3D) (Enzymic assay of C3b receptor on intact cells and solubilised cells. Sim E, Sim R B. *Biochem J.* 1983, 210: 567-76); (ii) Ability to promote acceleration of decay of C3bBb assembled on a surface plasmon resonance (SPR) sensor chip (Decay-accelerating factor must bind both components of the complement alternative pathway C3 convertase to mediate efficient decay. Harris C L, Pettigrew D M, Lea S M, Morgan B P. *J Immunol.* 2007 178:352-9) (see FIG. 3F); (iii) Affinity for C3b immobilised on a sensor chip as measured by SPR (A new map of glycosaminoglycan and C3b-binding sites on factor H. Schmidt C Q, Herbert A P, Kavanagh D, Gandy C, Fenton C J, Blaum B S, Lyon M, Uhrin D, Barlow P N. *J Immunol.* 2008 181:2610-9) (see FIG. 3G; (iv) Affinity for GAGs as measured by heparin-affinity chromatography or gel-mobility shift assay (Disease-associated sequence variations congregate in a polyanion recognition patch on human factor H revealed in three-dimensional structure. Herbert A P, Uhrin D, Lyon M, Pangburn M K, Barlow P N. *J Biol Chem.* 2006 281:16512-20); (v) Ability to protect sheep erythrocytes from complement-mediated haemolysis by FH-depleted human sera (available from Complement Technology)—a standard biological assay for human FH (Critical role of the C-terminal domains of factor H in regulating complement activation at cell surfaces. Ferreira V P, Herbert A P, Hocking H G, Barlow P N, Pangburn M K. *J Immunol.* 2006 177:6308-16) (see FIG. 3J); (vi) Ability to protect human cells from complement-mediated injury (Role of membrane cofactor protein (CD46) in regulation of C4b and C3b deposited on cells. Barilla-LaBarca M K, Liszewski M K, Lambris J D, Hourcade D, Atkinson J P. *J Immunol.* 2002 168:6298-304; Inhibiting complement activation on cells at the step of C3 cleavage. Liszewski M K, Fang C J, Atkinson J P. *Vaccine.* 2008, 26 Suppl 8:122-7.

In construct number 4 two amber codons have been incorporated and the protein product is suitable for site-specific placement of a pair of conjugates. With this construct it will be possible to explore the feasibility of introducing a second PEGylation site although it is expected that there may be a decrease in yield that generally accompanies each unnatural amino acid-residue incorporation. In this example, we have chosen conjugation sites on adjacent modules (modules 12 and 13) in the middle of the protein. Not only could these sites by PEGylated without compromising binding sites lying elsewhere in the FH molecule, they could be used for attachment of fluorescent probes resulting in fluorescent versions of human FH with potential applications in fluorescent microscopy and histology as well as diagnostics. Alternatively these sites could be used for conjugation with paramagnetic moieties that can be exploited in electron paramagnetic resonance spectroscopy to provide distance measurements between probes and, by inference, structural information that will help to generate hypotheses and the design of protein engineering approaches aimed at optimising FH efficacy.

Vectors 4 and 5 incorporate DNA encoding the yeast alpha-factor secretion signal peptide since it is potentially advantageous to explore secretion pathways other then the pathway that deals with the natural human FH secretion signal peptide. Vector 4 incorporates the codons for $NH_2$-Glu-Ala, while vector 5 does not, thereby providing opportunities to examine the role of the Glu-Ala spacer in terms of efficiency of proteolytic processing of the secretion signal peptide.

Vector 6 (utilising the alpha-factor/no-EA strategy) incorporates a construct encoding an example of a FH deletion. This term refers to versions of FH that are missing one or more central domains (or modules) within the region that connects together the two main C3b and GAG-binding sites proximal to the N and C termini. Such deletions represent an opportunity to create more compact version of hFH for research and therapeutic applications. In the current example (vector 6) modules 10-15 are deleted (for result, see FIG. 6). It will be appreciated that given the modularity of the FH structure it is possible to delete any number or combinations of modules (or to truncate FH at either end to create FH truncations). It is also facile to replace any of these deleted domains with homologous or non-homologous domains from other proteins. Vector 11 has been designed for production of an example of a FH mutant that can readily be produced in useful amounts using our strategy. In this example, nine basic amino acid residues have been replaced with Gln (neutral) residues. The basic amino acids selected in this case form a striking electropositive patch on module 13 of human FH (The central portion of factor H (modules 10-15) is compact and contains a structurally deviant CCP module. Schmidt C Q, Herbert A P, Mertens H D, Guariento M, Soares D C, Uhrin D, Rowe A J, Svergun D I, Barlow P N. *J Mol Biol.* 2009 Epub. Oct. 14.) which seems unlikely to have evolved by chance and may have an as yet unrecognised binding role in the biological mechanism of action of FH. Thus we exploit our protein production strategy both to make therapeutic proteins and to make versions of FH for assay that shed light on structure-function relationships and hence on engineering of designer versions of FH with superior therapeutic efficacy.

The subset of vectors numbered 7 through 10 were designed for production of mouse FH (mFH) in *P. pastoris* using codon-optimised DNA. These protein products assist in the assessment of FH as a biotherapeutic in mouse-based models of disease. The natural mFH secretion signal sequence is exploited in vectors 7, 9 and 10 while vector 8 contains DNA for the yeast alpha-factor secretion signal (no Glu-Ala). Construct 7 encodes wild-type mFH and constructs 8 and 9 encode the mouse equivalents of the allQ- and unN- (i.e. amber) versions of human FH (i.e. as in the human versions, one or two of the N-glycosylation sites of mFH are re-engineered as sites of site-specific conjugation) (allQ-mFH and unN-mFH). PEGylated (or polysialylated proteins) are constructed as described for hFH. Construct 10 encodes a two-amber-codon version of mFH in which the remaining glycosylation sites (except those in modules 1-4 and 19-20) have been substituted, Asn to Gln.

To evaluate clinical potential of the protein products of vectors 1-11, we begin with the products of vectors 7-10 and test these in (i) the FH-knockout mouse ($FH^{-/-}$) that has uncontrolled plasma C3 activation and develops DDD (Uncontrolled C3 activation causes membranoproliferative glomerulonephritis in mice deficient in complement factor H. Pickering M C, Cook H T, Warren J, Bygrave A E, Moss J, Walport M J, Botto M. *Nat Genet.* 2002 31:424-8) and retinal abnormalities (Complement factor H deficiency in aged mice causes retinal abnormalities and visual dysfunction. Coffey P J, Gias C, McDermott C J, Lundh P, Pickering M C, Sethi C, Bird A, Fitzke F W, Maass A, Chen L L, Holder G E, Luthert P J, Salt T E, Moss S E, Greenwood J. *Proc Natl Acad Sci USA.* 2007 104:16651-6), and (ii) the FH transgenic mouse (CFH-/-delta16-20 (in which, effectively, the truncated FH consisting of modules 1-15 replaces full-length FH) that develops aHUS (Spontaneous hemolytic uremic syndrome triggered by complement factor H lacking surface recognition domains. Pickering M C, de Jorge E G, Martinez-Barricarte R, Recalde S, Garcia-Layana A, Rose K L, Moss J, Walport M J, Cook H T, de Córdoba S R, Botto M. *J Exp Med* 2007 204:1249-56.). We select the best candidate(s) based on a range of considerations including yield of protein, bioassays and standard toxicology studies. For example, allQ-mFH, PEG-mFH and/or $PEG^x$-mFH (likely to have low immunogenicity) will be injected i.v./i.p. into the $FH^{-/-}$ mouse. Levels of complement components C3, factor B and naturally expressed mouse FH (as well as the recombinant mFH) are measured by ELISA to titrate optimal doses of mFH needed to achieve maximal complement regulation in the serum and to assess mFH half-lives. With the dosing schedule optimised we evaluate the efficacy of mFH against DDD and retinal abnormalities. Survival, renal function (urinary albumin, serum urea) and retinal abnormalities (behavioural and electrophysiological studies) of the $FH^{-/-}$ mice over a period of eight months (kidney)/24 months (retina) will be assessed and compared to untreated $FH^{-/-}$ mice. Histological studies (light microscopy, immunofluoresence and fluorescent and electron microscopy) are used to assess differences in glomerular and retinal pathology in the two groups. Any generation of antibodies against mFH in these FH-deficient mice is assessed by ELISA-based assays. The utility of our product(s) in aHUS is determined in analogous experiments in the $CFH^{-/-}$ delta16-20 mouse.

We are continuing to improve the yields of hFH by further DNA manipulation and optimisation of fermentation technology, aiming to achieve production levels in the region of grams of protein per 10-liter fermentation. In the literature on *P. pastoris*, expression levels of 100-500 mg or more protein per liter have been reported. Numerous strategies available for the improvement of yield include: further enhancements of DNA sequence to decrease RNA secondary structure; elimination of potential proteolytic sites where possible; wider screening and selection for high copy-number transformants arising from multiple integration events; choice of culture conditions e.g. agitation, oxygen supply, pH, temperature, and addition of reagents (e.g. EDTA, amine salts, casamino acids) to minimise proteolysis; timing and rates of glycerol/methanol feeds (reviewed in for example Expression of recombinant proteins in *Pichia pastoris*. Li P, Anumanthan A, Gao X G, Ilangovan K, Suzara V V, Düzgüne N, Renugopalakrishnan V. *Appl Biochem Biotechnol.* 2007 142:105-24).

What is claimed is:

1. A method for making a recombinant mammalian factor H (FH), the method comprising the step of:

expressing in a bacterial, fungal, insect or plant cell, in culture a codon-optimized nucleic acid sequence encoding the mammalian FH, the nucleic acid sequence comprising a deletion variant sequence of any one of SEQ ID NO: 1-13 thereof comprising domains 1-4 and 19-20 and a deletion of domains 8-18, wherein the nucleic acid sequence has been codon optimized to enhance expression in the bacterial, fungal, insect or plant cell and inserted into an expression vector.

2. The method according to claim 1 wherein at least 1 mg of the mammalian FH is produced per liter of culture medium.

3. The method according to claim 1 further comprising the step of purifying the mammalian FH from the cells and/or culture medium in which the cells are grown.

4. The method according to claim 3, wherein purifying the mammalian FH is carried out by a chromatographic technique.

5. The method according to claim 1, wherein the bacterial, fungal, insect or plant cell is a yeast cell, and wherein the yeast cell is *Pichia pastoris*.

6. The method according to claim 1, wherein the mammalian FH is selected from the group consisting of human FH, mouse FH, rat FH, hamster FH, rabbit FH, dog FH, horse FH, cow FH, pig FH, sheep FH, camel FH, cat FH, and guinea pig FH.

7. The method according to claim 1, wherein the codon-optimized nucleic acid sequence includes one or more single-nucleotide polymorphisms.

8. The method according to claim 7, wherein the one or more single-nucleotide polymorphisms are selected from the group consisting of Ile62Val, Tyr402His, and Arg 1210Cys.

9. The method according to claim 1, wherein the sequence of the mammalian FH includes one or more covalently modified natural or non-naturally encoded variant amino acids.

10. The method according to claim 9, wherein said one or more covalently modified natural or non-naturally encoded variant amino acids is covalently modified to include a moiety selected from the group consisting of glycosaminoglycans, polysialic acids, dextran (−1,6 polyglucose), dextran (−1,4 polyglucose), hyaluronic acid, chitosans, linear or branched polyethylene glycols, polyether polyols, N-(2-hydroxypropyl) methacrylamide copolymers, poly(vinylpyrrolidone), poly(ethyleneimine), linear polyamidoamines, poly(L-lysine), poly(glutamic acid), poly(malic acid) and poly(aspartamides).

11. The method according to claim 1, wherein the mammalian FH is conjugated with a chemical moiety or chemical moieties, wherein the moiety or moieties improve the biotherapeutic properties of the mammalian FH.

12. A nucleic acid sequence capable of expressing a FH polypeptide wherein the nucleic acid sequence is codon optimized for expression in a bacterial, fungal, insect or plant cell in culture in an amount greater than 1 mg per liter of culture wherein the nucleic acid sequence comprises domains 1-4 and 19-20 and a deletion variant sequence of any one of SEQ ID NOs: 1-13 comprising a deletion of domains 8-18.

13. A vector comprising the sequence according to claim 12.

14. A recombinantly expressed mammalian FH expressed from the nucleic acid sequence of claim 12.

15. A recombinantly expressed variant of mammalian FH comprising one or more amino acid residue substitutions designed to modulate one or more biological properties of the FH variant as compared to a native FH, obtained from a nucleic acid sequence capable of expressing a FH polypeptide, wherein the nucleic acid sequence is codon optimized for expression in a bacterial, fungal, insect or plant cell in culture in an amount greater than 1 mg per liter of culture and wherein the nucleic acid sequence comprises a deletion variant sequence of any one of SEQ ID NOs: 1-13 comprising domains 1-4 and 19-20, which comprises one or more amino acid substitutions and a deletion of domains 8-18.

16. A method of slowing the progression of or treating a disease in a subject in need thereof comprising the step of administering the recombinantly expressed mammalian FH according to claim 12 to the subject.

17. The method according to claim 16 for use in slowing the progression of treating a disease selected from the group consisting of AMD, atypical haemolytic uraemic syndrome (aHUS), or dense deposit disease (DDD).

18. The method according to claim 1 wherein the deletion variant comprises a deletion of domains 5-18.

19. A process for making a recombinant mammalian factor H (FH), the process comprising the step of:

expressing in *Pichia pastoris* a nucleic acid sequence codon optimized for enhancing expression in *P. pastoris* encoding the mammalian FH, wherein the nucleic acid sequence comprises a deletion variant sequence of any one of SEQ ID NOs: 1-13 comprising domains 1-4 and 19-20 and a deletion of domains 8-18.

20. The nucleic acid sequence according to claim 12 which has been codon-optimized for enhanced expression in *P. pastoris*.

21. The nucleic acid sequence according to claim 12 wherein the deletion variant comprises a deletion of domains 5-18.

22. The process according to claim 19 wherein the deletion variant comprises a deletion of domains 5-18.

* * * * *

SEQUENCE LISTING

<160> NUMBER OF SEQ ID NOS: 13

<210> SEQ ID NO 1
<211> LENGTH: 3642
<212> TYPE: DNA
<213> ORGANISM: Homo sapiens

<400> SEQUENCE: 1

| | | | | | |
|---|---|---|---|---|---|
| ggagattgca | atgaacttcc | tccaagaaga | aatacagaaa | ttctgacagg | ttcctggtct | 60 |
| gaccaaacat | atccagaagg | cacccaggct | atctataaat | gccgccctgg | atatagatct | 120 |
| cttggaaatg | taataatggt | atgcaggaag | ggagaatggg | ttgctcttaa | tccattaagg | 180 |
| aaatgtcaga | aaaggccctg | tggacatcct | ggagatactc | cttttggtac | ttttaccctt | 240 |
| acaggaggaa | atgtgtttga | atatggtgta | aaagctgtgt | atacatgtaa | tgaggggtat | 300 |
| caattgctag | gtgagattaa | ttaccgtgaa | tgtgacacag | atggatggac | caatgatatt | 360 |
| cctatatgtg | aagttgtgaa | gtgtttacca | gtgacacgca | cagagaatgg | aaaaattgtc | 420 |
| agtagtgcaa | tggaaccaga | tcgggaatac | cattttggac | aagcagtacg | gtttgtatgt | 480 |
| aactcaggct | acaagattga | aggagatgaa | gaaatgcatt | gttcagacga | tggttttggg | 540 |
| agtaaagaga | aaccaaagtg | tgtggaaatt | tcatgcaaat | ccccagatgt | tataaatgga | 600 |
| tctcctatat | ctcagaagat | tatttataag | gagaatgaac | gatttcaata | taatgtaac | 660 |
| atgggttatg | aatacagtga | agaggagat | gctgtatgca | ctgaatctgg | atggcgtccg | 720 |
| ttgccttcat | gtgaagaaaa | atcatgtgat | aatccttata | ttccaaatgg | tgactactca | 780 |
| ccttaagga | ttaaacacag | aactggagat | gaaatcacgt | accagtgtag | aaatggtttt | 840 |
| tatcctgcaa | cccgggaaa | tacagccaaa | tgcacaagta | ctggctggat | acctgctccg | 900 |
| agatgtacct | tgaaaccttg | tgattatcca | gacattaaac | atggaggtct | atatcatgag | 960 |
| aatatgcgta | gaccatactt | tccagtagct | gtaggaaaat | attactccta | ttactgtgat | 1020 |
| gaacactttg | agactccgtc | aggaagttac | tgggatcaca | ttcattgcac | acaagatgga | 1080 |
| tggtcgccag | cagtaccatg | cctcagaaaa | tgttatttc | cttatttgga | aaatggatat | 1140 |
| aatcaaaatt | atggaagaaa | gtttgtacag | ggtaaatcta | tagacgttgc | ctgccatcct | 1200 |
| ggctacgctc | ttccaaaagc | gcagaccaca | gttacatgta | tggagaatgg | ctggtctcct | 1260 |
| actcccagat | gcatccgtgt | caaaacatgt | tccaaatcaa | gtatagatat | tgagaatggg | 1320 |
| tttatttctg | aatctcagta | tacatatgcc | ttaaaagaaa | aagcgaaata | tcaatgcaaa | 1380 |
| ctaggatatg | taacagcaga | tggtgaaaca | tcaggatcaa | ttacatgtgg | gaaagatgga | 1440 |
| tggtcagctc | aacccacgtg | cattaaatct | tgtgatatcc | cagtatttat | gaatgccaga | 1500 |
| actaaaaatg | acttcacatg | gtttaagctg | aatgacacat | tggactatga | atgccatgat | 1560 |
| ggttatgaaa | gcaatactgg | aagcaccact | ggttccatag | tgtgtggtta | caatggttgg | 1620 |
| tctgatttac | ccatatgtta | tgaaagagaa | tgcgaacttc | ctaaaataga | tgtacactta | 1680 |
| gttcctgatc | gcaagaaaga | ccagtataaa | gttggagagg | tgttgaaatt | ctcctgcaaa | 1740 |
| ccaggattta | caatagttgg | acctaattcc | gttcagtgct | accacttgg | attgtctcct | 1800 |
| gacctcccaa | tatgtaaaga | gcaagtacaa | tcatgtggtc | cacctcctga | actcctcaat | 1860 |
| gggaatgtta | aggaaaaaac | gaaagaagaa | tatggacaca | gtgaagtggt | ggaatattat | 1920 |
| tgcaatcctg | gatttctaat | gaagggacct | aataaaattc | aatgtgttga | tggagagtgg | 1980 |
| acaactttac | cagtgtgtat | tgtggaggag | agtacctgtg | gagatatacc | tgaacttgaa | 2040 |
| catggctggg | cccagctttc | ttcccctcct | tattactatg | gagattcagt | ggaattcaat | 2100 |

| | |
|---|---|
| tgctcagaat catttacaat gattggacac agatcaatta cgtgtattca tggagtatgg | 2160 |
| acccaacttc cccagtgtgt ggcaatagat aaacttaaga agtgcaaatc atcaaattta | 2220 |
| attatacttg aggaacattt aaaaaacaag aaggaattcg atcataattc taacataagg | 2280 |
| tacagatgta gaggaaaaga aggatggata cacacagtct gcataaatgg aagatgggat | 2340 |
| ccagaagtga actgctcaat ggcacaaata caattatgcc cacctccacc tcagattccc | 2400 |
| aattctcaca atatgacaac cacactgaat tatcgggatg gagaaaaagt atctgttctt | 2460 |
| tgccaagaaa attatctaat tcaggaagga gaagaaatta catgcaaaga tggaagatgg | 2520 |
| cagtcaatac cactctgtgt tgaaaaaatt ccatgttcac aaccacctca gatagaacac | 2580 |
| ggaaccatta attcatccag gtcttcacaa gaaagttatg cacatgggac taaattgagt | 2640 |
| tatacttgtg agggtggttt caggatatct gaagaaatg aaacaacatg ctacatggga | 2700 |
| aaatggagtt ctccacctca gtgtgaaggc cttccttgta atctccacc tgagatttct | 2760 |
| catggtgttg tagctcacat gtcagacagt tatcagtatg gagaagaagt tacgtacaaa | 2820 |
| tgttttgaag gttttggaat tgatgggcct gcaattgcaa aatgcttagg agaaaaatgg | 2880 |
| tctcaccctc catcatgcat aaaaacagat tgtctcagtt tacctagctt tgaaaatgcc | 2940 |
| atacccatgg gagagaagaa ggatgtgtat aaggcgggtg agcaagtgac ttacacttgt | 3000 |
| gcaacatatt acaaaatgga tggagccagt aatgtaacat gcattaatag cagatgggac | 3060 |
| ggaaggccaa catgcagaga cacctcctgt gtgaatccgc ccacagtaca aaatgcttat | 3120 |
| atagtgtcga cagatgag taaatatcca tctggtgaga gagtacgtta tcaatgtagg | 3180 |
| agcccttatg aaatgtttgg ggatgaagaa gtgatgtgtt taaatggaaa ctggacggaa | 3240 |
| ccacctcaat gcaaagattc tacaggaaaa tgtgggcccc ctccacctat tgacaatggg | 3300 |
| gacattactt cattcccgtt gtcagtatat gctccagctt catcagttga gtaccaatgc | 3360 |
| cagaacttgt atcaacttga gggtaacaag cgaataacat gtagaaatgg acaatggtca | 3420 |
| gaaccaccaa aatgcttaca tccgtgtgta atatcccgag aaattatgga aaattataac | 3480 |
| atagcattaa ggtggacagc caaacagaag ctttattcga gaacaggtga atcagttgaa | 3540 |
| tttgtgtgta acgggggata tcgtctttca tcacgttctc acacattgcg aacaacatgt | 3600 |
| tgggatggga aactggagta tccaacttgt gcaaaaagat ag | 3642 |

<210> SEQ ID NO 2
<211> LENGTH: 3645
<212> TYPE: DNA
<213> ORGANISM: Artificial
<220> FEATURE:
<223> OTHER INFORMATION: Codon Optimised sequence for P. pastoris expression of human factor H

<400> SEQUENCE: 2

| | |
|---|---|
| gaggattgta acgagttgcc accaagaaga aacactgaga tcttgactgg ttcttggagt | 60 |
| gatcaaactt acccagaggg tactcaggct atctacaagt gtagaccagg ttacagatcc | 120 |
| ttgggtaacg ttatcatggt ttgtagaaag ggtgagtggg ttgcattgaa cccattgaga | 180 |
| aagtgtcaga aaagaccatg tggtcaccca ggtgatactc cattcggtac tttcactttg | 240 |
| actggtggta acgttttcga gtacggtgtt aaggctgttt acacttgtaa cgagggttac | 300 |
| cagttgttgg gagagatcaa ctacagagag tgtgatactg acggatggac taacgacatt | 360 |
| ccaatctgtg aagttgttaa tgtttgcca gttactgctc cagagaacgg aaagattgtt | 420 |
| tcctccgcta tggaaccaga tagagagtac cacttcggac aggctgttag attcgtttgt | 480 |

```
aactccggtt acaagattga aggtgacgaa gagatgcact gttctgatga cggtttctgg    540
tccaaagaaa agccaaagtg tgttgagatc tcctgtaagt ccccagacgt tattaacggt    600
tccccaatct cccaaaagat catctacaaa gagaacgaga gattccagta caagtgtaac    660
atgggttacg agtactctga aagaggtgac gctgtttgta ctgaatctgg atggagacca    720
ttgccatcct gtgaagagaa gtcctgtgac aacccataca ttccaaacgg tgactactcc    780
ccattgagaa tcaagcacag aactggtgac gagatcactt accagtgtag aaatggtttc    840
tacccagcta ctagaggtaa cactgctaag tgtacttcca ctggatggat tccagctcca    900
agatgtactt tgaagccatg tgactaccca gatatcaagc acggtggttt gtaccacgag    960
aacatgagaa ggccatactt cccagttgct gttggaaagt actactccta ctactgtgac   1020
gaacacttcg aaactccatc tggttcttac tgggaccaca tccactgtac tcaagatggt   1080
tggtccccag ctgttccatg tttgagaaaa tgttacttcc catacttgga aacggttac    1140 aaccagaact acggtagaaa gttcgttcag ggaaagtcca ttgacgttgc ttgtcatcca   1200
ggttacgctt tgccaaaggc tcagactact gttacttgta tggaaaacgg ttggtcccct   1260
actcctagat gtatcagagt taagacttgt tccaagtcct ccatcgacat tgagaacggt   1320
ttcatttccg agtcccagta cacttacgct ttgaaagaga aggctaagta ccagtgtaaa   1380
ttgggatacg ttactgctga cggtgaaact tccggatcaa tcacatgtgg aaaagacgga   1440
tggagtgctc aaccaacttg tatcaagtct tgtgacatcc cagttttcat gaacgctaga   1500
actaagaacg acttcacatg gttcaagttg aacgacactt tggactacga atgtcacgac   1560
ggttacgaat ctaacactgg ttccactact ggttccatcg tttgtggtta caatggatgg   1620
agtgacttgc caatctgtta cgagagagag tgcgagttgc caaagatcga cgttcatttg   1680
gttccagaca gaaagaagga ccagtacaaa gttggagagg ttttgaagtt ctcctgtaag   1740
ccaggtttca ctatcgttgg tccaaactcc gttcagtgtt accacttcgg tttgtctcca   1800
gacttgccta tctgtaaaga gcaggttcaa tcctgcggac caccaccaga attgttgaac   1860
ggtaacgtta agaaaaagac taaagaagag tacggtcact ccgaagttgt tgagtactac   1920
tgtaacccaa gattcttgat gaagggtcca aacaagatcc aatgtgttga cggtgagtgg   1980
actactttgc cagtttgtat cgttgaagag tccacttgtg gtgacattcc agaattggaa   2040
cacggatggg ctcaattgtc atcccaccct actactacg tgactccgt tgaattcaac    2100
```

-continued

```
tgtttcgagg gtttcggtat tgatggtcca gctatcgcta agtgtttggg agaaaagtgg    2880
tcccatcctc catcctgtat caagactgat tgtttgtcct tgccatcctt cgaaaacgct    2940
atcccaatgg gagaaaagaa ggacgtttac aaggctggtg aacaagttac ttatacttgt    3000
gctacttact acaagatgga cggtgcttcc aacgttactt gtatcaactc cagatggact    3060
ggtagaccaa cttgtagaga cacttcctgt gttaacccac caactgttca gaacgcttac    3120
atcgtttcca gacagatgtc taagtaccca tccggagaac gtgttagata ccaatgtaga    3180
tccccatacg agatgttcgg tgacgaagag gttatgtgtt gaacggtaa ttggactgaa     3240 ccaccacagt gtaaggactc cactggtaag tgtggtccac ctccaccaat gacaacggt     3300 gacatcactt ctttcccttt gtccgtttac gctccagctt cttccgttga gtaccagtgt    3360
cagaacttgt accagttgga gggtaacaag agaatcactt gtagaaacgg acaatggagt    3420
gagccaccaa agtgtttgca cccatgtgtt atctccagag aaatcatgga aaactacaac    3480
attgctttga gatggactgc taaacagaag ttgtactcca gaactggtga atccgttgag    3540
ttcgtttgta agagaggtta cagattgtcc tccagatccc acactttgag aactacatgt    3600
tgggacggaa aattggagta cccaacttgt gctaagagat agtag                    3645
```

<210> SEQ ID NO 3
<211> LENGTH: 3733
<212> TYPE: DNA
<213> ORGANISM: Artificial
<220> FEATURE:
<223> OTHER INFORMATION: Codon optimised human hactor H variant

<400> SEQUENCE: 3

```
ggcgcgccgg atccaaaaat gagattgttg gctaagatca tctgtttgat gttgtgggct      60
atctgtgttg ctgaggactg taacgaattg ccaccgcgga gaaacactga gatttttgact    120 ggttcctggt ccgatcaaac ttacccagag ggtactcagg ctatctacaa gtgtagacca    180
ggttacagat ccttgggtaa catcatcatg gtttgtagaa agggtgagtg ggttgctttg    240
aacccattga gaaagtgtca gaaaagacca tgtggtcacc caggtgatac tccattcggt    300
actttcactt tgactggtgg taacgttttc gagtacggtg ttaaggctgt ttacacttgt    360
aacgagggtt accagttgtt gggtgagatc aactacagag agtgtgatac tgacggttgg    420
actaacgaca ttccaatctg tgaggttgtt aagtgtttgc agttactgc tccagagaac    480 ggtaagattg tttcctccgc tatggaacca gatagagagt accacttcgg tcaggctgtt    540
agattcgttt gtaactccgg ttacaagatt gaaggtgacg aagagatgca ctgttctgat    600
gacggtttct ggtccaaaga aaagccaaag tgtgttgaga tttcctgtaa gtccccagac    660
gttattaacg gttccccaat ctcccaaaag atcatctaca agagaacga gagattccag    720 tacaagtgta acatgggtta cgagtactct gaaagaggtg acgctgtttg tactgaatct    780
ggttggagac cattgccatc ctgtgaagag aagtcctgtg acaacccata cattccaaac    840
ggtgactact ccccattgag aatcaagcac agaactggtg acgagatcac ttaccagtgt    900
agaaacggtt tctacccagc tactagaggt aacactgcta agtgtacttc cactggttgg    960
attccagctc caagatgtac tttgaagcca tgtgactacc cagatatcaa gcacggtggt   1020
ttgtaccacg agaacatgag aagaccatac ttcccagttg ctgttggaaa gtactactcc   1080
tactactgtg acgaacactt cgaaactcca tctggttctt actgggacca catccactgt   1140
actcaagatg gttggtcccc agctgttcca tgtttgagaa aatgttactt cccatacttg   1200
gagaacggtt acaaccagaa ctacggtaga aagttcgttc agggaaagtc cattgacgtt   1260
```

```
gcttgtcatc caggttacgc tttgccaaag gctcagacta ctgttacttg tatggaaaac   1320
ggttggtccc ctactcctag atgtatcaga gttaagactt gttccaagtc ctccatcgac   1380
attgagaacg gtttcatttc cgagtcccag tacacttacg ctttgaaaga gaaggctaag   1440
taccagtgta aattgggata cgttactgct gacggtgaaa cttccggttc catcacttgt   1500
ggtaaggatg gttggtctgc tcaaccaact tgtatcaagt cttgtgacat cccagttttc   1560
atgaacgcta gaactaagaa cgacttcaca tggttcaagt tgaacgacac tttggactac   1620
gaatgtcacg acggttacga atctaacact ggttccacta ctggttccat cgtttgtggt   1680
tacaacggtt ggtctgactt gccaatctgt tacgagagag agtgcgagtt gccaaagatc   1740
gacgttcatt tggttccaga cagaagaag gaccagtaca aggttggtga ggttttgaag    1800
ttctcctgta agccaggttt cactatcgtt ggtccaaact ccgttcagtg ttaccatttc   1860
ggtttgtccc cagacttgcc tatttgtaaa gagcaggttc agtcttgcgg tccaccacca   1920
gaattgttga cggtaacgt taagaaaag actaaagaag agtacggtca ctctgaggtt     1980
gttgagtact actgtaaccc aagattcttg atgaagggtc caaacaagat ccaatgtgtt   2040
gacggtgagt ggactacttt gccagtttgt atcgttgaag agtccacttg tggtgacatt   2100
ccagaattgg aacacggttg ggctcaattg tcatccccac catactacta cggtgactcc   2160
gttgagttca actgttccga gtccttcact atgattggtc acagatccat cacatgtatc   2220
cacggtgttt ggactcaatt gccacagtgt gttgctatcg acaagttgaa gaagtgtaaa   2280
tcctccaact tgatcatctt ggaggaacac ttgaagaaca agaaagagtt cgaccacaac   2340
tccaacatca gatacagatg tagaggtaaa gagggttgga ttcacactgt ttgtatcaac   2400
ggtagatggg accctgaagt taactgttcc atggctcaga ttcagttgtg tccaccacct   2460
ccacaaattc caaactccca caacatgact actactttga actacagaga tggtgagaag   2520
gtttccgttt tgtgtcaaga gaactacttg atccaagagg gtgaggaaat cacttgtaag   2580
gacggtagat ggcaatccat cccattgtgt gttgagaaga tcccatgttc caaccacca    2640 caaattgagc acggtactat caactcttcc agatcctctc aagagtctta cgctcacggt   2700
actaagttgt cctacacttg tgagggtggt ttcagaatct ctgaggaaaa cgagactact   2760
tgttacatgg gaaagtggtc ctctccacca caatgtgaag gtttgccttg taagtctcca   2820
ccagagattt ctcacggtgt tgttgctcac atgtccgact cttaccaata cggtgaagag   2880
gttacttaca gtgtttcga gggtttcggt attgatggtc cagctatcgc taagtgtttg    2940
ggtgaaaagt ggtcccatcc tccatcctgt atcaagactg actgtttgtc cttgccatct   3000
ttcgagaacg ctatcccaat gggtgaaaag aaggacgttt acaaggctgg tgaacaggtt   3060
acatacactt gtgctactta ctacaagatg acggtgctt ccaacgttac ttgtatcaac    3120
tccagatgga ctggtagacc aacttgtaga gacacttcct gtgttaaccc accaactgtt   3180
cagaacgctt acatcgtttc cagacagatg tctaagtacc catccggtga gagagttaga   3240
taccaatgta gatccccata cgagatgttc ggtgacgaag aggttatgtg tttgaacggt   3300
aattggactg aaccaccaca gtgtaaggac tccactggta agtgtggtcc acctccacca   3360
attgacaacg gtgacatcac ttctttccca ttgtccgttt acgctccagc ttcttccgtt   3420
gagtaccagt gtcagaactt gtaccagttg gagggtaaca agagaatcac ttgtagaaac   3480
ggacaatggt ctgagccacc aaagtgtttg cacccatgtg ttatctccag agaaatcatg   3540
gaaaactaca acattgcttt gagatggact gctaagcaga agttgtactc cagaacaggt   3600
```

```
gagtctgttg agtttgtttg taagagaggt tacagattgt cctccagatc ccacactttg      3660
agaactacat gttgggacgg aaagttggag tacccaactt gtgctaagag ataatgagcg      3720
gccgcttaat taa                                                        3733

<210> SEQ ID NO 4
<211> LENGTH: 3733
<212> TYPE: DNA
<213> ORGANISM: Artificial
<220> FEATURE:
<223> OTHER INFORMATION: Codon optimised human hactor H variant

<400> SEQUENCE: 4
ggcgcgccgg atccaaaaat gagattgttg gctaagatca tctgtttgat gttgtgggct        60
atctgtgttg ctgaggactg taacgaattg ccaccgcgga gaaacactga gattttgact       120
ggttcctggt ccgatcaaac ttacccagag ggtactcagg ctatctacaa gtgtagacca       180
ggttacagat ccttgggtaa catcatcatg gtttgtagaa agggtgagtg ggttgctttg       240
aacccattga gaaagtgtca gaaaagacca tgtggtcacc caggtgatac tccattcggt       300
actttcactt tgactggtgg taacgttttc gagtacggtg ttaaggctgt ttacacttgt       360
aacgagggtt accagttgtt gggtgagatc aactacagag tgtgatac tgacggttgg       420 actaacgaca ttccaatctg tgaggttgtt aagtgtttgc agttactgc tccagagaac       480 ggtaagattg tttcctccgc tatggaacca gatagagagt accacttcgg tcaggctgtt       540
agattcgttt gtaactccgg ttacaagatt gaaggtgacg aagagatgca ctgttctgat       600 gacggttttct ggtccaaaga aaagccaaag tgtgttgaga tttcctgtaa gtccccagac       660
gttattaacg gttcccccaat ctcccaaaag atcatctaca agagaacga gagattccag       720 tacaagtgta catgggttta cgagtactct gaaagaggtg acgctgtttg tactgaatct       780
ggttggagac cattgccatc ctgtgaagag aagtcctgtg acaacccata cattccaaac       840
ggtgactact ccccattgag aatcaagcac agaactggtg acgagatcac ttaccagtgt       900
agaaacggtt tctacccagc tactagaggt aacactgcta gtgtacttc cactggttgg       960 attccagctc caagatgtac tttgaagcca tgtgactacc cagatatcaa gcacggtggt      1020
ttgtaccacg agaacatgag aagaccatac ttcccagttg ctgttggaaa gtactactcc      1080
tactactgtg acgaacactt cgaaactcca tctggttctt actgggacca catccactgt      1140
actcaagatg gttggtcccc agctgttcca tgtttgagaa aatgttactt cccatacttg      1200
gagaacggtt acaaccagaa ctacggtaga aagttcgttc agggaaagtc cattgacgtt      1260
gcttgtcatc caggttacgc tttgccaaag gctcagacta ctgttacttg tatggaaaac      1320
ggttggtccc ctactcctag atgtatcaga gttaagactt gttccaagtc ctccatcgac      1380
attgagaacg gtttcatttc cgagtcccag tacacttacg ctttgaaaga aaggctaag      1440 taccagtgta aattgggata cgttactgct gacggtgaaa cttccggttc catcacttgt      1500
ggtaaggatg gttggtctgc tcaaccaact tgtatcaagt cttgtgacat cccagttttc      1560
atgaacgcta gaactaagaa cgacttcaca tggttcaagt tgcaagacac tttggactac      1620
gaatgtcacg acggttacga atctaacact ggttccacta ctggtccat cgttgtggt      1680 tacaacggtt ggtctgactt gccaatctgt tacgagagag agtgcgagtt gccaaagatc      1740
gacgttcatt tggttccaga cagaaagaag gaccagtaca aggttggtga ggttttgaag      1800
ttctcctgta agccaggttt cactatcgtt ggtccaaact ccgttcagtg ttaccatttc      1860
ggtttgtccc cagacttgcc tatttgtaaa gagcaggttc agtcttgcgg tccaccacca      1920
```

```
gaattgttga acggtaacgt taaagaaaag actaaagaag agtacggtca ctctgaggtt      1980
gttgagtact actgtaaccc aagattcttg atgaagggtc caaacaagat ccaatgtgtt      2040
gacggtgagt ggactacttt gccagtttgt atcgttgaag agtccacttg tggtgacatt      2100
ccagaattgg aacacggttg ggctcaattg tcatccccac catactacta cggtgactcc      2160
gttgagttcc aatgttccga gtccttcact atgattggtc acagatccat cacatgtatc      2220
cacggtgttt ggactcaatt gccacagtgt gttgctatcg acaagttgaa gaagtgtaaa      2280
tcctccaact tgatcatctt ggaggaacac ttgaagaaca agaaagagtt cgaccacaac      2340
tccaacatca gatacagatg tagaggtaaa gagggttgga ttcacactgt ttgtatcaac      2400
ggtagatggg accctgaagt tcaatgttcc atggctcaga ttcagttgtg tccaccacct      2460
ccacaaattc caaactccca ccaaatgact actactttga actacagaga tggtgagaag      2520
gtttccgttt tgtgtcaaga gaactacttg atccaagagg gtgaggaaat cacttgtaag      2580
gacggtagat ggcaatccat cccattgtgt gttgagaaga tcccatgttc caaccacca       2640
caaattgagc acggtactat ccaatcttcc agatcctctc aagagtctta cgctcacggt      2700
actaagttgt cctacacttg tgagggtggt ttcagaatct ctgaggaaca agagactact      2760
tgttacatgg aaagtggtc ctctccacca caatgtgaag gtttgccttg taagtctcca       2820
ccagagattt ctcacggtgt tgttgctcac atgtccgact cttaccaata cggtgaagag      2880
gttacttaca agtgtttcga gggtttcggt attgatggtc cagctatcgc taagtgtttg      2940
ggtgaaaagt ggtcccatcc tccatcctgt atcaagactg actgtttgtc cttgccatct      3000
ttcgagaacg ctatcccaat gggtgaaaag aaggacgttt acaaggctgg tgaacaggtt      3060
acatacactt gtgctactta ctacaagatg gacggtgctt cccaagttac ttgtatcaac      3120
tccagatgga ctggtagacc aacttgtaga gacacttcct gtgttaaccc accaactgtt      3180
cagaacgctt acatcgtttc cagacagatg tctaagtacc catccggtga gagagttaga      3240
taccaatgta gatccccata cgagatgttc ggtgacgaag aggttatgtg tttgaacggt      3300
caatggactg aaccaccaca gtgtaaggac tccactggta gtgtggtcc acctccacca       3360
attgacaacg gtgacatcac ttctttccca ttgtccgttt acgctccagc ttcttccgtt      3420
gagtaccagt gtcagaactt gtaccagttg gagggtaaca agagaatcac ttgtagaaac      3480
ggacaatggt ctgagccacc aaagtgtttg cacccatgtg ttatctccag agaaatcatg      3540
gaaaactaca acattgcttt gagatggact gctaagcaga agttgtactc cagaacaggt      3600
gagtctgttg agtttgtttg taagagaggt tacagattgt cctccagatc ccacactttg      3660
agaactacat gttgggacgg aaagttggag tacccaactt gtgctaagag ataatgagcg      3720
gccgcttaat taa                                                        3733

<210> SEQ ID NO 5
<211> LENGTH: 3733
<212> TYPE: DNA
<213> ORGANISM: Artificial
<220> FEATURE:
<223> OTHER INFORMATION: Codon optimised human hactor H variant

<400> SEQUENCE: 5
ggcgcgccgg atccaaaaat gagattgttg ctaagatca tctgtttgat gttgtgggct       60
atctgtgttg ctgaggactg taacgaattg ccaccgcgga gaaacactga gattttgact      120
ggttcctggt ccgatcaaac ttacccagag ggtactcagg ctatctacaa gtgtagacca      180
```

```
ggttacagat ccttgggtaa catcatcatg gtttgtagaa agggtgagtg ggttgctttg      240
aacccattga gaaagtgtca gaaaagacca tgtggtcacc caggtgatac tccattcggt      300
actttcactt tgactggtgg taacgttttc gagtacggtg ttaaggctgt ttacacttgt      360
aacgagggtt accagttgtt gggtgagatc aactacagag agtgtgatac tgacggttgg      420
actaacgaca ttccaatctg tgaggttgtt aagtgtttgc cagttactgc tccagagaac      480
ggtaagattt tttcctccgc tatggaacca gatagagagt accacttcgg tcaggctgtt      540
agattcgttt gtaactccgg ttacaagatt gaaggtgacg aagagatgca ctgttctgat      600
gacggtttct ggtccaaaga aaagccaaag tgtgttgaga tttcctgtaa gtccccagac      660
gttattaacg gttccccaat ctcccaaaag atcatctaca aagagaacga gagattccag      720
tacaagtgta acatgggtta cgagtactct gaaagaggtg acgctgtttg tactgaatct      780
ggttggagac cattgccatc ctgtgaagag aagtcctgtg acaacccata cattccaaac      840
ggtgactact ccccattgag aatcaagcac agaactggtg acgagatcac ttaccagtgt      900
agaaacggtt tctacccagc tactagaggt aacactgcta agtgtacttc cactggttgg      960
attccagctc caagatgtac tttgaagcca tgtgactacc cagatatcaa gcacggtggt     1020
ttgtaccacg agaacatgag aagaccatac ttcccagttg ctgttggaaa gtactactcc     1080
tactactgtg acgaacactt cgaaactcca tctggttctt actgggacca catccactgt     1140
actcaagatg gttggtcccc agctgttcca tgtttgagaa aatgttactt cccatacttg     1200
gagaacggtt acaaccagaa ctacggtaga aagttcgttc agggaaagtc cattgacgtt     1260
gcttgtcatc caggttacgc tttgccaaag gctcagacta ctgttacttg tatggaaaac     1320
ggttggtccc ctactcctag atgtatcaga gttaagactt gttccaagtc ctccatcgac     1380
attgagaacg gtttcatttc cgagtcccag tacacttacg ctttgaaaga aaggctaag     1440 taccagtgta aattgggata cgttactgct gacggtgaaa cttccggttc catcacttgt     1500
ggtaaggatg gttggtctgc tcaaccaact tgtatcaagt cttgtgacat cccagttttc     1560
atgaacgcta gaactaagaa cgacttcaca tggttcaagt tgcaagacac tttggactac     1620
gaatgtcacg acggttacga atctaacact ggttccacta ctggttccat cgtttgtggt     1680
tacaacggtt ggtctgactt gccaatctgt tacgagagag agtgcgagtt gccaaagatc     1740
gacgttcatt tggttccaga cagaaagaag gaccagtaca aggttggtga ggttttgaag     1800
ttctcctgta agccaggttt cactatcgtt ggtccaaact ccgttcagtg ttaccatttc     1860
ggttgtcccc cagacttgcc tatttgtaaa gagcaggttc agtcttgcgg tccaccacca     1920
gaattgttga acggtaacgt taagaaaaag actaagaag agtacggtca ctctgaggtt     1980
gttgagtact actgtaaccc aagattcttg atgaagggtc caaacaagat ccaatgtgtt     2040
gacggtgagt ggactacttt gccagtttgt atcgttgaag agtccacttg tggtgacatt     2100
ccagaattgg aacacggttg ggctcaattg tcatccccac catactacta cggtgactcc     2160
gttgagttcc aatgttccga gtccttcact atgattggtc acagatccat cacatgtatc     2220
cacggtgttt ggactcaatt gccacagtgt gttgctatcg acaagttgaa gaagtgtaaa     2280
tcctccaact tgatcatctt ggaggaacac ttgaagaaca agaaagagtt cgaccacaac     2340
tccaacatca gatacagatg tagaggtaaa gagggttgga ttcacactgt tgtatcaac      2400 ggtagatggg accctgaagt tcaatgttcc atggctcaga ttcagttgtg tccaccacct     2460
ccacaaattc caaactccca ccaaatgact actactttga actacagaga tggtgagaag     2520
gtttccgttt tgtgtcaaga gaactacttg atccaagagg gtgaggaaat cacttgtaag     2580
```

```
gacggtagat ggcaatccat cccattgtgt gttgagaaga tcccatgttc caaccacca      2640 caaattgagc acggtactat ccaatctagt agatcctctc aagagtctta cgctcacggt     2700
actaagttgt cctacacttg tgagggtggt ttcagaatct ctgaggaata ggagactact     2760
tgttacatgg gaaagtggtc ctctccacca caatgtgaag gtttgccttg taagtctcca     2820
ccagagattt ctcacggtgt tgttgctcac atgtccgact cttaccaata cggtgaagag     2880
gttacttaca agtgtttcga gggtttcggt attgatggtc cagctatcgc taagtgtttg     2940
ggtgaaaagt ggtcccatcc tccatcctgt atcaagactg actgtttgtc cttgccatct     3000
ttcgagaacg ctatcccaat gggtgaaaag aaggacgttt acaaggctgg tgaacaggtt     3060
acatacactt gtgctactta ctacaagatg gacggtgctt cccaagttac ttgtatcaac     3120
tccagatgga ctggtagacc aacttgtaga gacacttcct gtgttaaccc accaactgtt     3180
cagaacgctt acatcgtttc cagacagatg tctaagtacc catccggtga gagagttaga     3240
taccaatgta gatccccata cgagatgttc ggtgacgaag aggttatgtg tttgaacggt     3300
caatggactg aaccaccaca gtgtaaggac tccactggta agtgtggtcc acctccacca     3360
attgacaacg tgacatcac ttcttcccca ttgtccgttt acgctccagc ttcttccgtt      3420
gagtaccagt gtcagaactt gtaccagttg gagggtaaca agagaatcac ttgtagaaac     3480
ggacaatggt ctgagccacc aaagtgtttg cacccatgtg ttatctccag agaaatcatg     3540
gaaaactaca acattgcttt gagatggact gctaagcaga agttgtactc cagaacaggt     3600
gagtctgttg agtttgtttg taagagaggt tacagattgt cctccagatc ccacactttg     3660
agaactacat gttgggacgg aaagttggag tacccaactt gtgctaagag ataatgagcg     3720
gccgcttaat taa                                                        3733

<210> SEQ ID NO 6
<211> LENGTH: 3676
<212> TYPE: DNA
<213> ORGANISM: Artificial
<220> FEATURE:
<223> OTHER INFORMATION: Codon optimised human hactor H variant

<400> SEQUENCE: 6
ggcgcgcctg caggtgagga ctgtaacgaa ttgccaccgc ggagaaacac tgagattttg       60
actggttcct ggtccgatca aacttaccca gagggtactc aggctatcta caagtgtaga     120
ccaggttaca gatccttggg taacatcatc atggtttgta aagggtga gtgggttgct       180 ttgaacccat tgagaaagtg tcagaaaaga ccatgtggtc acccaggtga atactccattc    240 ggtactttca ctttgactgg tggtaacgtt ttcgagtacg gtgttaaggc tgtttacact     300
tgtaacgagg gttaccagtt gttgggtgag atcaactaca gagtgtgga tactgacggt      360 tggactaacg acattccaat ctgtgaggtt gttaagtgtt gccagttac tgctccagag     420 aacggtaaga ttgttttcctc cgctatggaa ccagatagag agtaccactt cggtcaggct    480
gttagattcg tttgtaactc cggttacaag attgaaggtg acgaagagat gcactgttct     540
gatgacggtt tctggtccaa agaaaagcca agtgtgttg agatttcctg taagtcccca     600
gacgttatta acggttcccc aatctcccaa aagatcatct acaaagagaa cgagagattc     660
cagtacaagt gtaacatggg ttacgagtac tctgaaagag gtgacgctgt tgtactgaa      720 tctggttgga gaccattgcc atcctgtgaa gagaagtcct gtgacaaccc atacattcca     780
aacggtgact actcccccatt gagaatcaag cacagaactg gtgacgagat cacttaccag     840
```

```
tgtagaaacg gtttctaccc agctactaga ggtaacactg ctaagtgtac ttccactggt      900
tggattccag ctccaagatg tactttgaag ccatgtgact acccagatat caagcacggt      960
ggtttgtacc acgagaacat gagaagacca tacttcccag ttgctgttgg aaagtactac     1020
tcctactact gtgacgaaca cttcgaaact ccatctggtt cttactggga ccacatccac     1080
tgtactcaag atggttggtc cccagctgtt ccatgtttga gaaaatgtta cttcccatac     1140
ttggagaacg gttacaacca gaactacggt agaaagttcg ttcagggaaa gtccattgac     1200
gttgcttgtc atccaggtta cgctttgcca aaggctcaga ctactgttac ttgtatggaa     1260
aacggttggt cccctactcc tagatgtatc agagttaaga cttgttccaa gtcctccatc     1320
gacattgaga acggtttcat ttccgagtcc cagtacactt acgctttgaa agagaaggct     1380
aagtaccagt gtaaattggg atacgttact gctgacggtg aaacttccgg ttccatcact     1440
tgtggtaagg atggttggtc tgctcaacca acttgtatca agtcttgtga catcccagtt     1500
ttcatgaacg ctagaactaa gaacgacttc acatggttca agttgaacga cactttggac     1560
tacgaatgtc acgacggtta cgaatctaac actggttcca ctactggttc catcgtttgt     1620
ggttacaacg gttggtctga cttgccaatc tgttacgaga gagtgcga gttgccaaag     1680 atcgacgttc atttggttcc agacagaaag aaggaccagt acaaggttgg tgaggttttg     1740
aagttctcct gtaagccagg tttcactatc gttggtccaa actccgttca gtgttaccat     1800 ttcggttttgt ccccagactt gcctatttgt aaagagcagg ttcagtcttg cggtccacca     1860
ccagaattgt tgaacggtaa cgttaaagaa aagactaaag aagagtacgg tcactctgag     1920
gttgttgagt actactgtaa cccaagattc ttgatgaagg gtccaaacaa gatccaatgt     1980
gttgacggtg agtggactac tttgccagtt tgtatcgttg aagagtccac ttgtggtgac     2040
attccagaat tggaacacgg ttgggctcaa ttgtcatccc caccatacta ctacggtgac     2100
tccgttgagt tctagtgttc cgagtccttc actatgattg gtcacagatc catcacatgt     2160
atccacggtt tttggactca attgccacag tgtgttgcta tcgacaagtt gaagaagtgt     2220
aaatcctcca acttgatcat cttggaggaa cacttgaaga caagaaaga gttcgaccac     2280 aactccaaca tcagatacag atgtagaggt aaagagggtt ggattcacac tgtttgtatc     2340
aacggtagat gggaccctga agttaactgt tccatggctc agattcagtt gtgtccacca     2400
cctccacaaa ttccaaactc ccacaacatg actactactt tgaactacag agatggtgag     2460
aaggtttccg ttttgtgtca agagaactac ttgatccaag agggtgagga aatcacttgt     2520
aaggacggta gatggcaatc catcccattg tgtgttgaga agatcccatg ttcccaacca     2580
ccacaaattg agcacggtac tatcaactct tccagatcct ctcaagagtc ttacgctcac     2640
ggtactaagt tgtcctacac ttgtgagggt ggtttcagaa tctctgagga ataggagact     2700
acttgttaca tgggaaagtg gtcctctcca ccacaatgtg aaggtttgcc ttgtaagtct     2760
ccaccagaga tttctcacgg tgttgttgct cacatgtccg actcttacca atacggtgaa     2820
gaggttactt acaagtgttt cgagggtttc ggtattgatg gtccagctat cgctaagtgt     2880
ttgggtgaaa agtggtccca tcctccatcc tgtatcaaga ctgactgttt gtccttgcca     2940
tctttcgaga acgctatccc aatgggtgaa aagaaggacg tttacaaggc tggtgaacag     3000
gttacataca cttgtgctac ttactacaag atggacggtg cttccaacgt tacttgtatc     3060
aactccagat ggactggtag accaacttgt agagacactt cctgtgttaa cccaccaact     3120
gttcagaacg cttacatcgt ttccagacag atgtctaagt acccatccgg tgagagagtt     3180
agataccaat gtagatcccc atacgagatg ttcggtgacg aagaggttat gtgtttgaac     3240
```

```
ggtaattgga ctgaaccacc acagtgtaag gactccactg gtaagtgtgg tccacctcca   3300
ccaattgaca acggtgacat cacttctttc ccattgtccg tttacgctcc agcttcttcc   3360
gttgagtacc agtgtcagaa cttgtaccag ttggagggta acaagagaat cacttgtaga   3420
aacggacaat ggtctgagcc accaaagtgt ttgcacccat gtgttatctc cagagaaatc   3480
atggaaaact acaacattgc tttgagatgg actgctaagc agaagttgta ctccagaaca   3540
ggtgagtctg ttgagtttgt ttgtaagaga ggttacagat tgtcctccag atcccacact   3600
ttgagaacta catgttggga cggaaagttg gagtacccaa cttgtgctaa gagataatga   3660
gcggccgctt aattaa                                                   3676

<210> SEQ ID NO 7
<211> LENGTH: 3934
<212> TYPE: DNA
<213> ORGANISM: Artificial
<220> FEATURE:
<223> OTHER INFORMATION: Codon optimised human hactor H variant

<400> SEQUENCE: 7
ggcgcgccgg atccaaaaat gagattccca tccatcttca ctgctgtttt gttcgctgct     60
tcttctgctt tggctgctcc agttaacact actactgagg acgagactgc tcaaattcca    120
gctgaggctg ttattggtta ctctgacttg gaaggtgatt tcgacgttgc tgttttgcca    180
ttctccaact ccactaacaa cggtttgttg ttcatcaaca ctactatcgc ttccattgct    240 gctaagaag agggagtttc cctcgagaag agagaggact gtaacgaatt gccaccgcgg    300
agaaacactg agattttgac tggttcctgg tccgatcaaa cttacccaga gggtactcag    360
gctatctaca gtgtagacc aggttacaga tccttgggta cgttatcat ggtttgtaga    420 aagggtgagt gggttgcttt gaacccattg agaaagtgtc agaaaagacc atgtggtcac    480
ccaggtgata ctccattcgg tactttcact ttgactggtg gtaacgtttt cgagtacggt    540
gttaaggctg tttacacttg taacgagggt taccagttgt tgggtgagat caactacaga    600
gagtgtgata ctgacggttg gactaacgac attccaatct gtgaggttgt taagtgtttg    660
ccagttactg ctccagaaa cggtaagatt gtttcctccg ctatggaacc agatagagag    720
taccacttcg tcaggctgt tagattcgtt tgtaactccg gttacaagat tgaaggtgac    780
gaagagatgc actgttctga tgacggtttc tggtccaaag aaaagccaaa gtgtgttgag    840
atttcctgta gtccccaga cgttattaac ggttcccca tctcccaaaa gatcatctac    900
aaagagaacg agagattcca gtacaagtgt aacatgggtt acgagtactc tgaaagaggt    960
gacgctgttt gtactgaatc tggttggaga ccattgccat cctgtgaaga agagtcctgt   1020
gacaacccat acattccaaa cggtgactac tccccattga gaatcaagca cagaactggt   1080
gacgagatca cttaccagtg tagaaacggt ttctacccag ctactagagg taacactgct   1140
aagtgtactt ccactggttg gattccagct ccaagatgta tctttgaagc catgtgactac   1200 ccagatatca agcacggtgg tttgtaccac gagaacatga agagaccata cttcccagtt   1260
gctgttggaa agtactactc ctactactgt gacgaacact tcgaaactcc atctggttct   1320
tactgggacc acatccactg tactcaagat ggttggtccc agctgttcc atgtttgaga   1380 aaatgttact cccatactt ggagaacggt tacaaccaga accatggtag aaagttcgtt   1440
cagggaaagt ccattgacgt tgcttgtcat ccaggttacg ctttgccaaa ggctcagact   1500
actgttactt gtatggaaaa cggttggtcc cctactccta atgtatcag agttaagact   1560
```

```
tgttccaagt cctccatcga cattgagaac ggtttcattt ccgagtccca gtacacttac    1620
gctttgaaag agaaggctaa gtaccagtgt aaattgggat acgttactgc tgacggtgaa    1680
acttccggtt ccatcacttg tggtaaggat ggttggtctg ctcaaccaac ttgtatcaag    1740
tcttgtgaca tcccagtttt catgaacgct agaactaaga acgacttcac atggttcaag    1800
ttgaacgaca ctttggacta cgaatgtcac gacggttacg aatctaacac tggttccact    1860
actggttcca tcgtttgtgg ttacaacggt tggtctgact tgccaatctg ttacgagaga    1920
gagtgcgagt tgccaaagat cgacgttcat ttggttccag acagaaagaa ggaccagtac    1980
aaggttggtg aggttttgaa gttctcctgt aagccaggtt tcactatcgt tggtccaaac    2040
tccgttcagt gttaccattt cggtttgtcc ccagacttgc ctatttgtaa agagcaggtt    2100
cagtcttgcg gtccaccacc agaattgttg aacggtaacg ttaaagaaaa gactaaagaa    2160
gagtacggtc actctgaggt tgttgagtac tactgtaacc aagattctt gatgaagggt    2220 ccaaacaaga tccaatgtgt tgacggtgag tggactactt tgccagtttg tatcgttgaa    2280
gagtccactt gtggtgacat tccagaattg gaacacggtt gggctcaatt gtcatcccca    2340
ccatactact acggtgactc cgttgagttc aactgttccg agtccttcac tatgattggt    2400
cacagatcca tcacatgtat ccacggtgtt tggactcaat tgccacagtg tgttgctatc    2460
gacaagttga agaagtgtaa atcctccaac ttgatcatct tggaggaaca cttgaagaac    2520
aagaaagagt tcgaccacaa ctccaacatc agatacagat gtagaggtaa gagggttgg    2580 attcacactg tttgtatcaa cggtagatgg gaccctgaag ttaactgttc catggctcag    2640
attcagttgt gtccaccacc tccacaaatt ccaaactccc acaacatgac tactactttg    2700
aactacagag atggtgagaa ggtttccgtt ttgtgtcaag agaactactt gatccaagag    2760
ggtgaggaaa tcacttgtaa ggacggtaga tggcaatcca tcccattgtg tgttgagaag    2820
atcccatgtt cccaaccacc acaaattgag cacggtacta tcaactcttc cagatcctct    2880
caagagtctt acgctcacgg tactaagttg tcctacactt gtgagggtgg tttcagaatc    2940
tctgaggaaa acgagactac ttgttacatg ggaaagtggt cctctccacc acaatgtgaa    3000
ggtttgcctt gtaagtctcc accagagatt tctcacggtg ttgttgctca catgtccgac    3060
tcttaccaat acggtgaaga ggttacttac aagtgtttcg agggtttcgg tattgatggt    3120
ccagctatcg ctaagtgttt gggtgaaaag tggtcccatc ctccatcctg tatcaagact    3180
gactgtttgt ccttgccatc tttcgagaac gctatcccaa tgggtgaaaa gaaggacgtt    3240
tacaaggctg tgaacaggt tacatacact tgtgctactt actacaagat ggacggtgct    3300
tccaacgtta cttgtatcaa ctccagatgg actggtagac caacttgtag agacacttcc    3360
tgtgttaacc caccaactgt tcagaacgct tacatcgttt ccagacagat gtctaagtac    3420
ccatccggtg agagagttag ataccaatgt agatccccat acgagatgtt cggtgacgaa    3480
gaggttatgt gtttgaacgg taattggact gaaccaccac agtgtaagga ctccactggt    3540
aagtgtggtc cacctccacc aattgacaac ggtgacatca cttctttccc attgtccgtt    3600
tacgctccag cttcttccgt tgagtaccag tgtcagaact tgtaccagtt ggagggtaac    3660
aagagaatca cttgtagaaa cggacaatgg tctgagccac caaagtgttt gcacccatgt    3720
gttatctcca gagaaatcat ggaaaactac aacattgctt tgagatggac tgctaagcag    3780
aagttgtact ccagaacagg tgagtctgtt gagtttgttt gtaagagagg ttacagattg    3840
tcctccagat cccacacttt gagaactaca tgtgggacg gaaagttgga gtacccaact    3900
tgtgctaaga gataatgagc ggccgcttaa ttaa                                3934
```

<210> SEQ ID NO 8
<211> LENGTH: 2848
<212> TYPE: DNA
<213> ORGANISM: Artificial
<220> FEATURE:
<223> OTHER INFORMATION: Codon optimised human hactor H variant

<400> SEQUENCE: 8

| | | | | | | |
|---|---|---|---|---|---|---|
| ggcgcgccgg | atccaaaaat | gagattccca | tccatcttca | ctgctgtttt | gttcgctgct | 60 |
| tcttctgctt | tggctgctcc | agttaacact | actactgagg | acgagactgc | tcaaattcca | 120 |
| gctgaggctg | ttattggtta | ctctgacttg | gaaggtgatt | tcgacgttgc | tgttttgcca | 180 |
| ttctccaact | ccactaacaa | cggtttgttg | ttcatcaaca | ctactatcgc | ttccattgct | 240 |
| gctaaagaag | agggagtttc | cctcgagaag | agagaggact | gtaacgaatt | gccaccgcgg | 300 |
| agaaacactg | agattttgac | tggttcctgg | tccgatcaaa | cttacccaga | gggtactcag | 360 |
| gctatctaca | gtgtagacc | aggttacaga | tccttgggta | acattatcat | ggtttgtaga | 420 |
| aagggtgagt | gggttgcttt | gaacccattg | agaaagtgtc | agaaaagacc | atgtggtcac | 480 |
| ccaggtgata | ctccattcgg | tacttttcact | ttgactggtg | gtaacgtttt | cgagtacggt | 540 |
| gttaaggctg | tttacacttg | taacgagggt | taccagttgt | tgggtgagat | caactacaga | 600 |
| gagtgtgata | ctgacggttg | gactaacgac | attccaatct | gtgaggttgt | taagtgtttg | 660 |
| ccagttactg | ctccagagaa | cggtaagatt | gtttcctccg | ctatggaacc | agatagagag | 720 |
| taccacttcg | gtcaggctgt | tagattcgtt | tgtaactccg | gttacaagat | gaaggtgac | 780 |
| gaagagatgc | actgttctga | tgacggtttc | tggtccaaag | aaaagccaaa | gtgtgttgag | 840 |
| atttcctgta | gtcccccaga | cgttattaac | ggttcccccaa | tctcccaaaa | gatcatctac | 900 |
| aaagagaacg | agagattcca | gtacaagtgt | aacatgggtt | acgagtactc | tgaaagaggt | 960 |
| gacgctgttt | gtactgaatc | tggttggaga | ccattgccat | cctgtgaaga | gaagtcctgt | 1020 |
| gacaacccat | acattccaaa | cggtgactac | tcccccattga | gaatcaagca | cagaactggt | 1080 |
| gacgagatca | cttaccagtg | tagaaacggt | ttctacccag | ctactagagg | taacactgct | 1140 |
| aagtgtactt | ccactggttg | gattccagct | ccaagatgta | ctttgaagcc | atgtgactac | 1200 |
| ccagatatca | agcacggtgg | tttgtaccac | gagaacatga | gaagaccata | cttcccagtt | 1260 |
| gctgttggaa | agtactactc | ctactactgt | gacgaacact | cgaaactcc | atctggttct | 1320 |
| tactgggacc | acatccactg | tactcaagat | ggttggtccc | cagctgttcc | atgtttgaga | 1380 |
| aaatgttact | tccatactt | ggagaacggt | acaaccaga | actacggtag | aaagttcgtt | 1440 |
| cagggaaagt | ccattgacgt | tgcttgtcat | ccaggttacg | ctttgccaaa | ggctcagact | 1500 |
| actgttactt | gtatggaaaaa | cggttggtcc | cctactccta | atgtatcag | agttaagact | 1560 |
| tgttccaagt | cctccatcga | cattgagaac | ggtttcattt | ccgagtccca | gtacacttac | 1620 |
| gctttgaaag | agaaggctaa | gtaccagtgt | aaattgggat | acgttactgc | tgacggtgaa | 1680 |
| acttccggtt | ccatcacttg | tggtaaggat | ggttggtctg | ctcaaccaac | ttgtatcaag | 1740 |
| tcttgtgaca | tcccagtttt | catgaacgct | agaactaaga | acgacttcac | atggttcaag | 1800 |
| ttgaacgaca | ctttggacta | cgaatgtcac | gacggttacg | aatctaacac | tggttccact | 1860 |
| actggttcca | tcgtttgtgg | ttacaacggt | tggtctgact | tgccaatctg | ttacgagttg | 1920 |
| ccttgtaagt | ctccaccaga | gatttctcac | ggtgttgttg | ctcacatgtc | cgactcttac | 1980 |
| caatacggtg | aagaggttac | ttacaagtgt | ttcgagggtt | tcggtattga | tggtccagct | 2040 |

```
atcgctaagt gtttgggtga aaagtggtcc catcctccat cctgtatcaa gactgactgt    2100
ttgtccttgc catctttcga gaacgctatc ccaatgggtg aaaagaagga cgtttacaag    2160
gctggtgaac aggttacata cacttgtgct acttactaca agatggacgg tgcttccaac    2220
gttacttgta tcaactccag atggactggt agaccaactt gtagagacac ttcctgtgtt    2280
aacccaccaa ctgttcagaa cgcttacatc gtttccagac agatgtctaa gtacccatcc    2340
ggtgagagag ttagatacca atgtagatcc ccatacgaga tgttcggtga cgaagaggtt    2400
atgtgtttga cggtaattg gactgaacca ccacagtgta aggactccac tggtaagtgt    2460
ggtccacctc caccaattga caacggtgac atcacttctt tcccattgtc cgtttacgct    2520
ccagcttctt ccgttgagta ccagtgtcag aacttgtacc agttggaggg taacaagaga    2580
atcacttgta gaaacggaca atggtctgag ccaccaaagt gtttgcaccc atgtgttatc    2640
tccagagaaa tcatggaaaa ctacaacatt gctttgagat ggactgctaa gcagaagttg    2700
tactccagaa caggtgagtc tgttgagttt gtttgtaaga gaggttacag attgtcctcc    2760
agatcccaca ctttgagaac tacatgttgg gacggaaagt tggagtaccc aacttgtgct    2820
aagagataat gagcggccgc ttaattaa                                       2848
```

<210> SEQ ID NO 9
<211> LENGTH: 3742
<212> TYPE: DNA
<213> ORGANISM: Artificial
<220> FEATURE:
<223> OTHER INFORMATION: Codon optimised mouse hactor H variant

<400> SEQUENCE: 9

```
ggcgcgccgg atccaaaaat gagattgtcc gctagaatca tctggttgat cttgtggact      60
gtttgtgctg ctgaggattg taaaggtcca ccaccgcggg aaaactccga gattttgtct     120
ggttcttggt ccgaacaatt gtacccagag ggtactcaag ctacttacaa gtgtagacca     180
ggttacagaa ctttgggtac tatcgttaag gtttgtaaga cggaaagtg ggttgcttct     240
aacccatcca aatctgtag aaagaaacca tgtggtcacc caggtgatac tccattcggt     300
tccttcagat tggctgttgg ttcccaattc gagttcggtg ctaaggttgt ttacacttgt     360
gacgacggtt accaattgtt gggtgagatc gactacagag aatgtggtgc tgacggttgg     420
attaacgaca tcccattgtg tgaggttgtt aagtgtttgc agttactga gttggagaac     480
ggtagaattg tttctggtgc tgctgaaact gaccaagagt actacttcgg acaggttgtt     540
agattcgagt gtaactccgg tttcaagatc gaaggtcaca aagagattca ctgttccgag     600
aacggtttgt ggtctaacga aagccaaga tgtgttgaga ttttgtgtac tccaccaaga     660
gttgaaaacg tgacggtat caacgttaag ccagtttaca agagaacga gagataccac     720
tacaagtgta agcacggtta cgttccaaaa gaaagaggtg acgctgtttg tactggttct     780
ggttggtcct ctcaaccatt ctgtgaagag aagagatgtt ccccaccata catcttgaac     840
ggtatctaca ctccacacag aatcattcac agatccgacg acgagattag atacgaatgt     900
aactacggat tctacccagt tactggttcc actgtttcca gtgtactcc aactggttgg     960
attccagttc caagatgtac tttgaagcca tgtgagttcc cacaattcaa gtacggtaga    1020
ttgtactacg aagagtcctt gagaccaaac ttcccagttt ccatcggtaa caagtactcc    1080
tacaagtgtg acaacggttt ctctccacca tctggttact cttgggacta cttgagatgt    1140
actgctcaag ttgggaacc agaggttcca tgtgttagaa agtgttttt ccactacgtt    1200
gagaacggtg attctgctta ctgggagaag gtttacgttc aaggtcagtc cttgaaggtt    1260
```

```
cagtgttaca acggttactc cttgcaaaac ggtcaggaca ctatgacttg tactgagaac    1320
ggttggtcac caccaccaaa gtgtatcaga atcaagactt gttccgcttc cgacattcac    1380
atcgacaacg gattcttgtc tgagtcctcc tccatttacg ctttgaacag agagacttcc    1440
tacagatgta agcagggata cgttacaaac actggtgaga tttccggttc catcacttgt    1500
ttgcagaatg gttggtcccc acagccatct tgtattaagt cctgtgacat gccagttttc    1560
gagaactcca tcactaagaa cactagaaca tggttcaagt tgaacgacaa gttggactac    1620
gagtgtttgg ttggtttcga gaacgagtac aagcacacta agggttccat cacatgtact    1680
tactacggtt ggtctgacac tccatcctgt tacgaaagag agtgttccgt tccaactttg    1740
gacagaaagt tggttgtttc cccaagaaaa gagaagtaca gagttggaga cttgttggag    1800
ttctcttgtc actctggtca tagagttggt ccagactccg ttcaatgtta ccactttgga    1860
tggtccccag gttttccaac ttgtaagggt caggttgctt cttgtgctcc accattggag    1920
attttgaacg gtgagatcaa cggtgctaag aaggttgaat actcccacgg tgaagttgtt    1980
aagtacgact gtaagccaag attcttgttg aagggtccaa acaagatcca atgtgttgac    2040
ggtaactgga ctactttgcc agtttgtatc gaggaagaaa gaacttgcgg agacatccca    2100
gaattggaac acggttccgc taagtgttct gttccaccat accaccatgg tgattccgtt    2160
gagttcatct gtgaggaaaa cttcactatg atcggtcacg gttccgtttc ttgtatttcc    2220
ggtaagtgga ctcagttgcc aaagtgtgtt gctactgacc agttggagaa gtgtagagtt    2280
ttgaagtcca ctggtatcga ggctatcaag ccaaagttga ctgagttcac tcacaactcc    2340
actatggact acaaatgtag agacaagcaa gagtacgaga gatccatctg tatcaacggt    2400
aaatgggacc agaaccaaa ctgtacttcc aagacttctt gtccaccacc accacaaatt    2460
ccaaacactc aggttatcga gactactgtt aagtacttgg acggtgagaa gttgtccgtt    2520
ttgtgtcagg acaactactt gactcaagac tccgaagaga tggtttgtaa ggacggtaga    2580
tggcaatctt tgccaagatg tatcgagaag atcccatgtt ctcagccacc aactattgag    2640
cacggttcca ttaacttgcc aagatcctcc gaagaaagaa gagactccat cgaatcctct    2700
tctcacgaac acggtactac tttctcttac gtttgtgatg acggtttcag aatcccagaa    2760
gagaacagaa tcacttgtta catgggaaag tggtccactc cacctagatg tgttggtttg    2820
ccatgtggtc caccaccttc tattccattg ggtactgttt ctttggagtt ggagtcctac    2880
caacacggtg aagaggttac ttaccactgt ccactggtt tcggtattga tggtccagct    2940
ttcattatct gtgagggtgg taagtggtct gatccaccta gtgtattaa gactgactgt    3000 gacgttttgc caactgttaa gaacgctatc atcagaggta agtccaagaa gtcctacaga    3060
actggagagc aggttacttt cagatgtcag tccccatacc aaatgaacgg ttccgacact    3120
gttacttgtg ttaactccag atggatcggt caaccagttt gtaaggataa ctcctgtgtt    3180
gatccaccac atgttccaaa cgctactatc gttactagaa ctaagaacaa gtacttgcat    3240
ggtgacagag ttagatatga gtgtaacaag ccattggagt tgttcggtca agttgaggtt    3300
atgtgtgaga acggtatctg gactgagaag ccaaagtgta gagactccac tggtaagtgt    3360
ggtcctccac caccaattga caacggtgac atcacttctt gtccttgcc agtttacgaa    3420 cctttgtcct ccgttgagta ccaatgtcag aagtactact tgttgaaagg taagaaaact    3480
atcacttgta ctaatggtaa atggtccgag ccaccaactt gtttgcacgc ttgtgttatc    3540
ccagagaaca tcatggaatc ccacaacatc atcttgaagt ggagacacac tgagaagatt    3600
```

-continued

| tactctcact ccggtgagga cattgagttc ggttgtaagt acggttacta caaggctaga | 3660 |
| gactctccac cattcagaac taagtgtatc aacggaacta tcaactaccc aacttgtgtt | 3720 |
| taatgagcgg ccgcttaatt aa | 3742 |

<210> SEQ ID NO 10
<211> LENGTH: 3943
<212> TYPE: DNA
<213> ORGANISM: Artificial
<220> FEATURE:
<223> OTHER INFORMATION: Codon optimised mouse hactor H variant

<400> SEQUENCE: 10

| ggcgcgccgg atccaaaaat gagattccca tccatcttca ctgctgtttt gttcgctgct | 60 |
| tcttctgctt tggctgctcc agttaacact actactgagg acgagactgc tcaaattcca | 120 |
| gctgaggctg ttattggtta ctctgacttg aaggtgatt tcgacgttgc tgttttgcca | 180 |
| ttctccaact ccactaacaa cggtttgttt tcatcaaca ctactatcgc ttccattgct | 240 |
| gctaaagaag agggagtttc cctcgagaag agagaggatt gtaaaggtcc accacgcgg | 300 |
| gaaaactccg agattttgtc tggttcttgg tccgaacaat gtacccaga gggtactcaa | 360 |
| gctacttaca gtgtagacc aggttacaga actttgggta ctatcgttaa ggtttgtaag | 420 |
| aacggaaagt gggttgcttc tcaaccatcc agaatctgta gaagaaacc atgtggtcac | 480 |
| ccaggtgata ctccattcgg ttccttcaga ttggctgttg gttcccaatt cgagttcggt | 540 |
| gctaaggttg tttacacttg tgacgacggt taccaattgt ggggtgagat cgactacaga | 600 |
| gaatgtggtc tgacggttg gattaacgac atcccattgt gtgaggttgt taagtgtttg | 660 |
| ccagttactg agttggagaa cggtagaatt gttttctggtg ctgctgaaac tgaccaagag | 720 |
| tactacttcg acaggttgt tagattcgag tgtaactccg gtttcaagat cgaaggtcac | 780 |
| aaagagattc actgttccga aacggtttg tggtctaacg agaagccaag atgtgttgag | 840 |
| attttgtgta ctccaccaag agttgaaaac ggtgacggta tcaacgttaa gccagtttac | 900 |
| aaagagaacg agagatacca ctacaagtgt aagcacggtt acgttccaaa gaaagaggt | 960 |
| gacgctgttt gtactggttc tggttggtcc tctcaaccat ctgtgaaga aagagatgt | 1020 |
| tccccaccat acatcttgaa cggtatctac actccacaca gaatcattca cagatccgac | 1080 |
| gacgagatta gatacgaatg taactacgga ttctacccag ttactggttc cactgtttcc | 1140 |
| aagtgtactc caactggttg gattccagtt ccaagatgta ctttgaagcc atgtgagttc | 1200 |
| ccacaattca gtacggtag attgtactac aagagtcct tgagaccaaa cttcccagtt | 1260 |
| tccatcggta acaagtactc ctacaagtgt gacaacggtt tctctccacc atctggttac | 1320 |
| tcttgggact acttgagatg tactgctcaa ggttgggaac cagaggttcc atgtgttaga | 1380 |
| aagtgtgttt tccactacgt tgagaacggt gattctgctt actgggagaa ggtttacgtt | 1440 |
| caaggtcagt ccttgaaggt tcagtgttac aacggttact ccttgcaaaa cggtcaggac | 1500 |
| actatgactt gtactgagaa cggttggtca ccaccaccaa gtgtatcag atcaagact | 1560 |
| tgttccgctt ccgacattca catcgacaac ggattcttgt ctgagtcctc ctccatttac | 1620 |
| gctttgaaca gagagacttc ctacagatgt aagcaggat acgttacaaa cactggtgag | 1680 |
| atttccggtt ccatcacttg tttgcagaat ggttggtccc acagccatc ttgtattaag | 1740 |
| tcctgtgaca tgccagtttt cgagaactcc atcactaaga cactagaac atggttcaag | 1800 |
| ttgaacgaca agttggacta cgagtgtttg gttggtttcg agaacgagta caagcacact | 1860 |
| aagggttcca tcacatgtac ttactacggt tggtctgaca ctccatccctg ttacgaaaga | 1920 |

```
gagtgttccg ttccaacttt ggacagaaag ttggttgttt ccccaagaaa agagaagtac    1980
agagttggag acttgttgga gttctcttgt cactctggtc atagagttgg tccagactcc    2040
gttcaatgtt accactttgg atggtcccca ggttttccaa cttgtaaggg tcaggttgct    2100
tcttgtgctc caccattgga gattttgaac ggtgagatca acggtgctaa gaaggttgaa    2160
tactcccacg gtgaagttgt taagtacgac tgtaagccaa gattcttgtt gaagggtcca    2220
aacaagatcc aatgtgttga cggtcaatgg actactttgc cagtttgtat cgaggaagaa    2280
agaacttgcg gagacatccc agaattggaa cacggttccg ctaagtgttc tgttccacca    2340
taccaccatg gtgattccgt tgagttcatc tgtgaggaac aattcactat gatcggtcac    2400
ggttccgttt cttgtatttc cggtaagtgg actcagttgc caaagtgtgt tgctactgac    2460
cagttggaga gtgtagagt tttgaagtcc actggtatcg aggctatcaa gccaaagttg    2520
actgagttca ctcaccagtc cactatggac tacaaatgta gagacaagca agagtacgag    2580
agatccatct gtatcaacgg taaatgggac ccagaaccac aatgtacttc caagacttct    2640
tgtccaccac caccacaaat tccaaacact caggttatcg agactactgt taagtacttg    2700
gacggtgaga agttgtccgt tttgtgtcag gacaactact tgactcaaga ctccgaagag    2760
atggtttgta aggacggtag atggcaatct ttgccaagat gtatcgagaa gatcccatgt    2820
tctcagccac caactattga gcacggttcc attaacttgc caagatcctc cgaagaaaga    2880
agagactcca tcgaatcctc ttctcacgaa cacggtacta ctttctctta cgtttgtgat    2940
gacggtttca gaatcccaga agagaacaga atcacttgtt acatgggaaa gtggtccact    3000
ccacctagat gtgttggttt gccatgtggt ccaccacctt ctattccatt gggtactgtt    3060
tctttggagt tggagtccta ccaacacggt gaagaggtta cttaccactg ttccactggt    3120
ttcggtattg atggtccagc tttcattatc tgtgagggtg gtaagtggtc tgatccacct    3180
aagtgtatta agactgactg tgacgttttg ccaactgtta gaacgctat catcagaggt    3240 aagtccaaga agtcctacag aactggagag caggttactt tcagatgtca gtccccatac    3300
caaatgcaag ttccgacac tgttacttgt gttaactcca gatggatcgg tcaaccagtt    3360
tgtaaggata actcctgtgt tgatccacca catgttccac aagctactat cgttactaga    3420
actaagaaca agtacttgca tggtgacaga gttagatatg agtgtaacaa gccattggag    3480
ttgttcggtc aagttgaggt tatgtgtgag aacggtatct ggactgagaa gccaaagtgt    3540
agagactcca ctggtaagtg tggtcctcca ccaccaattg acaacggtga catcacttct    3600
ttgtccttgc agtttacga accttttgtcc tccgttgagt accaatgtca gaagtactac    3660
ttgttgaaag gtaagaaaac tatcacttgt actaatggta aatggtccga gccaccaact    3720
tgtttgcacg cttgtgttat cccagagaac atcatggaat cccacaacat catcttgaag    3780
tggagacaca ctgagaagat ttactctcac tccggtgagg acattgagtt cggttgtaag    3840
tacggttact acaaggctag agactctcca ccattcagaa ctaagtgtat ccaaggaact    3900
atcaactacc caacttgtgt ttaatgagcg gccgcttaat taa                      3943
```

<210> SEQ ID NO 11
<211> LENGTH: 3742
<212> TYPE: DNA
<213> ORGANISM: Artificial
<220> FEATURE:
<223> OTHER INFORMATION: Codon optimised mouse hactor H variant

<400> SEQUENCE: 11

```
ggcgcgccgg atccaaaaat gagattgtcc gctagaatca tctggttgat cttgtggact     60
gtttgtgctg ctgaggattg taaaggtcca ccaccgcggg aaaactccga gattttgtct    120
ggttcttggt ccgaacaatt gtacccagag ggtactcaag ctacttacaa gtgtagacca    180
ggttacagaa ctttgggtac tatcgttaag gtttgtaaga acggaaagtg ggttgcttct    240
caaccatcca gaatctgtag aaagaaacca tgtggtcacc caggtgatac tccattcggt    300
tccttcagat tggctgttgg ttcccaattc gagttcggtg ctaaggttgt ttacacttgt    360
gacgacggtt accaattgtt gggtgagatc gactacagag aatgtggtgc tgacggttgg    420
attaacgaca tcccattgtg tgaggttgtt aagtgtttgc cagttactga gttggagaac    480
ggtagaattg tttctggtgc tgctgaaact gaccaagagt actacttcgg acaggttgtt    540
agattcgagt gtaactccgg tttcaagatc gaaggtcaca aagagattca ctgttccgag    600
aacggtttgt ggtctaacga aagccaaga tgtgttgaga ttttgtgtac tccaccaaga    660
gttgaaaacg tgacggtat caacgttaag ccagtttaca aagagaacga gagataccac    720
tacaagtgta agcacggtta cgttccaaaa gaaagaggtg acgctgtttg tactggttct    780
ggttggtcct ctcaaccatt ctgtgaagag aagagatgtt ccccaccata catcttgaac    840
ggtatctaca ctccacacag aatcattcac agatccgacg acgagattag atacgaatgt    900
aactacggat tctacccagt tactggttcc actgtttcca gtgtactcc aactggttgg    960
attccagttc caagatgtac tttgaagcca tgtgagttcc cacaattcaa gtacggtaga   1020
ttgtactacg aagagtcctt gagaccaaac ttcccagttt ccatcggtaa caagtactcc   1080
tacaagtgtg acaacggttt ctctccacca tctggttact cttgggacta cttgagatgt   1140
actgctcaag gttgggaacc agaggttcca tgtgttagaa agtgtgtttt ccactacgtt   1200
gagaacggtg attctgctta ctgggagaag gtttacgttc aaggtcagtc cttgaaggtt   1260
cagtgttaca acggttactc cttgcaaaac ggtcaggaca ctatgacttg tactgagaac   1320
ggttggtcac caccaccaaa gtgtatcaga atcaagactt gttccgcttc cgacattcac   1380
atcgacaacg gattcttgtc tgagtcctcc tccatttacg ctttgaacag agagacttcc   1440
tacagatgta agcagggata cgttacaaac actggtgaga tttccggttc catcacttgt   1500
ttgcagaatg gttggtcccc acagccatct tgtattaagt cctgtgacat gccagttttc   1560
gagaactcca tcactaagaa cactagaaca tggttcaagt tgaacgacaa gttggactac   1620
gagtgtttgg ttggtttcga gaacgagtac aagcacacta agggttccat cacatgtact   1680
tactacggtt ggtctgacac tccatcctgt tacgaaagag agtgttccgt tccaactttg   1740
gacagaaagt tggttgtttc cccaagaaaa gagaagtaca gagttggaga cttgttggag   1800
ttctcttgtc actctggtca tagagttggt ccagactccg ttcaatgtta ccactttgga   1860
tggtccccag gttttccaac ttgtaagggt caggttgctt cttgtgctcc accattggag   1920
attttgaacg tgagatcaa cggtgctaag aaggttgaat actcccacgg tgaagttgtt   1980
aagtacgact gtaagccaag attcttgttg aagggtccaa acaagatcca atgtgttgac   2040
ggtcaatgga ctactttgcc agtttgtatc gaggaagaaa gaacttgcgg agacatccca   2100
gaattggaac acggttccgc taagtgttct gttccaccat accaccatgg tgattccgtt   2160
gagttcatct gtgaggagta gttcactatg atcggtcacg gttccgtttc ttgtatttcc   2220
ggtaagtgga ctcagttgcc aaagtgtgtt gctactgacc agttggagaa gtgtagagtt   2280
ttgaagtcca ctggtatcga ggctatcaag ccaaagttga ctgagttcac tcaccagtct   2340
actatggact acaaatgtag agacaagcaa gagtacgaga gatccatctg tatcaacggt   2400
```

```
aaatgggacc cagaaccaca atgtacttcc aagacttctt gtccaccacc accacaaatt    2460
ccaaacactc aggttatcga gactactgtt aagtacttgg acggtgagaa gttgtccgtt    2520
ttgtgtcagg acaactactt gactcaagac tccgaagaga tggtttgtaa ggacggtaga    2580
tggcaatctt tgccaagatg tatcgagaag atcccatgtt ctcagccacc aactattgag    2640
cacggttcca ttaacttgcc aagatcctcc gaagaaagaa gagactccat cgaatcctct    2700
tctcacgaac acggtactac tttctcttac gtttgtgatg acggtttcag aatcccagaa    2760
gagaacagaa tcacttgtta catgggaaag tggtccactc cacctagatg tgttggtttg    2820
ccatgtggtc caccccttc tattccattg ggtactgttt ctttggagtt ggagtcctac    2880
caacacggtg aagaggttac ttaccactgt tccactggtt tcggtattga tggtccagct    2940
ttcattatct gtgagggtgg taagtggtct gatccaccta agtgtattaa gactgactgt    3000
gacgttttgc caactgttaa gaacgctatc atcagaggta agtccaagaa gtcctacaga    3060
actggagagc aggttacttt cagatgtcag tccccatacc aaatgcaagg ttccgacact    3120
gttacttgtg ttaactccag atggatcggt caaccagttt gtaaggataa ctcctgtgtt    3180
gatccaccac atgttccaca agctactatc gttactagaa ctaagaacaa gtacttgcat    3240
ggtgacagag ttagatatga gtgtaacaag ccattggagt tgttcggtca agttgaggtt    3300
atgtgtgaga acggtatctg gactgagaag ccaaagtgta gagactccac tggtaagtgt    3360
ggtcctccac caccaattga caacggtgac atcacttctt tgtccttgcc agtttacgaa    3420
cctttgtcct ccgttgagta ccaatgtcag aagtactact tgttgaaagg taagaaaact    3480
atcacttgta ctaatggtaa atggtccgag ccaccaactt gtttgcacgc ttgtgttatc    3540
ccagagaaca tcatggaatc ccacaacatc atcttgaagt ggagacacac tgagaagatt    3600
tactctcact ccggtgagga cattgagttc ggttgtaagt acggttacta caaggctaga    3660
gactctccac cattcagaac taagtgtatc caaggaacta tcaactaccc aacttgtgtt    3720
taatgagcgg ccgcttaatt aa                                             3742
```

<210> SEQ ID NO 12
<211> LENGTH: 3742
<212> TYPE: DNA
<213> ORGANISM: Artificial
<220> FEATURE:
<223> OTHER INFORMATION: Codon optimised mouse hactor H variant

<400> SEQUENCE: 12

```
ggcgcgccgg atccaaaaat gagattgtcc gctagaatca tctggttgat cttgtggact     60
gtttgtgctg ctgaggattg taaaggtcca ccaccgcggg aaaactccga gattttgtct    120
ggttcttggt ccgaacaatt gtacccgag ggtactcaag ctacttacaa gtgtagacca    180
ggttacagaa ctttgggtac tatcgttaag gtttgtaaga acggaaagtg ggttgcttct    240
caaccatcca gaatctgtag aaagaaacca tgtggtcacc caggtgatac tccattcggt    300
tccttcagat tggctgttgg ttcccaattc gagttcggtg ctaaggttgt ttacacttgt    360
gacgacggtt accaattgtt gggtgagatc gactacagag aatgtggtgc tgacggttgg    420
attaacgaca tcccattgtg tgaggttgtt aagtgtttgc agttactga gttggagaac    480 ggtagaattg tttctggtgc tgctgaaact gaccaagagt actactcgg acaggttgtt    540 agattcgagt gtaactccgg tttcaagatc gaaggtcaca agagattcca ctgttccgag    600
aacggtttgt ggtctaacga gaagccaaga tgtgttgaga ttttgtgtac tccaccaaga    660
```

```
gttgaaaacg gtgacggtat caacgttaag ccagtttaca agagaacga gagataccac    720 tacaagtgta agcacggtta cgttccaaaa gaaagaggtg acgctgtttg tactggttct    780
ggttggtcct ctcaaccatt ctgtgaagag aagagatgtt ccccaccata catcttgaac    840
ggtatctaca ctccacacag aatcattcac agatccgacg acgagattag atacgaatgt    900
aactacggat tctacccagt tactggttcc actgtttcca agtgtactcc aactggttgg    960
attccagttc caagatgtac tttgaagcca tgtgagttcc cacaattcaa gtacggtaga   1020
ttgtactacg aagagtcctt gagaccaaac ttcccagttt ccatcggtaa caagtactcc   1080
tacaagtgtg acaacggttt ctctccacca tctggttact cttgggacta cttgagatgt   1140
actgctcaag gttgggaacc agaggttcca tgtgttagaa agtgtgtttt ccactacgtt   1200
gagaacggtg attctgctta ctgggagaag gtttacgttc aaggtcagtc cttgaaggtt   1260
cagtgttaca acggttactc cttgcaaaac ggtcaggaca ctatgacttg tactgagaac   1320
ggttggtcac caccaccaaa gtgtatcaga atcaagactt gttccgcttc cgacattcac   1380
atcgacaacg gattcttgtc tgagtcctcc tccatttacg ctttgaacag agagacttcc   1440
tacagatgta agcagggata cgttacaaac actggtgaga tttccggttc catcacttgt   1500
ttgcagaatg gttggtcccc acagccatct tgtattaagt cctgtgacat gccagttttc   1560
gagaactcca tcactaagaa cactagaaca tggttcaagt tgaacgacaa gttggactac   1620
gagtgtttgg ttggtttcga gaacgagtac aagcacacta agggttccat cacatgtact   1680
tactacggtt ggtctgacac tccatcctgt tacgaaagag agtgttccgt tccaactttg   1740
gacagaaagt tggttgtttc cccaagaaaa gagaagtaca gagttggaga cttgttggag   1800
ttctcttgtc actctggtca tagagttggt ccagactccg ttcaatgtta ccactttgga   1860
tggtccccag ttttccaac ttgtaaggg caggttgctt cttgtgctcc accattggag   1920
attttgaacg gtgagatcaa cggtgctaag aaggttgaat actcccacgg tgaagttgtt   1980
aagtacgact gtaagccaag attcttgttg aagggtccaa acaagatcca atgtgttgac   2040
ggtcaatgga ctactttgcc agtttgtatc gaggaagaaa gaacttgcgg agacatccca   2100
gaattggaac acggttccgc taagtgttct gttccaccat accacatgg tgattccgtt   2160 gagttcatct gtgaggagta gttcactatg atcggtcacg gttccgtttc ttgtatttcc   2220
ggtaagtgga ctcagttgcc aaagtgtgtt gctactgacc agttggagaa gtgtagagtt   2280
ttgaagtcca ctggtatcga ggctatcaag ccaaagttga ctgagttcac tcaccagtcc   2340
actatggact acaaatgtag agacaagcaa gagtacgaga gatccatctg tatcaacggt   2400
aaatgggacc cagaaccaca atgtacttcc aagacttctt gtccaccacc accacaaatt   2460
ccaaacactc aggttatcga gactactgtt aagtacttgg acggtgagaa gttgtccgtt   2520
ttgtgtcagg acaactactt gactcaagac tccgaagaga tggtttgtaa ggacggtaga   2580
tggcaatctt tgccaagatg tatcgagaag atcccatgtt ctcagccacc aactattgag   2640
cacggttcca ttaacttgcc aagatcctcc gaagaaagaa gagactccat cgaatcctct   2700
tctcacgaac acggtactac tttctcttac gtttgtgatg acggtttcag aatcccagaa   2760
gagaacagaa tcacttgtta catgggaaag tggtccactc cacctagatg tgttggtttg   2820
ccatgtggtc caccacttc tattccattg gtactgtttt ctttggagtt ggagtcctac   2880
caacacggtg aagaggttac ttaccactgt ccactggtt tcggattga tggtccagct   2940 ttcattatct gtgagggtgg taagtggtct gatccaccta agtgtattaa gactgactgt   3000
gacgttttgc caactgttaa gaacgctatc atcagaggta agtccaagaa gtcctacaga   3060
```

-continued

```
actggagagc aggttacttt cagatgtcag tccccatacc aaatgtaggg ttccgacact    3120
gttacttgtg ttaactccag atggatcggt caaccagttt gtaaggataa ctcctgtgtt    3180
gatccaccac atgttccaca agctactatc gttactagaa ctaagaacaa gtacttgcat    3240
ggtgacagag ttagatatga gtgtaacaag ccattggagt tgttcggtca agttgaggtt    3300
atgtgtgaga acggtatctg gactgagaag ccaaagtgta gagactccac tggtaagtgt    3360
ggtcctccac caccaattga caacggtgac atcacttctt gtccttgcc agtttacgaa     3420
cctttgtcct ccgttgagta ccaatgtcag aagtactact tgttgaaagg taagaaaact    3480
atcacttgta ctaatggtaa atggtccgag ccaccaactt gtttgcacgc ttgtgttatc    3540
ccagagaaca tcatggaatc ccacaacatc atcttgaagt ggagacacac tgagaagatt    3600
tactctcact ccggtgagga cattgagttc ggttgtaagt acggttacta caaggctaga    3660
gactctccac cattcagaac taagtgtatc caaggaacta tcaactaccc aacttgtgtt    3720
taatgagcgg ccgcttaatt aa    3742
```

<210> SEQ ID NO 13
<211> LENGTH: 3733
<212> TYPE: DNA
<213> ORGANISM: Artificial
<220> FEATURE:
<223> OTHER INFORMATION: Codon optimised human hactor H variant

<400> SEQUENCE: 13

```
ggcgcgccgg atccaaaaat gagattgttg gctaagatca tctgtttgat gttgtgggct     60
atctgtgttg ctgaggactg taacgaattg ccaccgcgga gaaacactga gattttgact    120
ggttcctggt ccgatcaaac ttacccagag ggtactcagg ctatctacaa gtgtagacca    180
ggttacagat ccttgggtaa catcatcatg gtttgtagaa agggtgagtg ggttgctttg    240
aacccattga gaaagtgtca gaaaagacca tgtggtcacc caggtgatac tccattcggt    300
actttcactt tgactggtgg taacgttttc gagtacggtg ttaaggctgt ttacacttgt    360
aacgagggtt accagttgtt gggtgagatc aactacagag agtgtgatac tgacggttgg    420
actaacgaca ttccaatctg tgaggttgtt aagtgtttgc cagttactgc tccagagaac    480
ggtaagattg ttcctccgc tatggaacca gatagagagt accacttcgg tcaggctgtt    540
agattcgttt gtaactccgg ttacaagatt gaaggtgacg aagagatgca ctgttctgat    600
gacggtttct ggtccaaaga aaagccaaag tgtgttgaga tttcctgtaa gtccccagac    660
gttattaacg gttccccaat ctcccaaaag atcatctaca agagaacga gagattccag    720
tacaagtgta acatgggtta cgagtactct gaaagaggtg acgctgtttg tactgaatct    780
ggttggagac cattgccatc ctgtgaagag aagtcctgtg acaacccata cattccaaac    840
ggtgactact ccccattgag aatcaagcac agaactggtg acgagatcac ttaccagtgt    900
agaaacggtt tctacccagc tactagaggt aacactgcta gtgtacttc cactggttgg    960
attccagctc caagatgtac tttgaagcca tgtgactacc cagatatcaa gcacggtggt   1020
ttgtaccacg agaacatgag aagaccatac ttcccagttg ctgttggaaa gtactactcc   1080
tactactgtg acgaacactt cgaaactcca tctggttctt actgggacca catccactgt   1140
actcaagatg gttggtcccc agctgttcca tgtttgagaa aatgttactt cccatacttg   1200
gagaacggtt acaaccagaa ctacggtaga aagttcgttc agggaaagtc cattgacgtt   1260
gcttgtcatc caggttacgc tttgccaaag gctcagacta ctgttacttg tatggaaaac   1320
```

-continued

```
ggttggtccc ctactcctag atgtatcaga gttaagactt gttccaagtc ctccatcgac    1380
attgagaacg gtttcatttc cgagtcccag tacacttacg ctttgaaaga aaggctaag     1440 taccagtgta aattgggata cgttactgct gacggtgaaa cttccggttc catcacttgt    1500
ggtaaggatg gttggtctgc tcaaccaact tgtatcaagt cttgtgacat cccagttttc    1560
atgaacgcta gaactaagaa cgacttcaca tggttcaagt tgaacgacac tttggactac    1620
gaatgtcacg acggttacga atctaacact ggttccacta ctggttccat cgttgtggt     1680 tacaacggtt ggtctgactt gccaatctgt tacgagagag agtgcgagtt gccaaagatc    1740
gacgttcatt tggttccaga cagaaagaag gaccagtaca aggttggtga ggttttgaag    1800
ttctcctgta agccaggttt cactatcgtt ggtccaaact ccgttcagtg ttaccatttc    1860
ggtttgtccc cagacttgcc tatttgtaaa gagcaggttc agtcttgcgg tccaccacca    1920
gaattgttga acggtaacgt taaagaaaag actaagaag agtacggtca ctctgaggtt     1980
gttgagtact actgtaaccc aagattcttg atgaagggtc caaacaagat ccaatgtgtt    2040
gacggtgagt ggactacttt gccagtttgt atcgttgaag agtccacttg tggtgacatt    2100
ccagaattgg aacacggttg ggctcaattg tcatccccac catactacta cggtgactcc    2160
gttgagttca ctgttccga gtccttcact atgattggtc acagatccat cacatgtatc      2220
cacggtgttt ggactcaatt gccacagtgt gttgctatcg acaagttgca acaatgtcaa    2280
tcctccaact tgatcatctt ggaggaacac ttgaagaaca agcaagagtt cgaccacaac    2340
tccaacatcc aataccaatg tcaaggtcaa gagggttgga ttcacactgt tgtatcaac     2400 ggtcaatggg accctgaagt taactgttcc atggctcaga ttcagttgtg tccaccacct    2460
ccacaaattc caaactccca caacatgact actactttga actacagaga tggtgagaag    2520
gtttccgttt tgtgtcaaga gaactacttg atccaagagg gtgaggaaat cacttgtaag    2580
gacggtagat ggcaatccat cccattgtgt gttgagaaga tcccatgttc caaccacca     2640 caaattgagc acggtactat caactcttcc agatcctctc aagagtctta cgctcacggt    2700
actaagttgt cctacacttg tgagggtggt ttcagaatct ctgaggaaaa cgagactact    2760
tgttacatgg gaaagtggtc ctctccacca caatgtgaag gtttgccttg taagtctcca    2820
ccagagattt ctcacggtgt tgttgctcac atgtccgact cttaccaata cggtgaagag    2880
gttacttaca agtgtttcga gggttcggt attgatggtc cagctatcgc taagtgttg      2940 ggtgaaaagt ggtcccatcc tccatcctgt atcaagactg actgtttgtc cttgccatct    3000
ttcgagaacg ctatcccaat gggtgaaaag aaggacgttt acaaggctgg tgaacaggtt    3060
acatacactt gtgctactta ctacaagatg gacggtgctt ccaacgttac ttgtatcaac    3120
tccagatgga ctggtagacc aacttgtaga gacacttcct gtgttaaccc accaactgtt    3180
cagaacgctt acatcgtttc cagacagatg tctaagtacc catccggtga gagagttaga    3240
taccaatgta gatccccata cgagatgttc ggtgacgaag aggttatgtg tttgaacggt    3300
aattggactg aaccaccaca gtgtaaggac tccactggta agtgtggtcc acctccacca    3360
attgacaacg gtgacatcac ttctttccca ttgtccgttt acgctccagc ttcttccgtt    3420
gagtaccagt gtcagaactt gtaccagttg gagggtaaca agagaatcac ttgtagaaac    3480
ggacaatggc tgagccacc aaagtgtttg cacccatgtg ttatctccag agaaatcatg    3540
gaaaactaca cattgctttg agatggact gctaagcaga agttgtactc cagaacaggt    3600
gagtctgttg agtttgtttg taagagaggt tacagattgt cctccagatc ccacactttg    3660
```

-continued

```
agaactacat gttgggacgg aaagttggag tacccaactt gtgctaagag ataatgagcg   3720
gccgcttaat taa                                                        3733
```